United States Patent
Kraus et al.

(10) Patent No.: US 11,969,256 B2
(45) Date of Patent: Apr. 30, 2024

(54) SYSTEMS AND METHODS FOR THE ACUTE EVALUATION OF TRAUMATIC BRAIN INJURIES

(71) Applicant: Northwestern University, Evanston, IL (US)

(72) Inventors: Nina Kraus, Evanston, IL (US); Jennifer Lynn Krizman, Evanston, IL (US); Trent George Nicol, Evanston, IL (US); Travis White-Schwoch, Evanston, IL (US)

(73) Assignee: Northwestern University, Evanston, IL (US)

( * ) Notice: Subject to any disclaimer, the term of this patent is extended or adjusted under 35 U.S.C. 154(b) by 655 days.

(21) Appl. No.: 16/641,011

(22) PCT Filed: Aug. 24, 2018

(86) PCT No.: PCT/US2018/047881
§ 371 (c)(1),
(2) Date: Feb. 21, 2020

(87) PCT Pub. No.: WO2019/040830
PCT Pub. Date: Feb. 28, 2019

(65) Prior Publication Data
US 2021/0121119 A1 Apr. 29, 2021

Related U.S. Application Data

(60) Provisional application No. 62/549,788, filed on Aug. 24, 2017.

(51) Int. Cl.
*A61B 5/00* (2006.01)
*A61B 5/374* (2021.01)
(Continued)

(52) U.S. Cl.
CPC ............... *A61B 5/38* (2021.01); *A61B 5/374* (2021.01); *A61B 5/4842* (2013.01); *A61B 5/369* (2021.01); *A61B 5/4064* (2013.01)

(58) Field of Classification Search
CPC .......... A61B 5/38; A61B 5/374; A61B 5/4842; A61B 5/369; A61B 5/4064
See application file for complete search history.

(56) References Cited

U.S. PATENT DOCUMENTS 8,014,853 B2 9/2011 Kraus
8,712,514 B2 4/2014 Nicol
(Continued)

FOREIGN PATENT DOCUMENTS

WO 2017136656 A1 8/2017

OTHER PUBLICATIONS

Amanipour, R., et al (2016). Effects of Mild Traumatic Brain Injury on Auditory Function in a Mouse Model. Paper presented at the Biomedical Engineering Conference (SBEC), 201632nd Southern.
(Continued)

*Primary Examiner* — Scott M. Getzow
(74) *Attorney, Agent, or Firm* — Quarles & Brady LLP

(57) ABSTRACT

The present disclosure provides methods for identifying non-penetrating brain injury in a subject, as well as methods for classifying a subject that received a hit to the body that transmitted an impulsive force to the brain as either having a non-penetrating brain injury or not, by analyzing one or more components of frequency-following response (FFR) following administration of an acoustic stimulus to the subject. In addition, the present disclosure provides methods for assessing a subject's recovery from a non-penetrating brain injury. Also disclosed herein are processes and systems
(Continued)

for automatically generating acoustic stimuli and processing brain response data to identify non-penetrating brain injuries in subjects.

27 Claims, 20 Drawing Sheets

(51) Int. Cl.
*A61B 5/38* (2021.01)
*A61B 5/369* (2021.01)

(56) References Cited

U.S. PATENT DOCUMENTS

| | | | |
|---|---|---|---|
| 8,825,140 | B2 | 9/2014 | Rice |
| 10,588,536 | B2 * | 3/2020 | Kraus ............... A61B 5/375 |
| 2007/0112277 | A1 * | 5/2007 | Fischer ............ A61B 5/6817 |
| | | | 600/544 |
| 2011/0144520 | A1 * | 6/2011 | Causevic ........... A61B 5/7203 |
| | | | 600/544 |
| 2014/0171820 | A1 | 6/2014 | Causevic |
| 2015/0005660 | A1 | 1/2015 | Kraus |
| 2015/0073293 | A1 | 3/2015 | Kallstrand |
| 2016/0217267 | A1 | 7/2016 | Kraus |

OTHER PUBLICATIONS

Chandrasekaran, B., et al. (2010). The scalp-recorded brainstem response to speech: Neural origins and plasticity. Psychophysiology, 47, 236-246.
Coffey, E. B., et al. (2016). Cortical contributions to the auditory frequency-following response revealed by MEG. Nature Communications, 7.
Dhar, S., et al. "Exploring the relationship between physiological measures of cochlear and brainstem function." Clinical Neurophysiology 120.5 (2009): 959-966.
Folmer, R. L., et al. "Electrophysiological assessments of cognition and sensory processing in TBI: applications for diagnosis, prognosis and rehabilitation." International Journal of Psychophysiology 82.1 (2011): 4-15.
Ganes, T., et al. (1988). EEG and evoked potentials in comatose patients with severe brain damage. Electroencephalography and Clinical Neurophysiology, 69(1), 6-13.
Gosselin, N., et al. "Evaluating the cognitive consequences of mild traumatic brain injury and concussion by using electrophysiology." Neurosurgical focus 33.6 (2012): E7.
Internatonal Searching Authority. International Search Report and Written Opinion for application PCT/US2018/047881. Mailed on Oct. 25, 2018.
Johnson, K. L., et al. "Auditory brainstem correlates of perceptual timing deficits." Journal of cognitive neuroscience 19.3 (2007): 376-385.
Johnson, K. L., et al. "Brainstem encoding of voiced consonant-vowel stop syllables." Clinical Neurophysiology 119.11 (2008): 2623-2635.
Johnson, K. L., et al. "Developmental plasticity in the human auditory brainstem." Journal of Neuroscience 28.15 (2008): 4000-4007.
Kane, N. M., et al. "Event-related potentials—neurophysiological tools for predicting emergence and early outcome from traumatic coma." Intensive Care Medicine 22.1 (1996): 39-46.
Kraus, N., et al. "The neural legacy of a single concussion." Neuroscience letters 646 (2017): 21-23.
Kraus, N., et al. (2015). Unraveling the Biology of Auditory Learning: A Cognitive-Sensorimotor-Reward Framework. Trends in cognitive sciences, 19(11), 642-654.
Kraus, N., et al. (2016). Auditory biological marker of concussion in children. Scientific Reports, 97(12), e11.
Kraus, N., et al. (2016). Making sense of sound: A biological marker for concussion. American Congress of Rehabilitation Medicine Annual Conference, Chicago, IL.
Munjal, S. K., et al. (2010). Relationship between severity of traumatic brain injury (TBI) and extent of auditory dysfunction. Brain Injury, 24(3), 525-532.
Munjal, S. K., et al.. "Audiological deficits after closed head injury." Journal of Trauma and Acute Care Surgery 68.1 (2010): 13-18.
Musiek, F. E., et al. (2004). Assessment and remediation of an auditory processing disorder associated with head trauma. Journal of the American Academy of Audiology, 15(2), 117-132.
Oline, S. N., et al. (2016). Tonotopic optimization for temporal processing in the cochlear nucleus. Journal of Neuroscience, 36(32), 8500-8515.
Owens, S. (2017). Hearing Test May Detect Concussion in Kids. Neurology Now. Jan. 9, 2017 at http://journals.lww.com/neurologynow/blog/breakingnews/pages/post.aspx?PostID=421.
Russo, N., et al. "Brainstem responses to speech syllables." Clinical Neurophysiology 115.9 (2004): 2021-2030.
Skoe, E., et al. "Stability and plasticity of auditory brainstem function across the lifespan." Cerebral Cortex 25.6 (2015): 1415-1426.
Skoe, E., et al. (2010). Auditory brain stem response to complex sounds: A tutorial. Ear and Hearing, 31(3), 302-324.
Turgeon, C., et al. (2011). Auditory processing after sport-related concussions. Ear and Hearing, 32(5), 667-670.
Vander Werff, K. R. , et al. (2017). Brainstem evoked potential indices of subcortical auditory processing after mild traumatic brain injury. Ear and Hearing, 38(4), e200-e214.
Wehr, M., et al. (2003). Balanced inhibition underlies tuning and sharpens spike timing in auditory cortex. Nature, 426 (6965), 442.
White-Schwoch, T., et al. "Auditory-neurophysiological responses to speech during early childhood: Effects of background noise." Hearing research 328 (2015): 34-47.
Williamson, T. L. (2014). Brainstem Auditory Evoked Potentials and Network Dysfunction in Mild Traumatic Brain Injury. Yale Medicine Thesis Digital Library.

* cited by examiner

SYSTEMS AND METHODS FOR THE ACUTE EVALUATION OF TRAUMATIC BRAIN INJURIES

CROSS-REFERENCE STATEMENT

The present application is the U.S. national stage entry of international application PCT/US2018/047881, filed Aug. 24, 2018, which claims the benefit of U.S. Provisional Application 62/549,788, filed Aug. 24, 2017, the contents of which are incorporated herein by reference in their entireties.

FIELD OF THE INVENTION

The present disclosure provides methods for identifying non-penetrating brain injury in a subject in the acute injury stage, as well as methods for classifying a subject that received a hit to the body that transmitted an impulsive force to the brain as either having a non-penetrating brain injury or not, by analyzing one or more components of frequency-following response (FFR) following administration of an acoustic stimulus to the subject during the acute injury stage. In addition, the present disclosure provides methods for assessing a subject's recovery from a non-penetrating brain injury. Also disclosed herein are processes and systems for automatically generating acoustic stimuli and processing brain response data to identify non-penetrating brain injuries in subjects.

The present disclosure provides methods for identifying non-penetrating brain injury in a subject in the acute injury stage, as well as methods for classifying a subject that received a hit to the body that transmitted an impulsive force to the brain as either having a non-penetrating brain injury or not, by analyzing one or more components of frequency-following response (FFR) following administration of an acoustic stimulus to the subject during the acute injury stage. In addition, the present disclosure provides methods for assessing a subject's recovery from a non-penetrating brain injury. Also disclosed herein are processes and systems for automatically generating acoustic stimuli and processing brain response data to identify non-penetrating brain injuries in subjects.

BACKGROUND

Non-penetrating brain injuries carry devastating potential for cognitive, neurologic, and socioemotional disease, but no current objective approach reliably identifies this type of brain injury or its severity. For example, the current standard for concussion diagnosis is largely subjective in that it relies on accurate symptom reporting by the patient. Thus, there are ongoing efforts to identify objective markers to assist in diagnosing a concussion and predicting recovery.

One area of focus is on cerebrospinal fluid- and blood-based biomarkers that test for sequelae of neural injury. However, these biomarkers are invasive and may not extend to milder forms of non-penetrating brain injury, such as concussions. A second area tries to adopt neuroimaging techniques, such as diffusion tensor imaging and functional magnetic resonance imaging, to detect concussions. However, these approaches rely on expensive equipment and contradictory results are often reported: for example, both increases and decreases in white matter volume have been associated with mild traumatic brain injury. Visual, auditory, and somatosensory evoked potentials have all been explored in individuals following head injury, but contradictory findings have been reported. (Folmer, et al. *Int. J. Psychophysiol.* 82, 4-15 (2011); Munjal, et al. *J. Trauma Acute Care Surg.* 68, 13-18 (2010); Gosselin, N. et al. *Neurosurg. Focus* 33, E7 (2012)) Overall, current neuroimaging and electrophysiological approaches for various forms of non-penetrating brain injury show group differences but overlap between groups potentially thwarts evaluation of individual differences. The limitations of the aforementioned approaches necessitate a fresh methodology that has granularity into the biological minutiae of sound processing, and one that reliably indicates individual differences.

BRIEF DESCRIPTION OF THE FIGURES

The accompanying figures, which are incorporated herein and constitute part of this specification, illustrate non-limiting and non-exhaustive embodiments of the present disclosure, and, together with the description provided herein, serve to explain various features of the invention.

FIG. 1A is a graph showing grand average waveforms of the click-ABR at preseason baseline (solid line) and 24-48 hours post-concussion (dashed line). FIG. 1B provides graphs showing mean+1 standard error for peak I, III, and V latencies. While peak I latency is not affected, peaks III and V are both delayed following a concussion. FIG. 1C provides graphs showing a zoom-in of the click V for individual student-athletes at preseason (solid lines) and post-concussion (dashed lines).

FIG. 2A is a graph showing grand average waveforms of the FFR at preseason baseline (solid line) and 24-48 hours post-concussion (dashed line). FIG. 2B provides graphs showing mean+1 standard error for V, A, D, E, F, and O latencies. The onset peaks V and A are delayed following a concussion while the other peaks show no effect. FIG. 2C provides graphs showing a zoom-in of the FFR onset for individual student-athletes at preseason (solid lines) and post-concussion (dashed lines). The delays in V and A latency are evident across student-athletes.

FIG. 3A is a graph showing grand average waveforms of the F0-maximized FFR at preseason baseline (solid line) and 24-48 hours post-concussion (dashed line). The same data is shown in FIG. 2A. FIG. 3B is a graph showing grand average waveforms of the F1-maximized FFR at preseason baseline (solid line) and 24-48 hours post-concussion (dashed line). FIG. 3C is a graph showing mean+1 standard error magnitude for the F0-maximized responses. FIG. 3D is a graph showing mean+1 standard error magnitude for the F1-maximized responses. The F1-maximized response is smaller following concussion. FIG. 3E is a graph showing mean+1 standard error for the consistency of the F0-maximized responses (FIG. 3C). FIG. 3F is a graph showing mean+1 standard error for the consistency of the F1-maximized responses (FIG. 3D). The F0-maximized response tended to be less consistent following concussion.

FIG. 4A is a graph showing grand average spectra of the F0-maximized FFR at preseason baseline (solid line) and 24-48 hours post-concussion (dashed line). FIG. 4B provides graphs showing a zoom-in of the F0 for individual student-athletes at preseason (solid lines) and post-concussion (dashed lines). Analyses were run centered on an individual's maximum F0 encoding at preseason (rectangle).

FIG. 4C is a graph showing mean+1 standard error F0 amplitudes. The F0 shows a decline following a concussion.

FIG. 5A is a graph showing grand average spectra of the F1-maximized FFR at preseason baseline (solid line) and 24-48 hours post-concussion (dashed line). FIG. 5B provides graphs showing a zoom-in of the F1 for individual student-athletes at preseason (solid lines) and post-concussion (dashed lines). Analyses were run centered on an individual's maximum F1 encoding at preseason (rectangle). FIG. 5C is a graph showing mean+1 standard error F1 amplitudes. The F1 shows a decline following a concussion.

FIG. 6A is a graph showing the direction of change summed across each measure to provide a composite overview of changes in auditory processing following a concussion. For this, a delay or magnitude decrease was assigned a −1, no change a 0, and earlier or larger responses post-concussion were given a value of 1. These values were summed across the 15 measures. Thus, a negative value indicates that the majority of changes were in the direction of poorer processing, a zero would mean there were no changes in the response measured post-concussion compared to preseason and a positive response indicates an improvement in the response post-concussion. FIG. 6B provides graphs showing percent change from preseason to post-concussion on click-ABR latencies. A negative percent change reflects delayed latencies post-concussion. FIG. 6C provides graphs showing percent change from preseason to post-concussion on FFR measures. A negative percent change reflects poorer auditory processing post-concussion.

SUMMARY

Figure 1A:
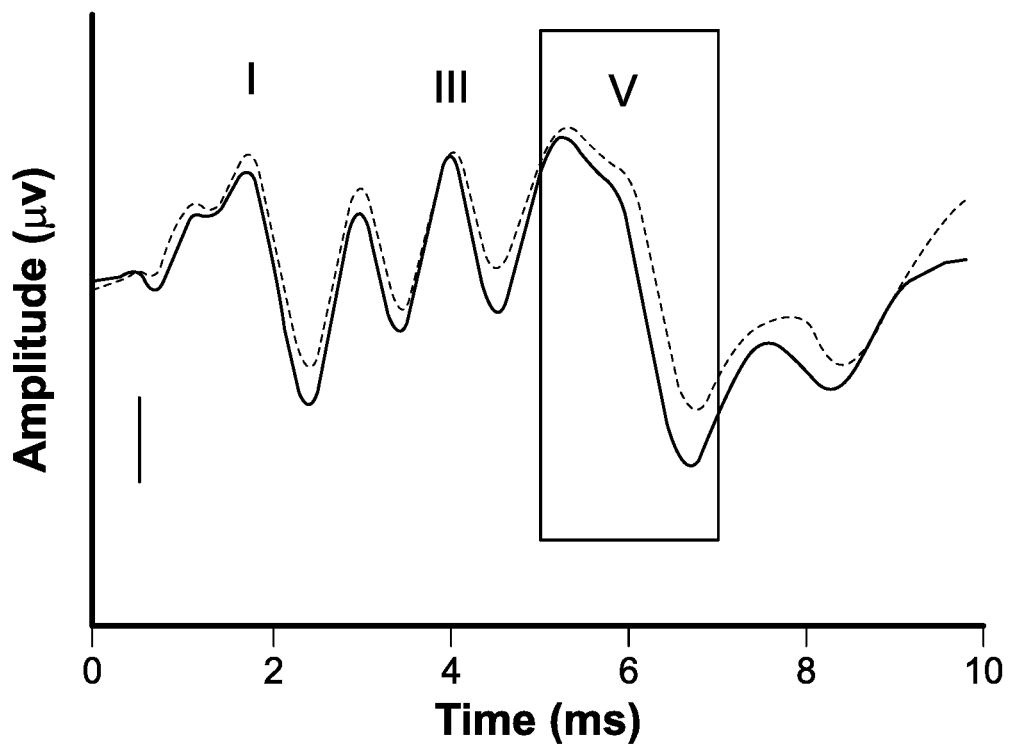
FIG. 1A-C illustrate that click-Auditory Brainstem Response (ABR) latency is affected by concussion.

In one aspect, the disclosed technology relates to a method of identifying a non-penetrating brain injury in a subject that has experienced brain injury, the method including: (a) fitting the subject with electrodes to measure voltage potentials generated from the subject's brain; (b) administering to the subject an acoustic stimulus including a complex sound; (c) recording voltage potentials from the subject's brain for at least the duration of the acoustic stimulus; (d) analyzing the voltage potentials to determine at least one component of the brain response to the acoustic stimulus; and (e) identifying the subject as having a non-penetrating brain injury if a value for at least one component of the brain response is anomalous; wherein the at least one component of the brain response is fundamental frequency ($F_0$), neural timing of a sustained response peak, response amplitude over a time window that includes some or all of the complex sound, or stimulus-response correlation over a time window that encompasses some or all of the complex sound. In one embodiment, the complex sound includes a consonant and a consonant-to-vowel transition. In another embodiment, the consonant is an obstruent stop consonant. In another embodiment, the consonant-to-vowel transition includes a low, back vowel.

In another embodiment, the complex sound includes a speech sound or a non-speech vocal sound. In another embodiment, the time window includes at least one formant. In another embodiment, the time window includes at least two formants. In another embodiment, the time window includes an unvoiced consonant release and/or a transient component corresponding to onset of voicing. In another embodiment, the speech sound includes at least one syllable selected from /da/, /pa/, /ka/, /ta/, /ba/, and /ga/. In another embodiment, the at least one component of the brain response includes neural timing of a sustained response peak. In another embodiment, the at least one component of the brain response includes response amplitude over a time window that includes some or all of the complex sound. In another embodiment, the at least one component of the brain response includes stimulus-response correlation over a time window that includes some or all of the complex sound, and the stimulus-response correlation is calculated in the time domain. In another embodiment, the at least one component of the brain response includes stimulus-response correlation over a time window that includes some or all of the complex sound, and the stimulus-response correlation is calculated in the frequency domain. In another embodiment, the at least one component of the brain response includes $F_0$ amplitude, F0 phase consistency, $F_0$ sharpness, $F_0$ frequency error, pitch tracking, or a combination thereof. In another embodiment, the at least one component of the brain response includes $F_0$ amplitude.

In another embodiment, step (e) includes identifying the subject as having a non-penetrating brain injury if values for at least two components of the brain response are anomalous. In another embodiment, the at least two components of the brain response are $F_0$ and stimulus-response correlation over a time window that encompasses the complex sound. In another embodiment, the subject also shows an anomalous Auditory Brainstem Response (ABR). In another embodiment, step (e) is performed within at least one of 12, 24, or 48 hours after the subject experienced the brain injury. In another embodiment, the method further includes administering to the subject a second acoustic stimulus including a click; and analyzing the subject's click-ABR.

In another aspect, the disclosed technology relates to a method for assessing a subject's recovery from a non-penetrating brain injury, the method including: in response to a brain injury of the subject, performing an acute evaluation of the subject's brain response to an acoustic stimulus by: fitting the subject with electrodes to measure voltage potentials generated from the subject's brain; administering to the subject an acoustic stimulus including a complex sound; recording voltage potentials from the subject's brain for at least the duration of the acoustic stimulus; analyzing the voltage potentials to determine at least one component of the brain response to the acoustic stimulus; and identifying a value for at least one component of the brain response that is anomalous; wherein the at least one component of the brain response is fundamental frequency ($F_0$), neural timing of a sustained response peak, response amplitude over a time window that includes some or all of the complex sound, and stimulus-response correlation over a time window that encompasses some or all of the complex sound; re-testing the subject's brain response to the acoustic stimulus at a later time by repeating steps a(i) to a(iv), and then identifying a value for the at least one component of the brain response that was anomalous in step (a)(v) ("the re-test value"); and calculating the difference between the anomalous value and the re-test value; wherein the subject is determined to be recovering from the non-penetrating brain injury if there is a change in the re-test value that is greater than would be expected by chance, and the direction of the change indicates an improvement in the component of the brain response; and wherein the subject is determined to not be recovering from the non-penetrating brain injury if (a) there is not a change in the re-test value that is greater than would be expected by chance, and the direction of the change indicates an improvement in the component of the brain response, or (b) when there is a change in the re-test value that is greater than would be expected by chance, and the direction of the change indicates a deterioration in the component of the brain response.

In another aspect, the disclosed technology relates to a system for identifying a brain injury, the system including a computing device including at least one processor configured to: receive an indication of a brain injury of a subject; in response to the indication, immediately perform an evaluation of the subject's brain response to an acoustic stimulus by: generating an acoustic stimulus including a complex sound; obtaining voltage potential data from a brain response corresponding to an auditory pathway of a subject, wherein the voltage potential data is obtained during presentation of the acoustic stimulus to the subject; analyzing the voltage potential data to determine at least one component of the brain response; and generating and storing, in a memory in operable communication with the at least one processor, an indication of a non-penetrating brain injury when a first value for at least one component of the brain response is anomalous; wherein the at least one component of the brain response is fundamental frequency ($F_0$), neural timing of a sustained response peak, response amplitude over a time window that includes some or all of the complex sound, or stimulus-response correlation over a time window that encompasses some or all of the complex sound. In one embodiment, the at least one processor is further configured to generate and store, in the memory, an indication of no non-penetrating brain injury when a second value for at least one other component of the brain response is not anomalous. In another embodiment, the at least one component of the brain response includes $F_0$ amplitude, $F_0$ phase consistency, $F_0$ sharpness, $F_0$ frequency error, pitch tracking, or a combination thereof. In another embodiment, the complex sound includes a speech sound or a non-speech vocal sound. In another embodiment, the speech sound includes at least one syllable selected from /da/, /pa/, /ka/, /ta/, /ba/, and /ga/. In another embodiment, the voltage potential data is obtained from at least one electrode fit to the subject, the at least one electrode in operable communication with the computing device.

Additionally, one aspect of the invention encompasses methods for identifying non-penetrating brain injury in a subject, the method comprising analyzing one or more components of a subject's frequency following response (FFR) to an acoustic stimulus comprising a complex sound; and identifying the subject as having a non-penetrating brain injury when a value for at least one component of the brain response is anomalous. The method may further comprise analyzing one or more transient responses to an acoustic stimulus.

Another aspect of the invention encompasses methods for identifying non-penetrating brain injury in a subject, the method comprising analyzing one or more components of a subject's frequency following response (FFR) to an acoustic stimulus comprising a complex sound, and identifying the subject as having a non-penetrating brain injury when a value for at least one component of the brain response is anomalous, wherein the component(s) are selected from fundamental frequency ($F_0$) and/or harmonics, neural timing of a response peak, response amplitude over a time window that encompasses some or all of a sustained response, and stimulus-response correlation over a time window that encompasses some or all of a sustained response. The method may further comprise analyzing one or more transient responses to an acoustic stimulus.

Another aspect of the invention encompasses methods for identifying non-penetrating brain injury in a subject, the method comprising (a) fitting the subject with electrodes to measure voltage potentials generated from the subject's brain; (b) administering to the subject an acoustic stimulus, wherein the acoustic stimulus is comprised of a complex sound, and the complex sound comprises a consonant, a consonant-to-vowel transition, and optionally a vowel; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous; wherein the component(s) are selected from fundamental frequency ($F_0$), neural timing of a sustained response peak, response amplitude over a time window that comprises some or all of the consonant-vowel transition, and stimulus-response correlation over a time window that encompasses some or all of the consonant-vowel transition.

Another aspect of the invention encompasses methods for classifying a subject that received a hit to the body that transmitted an impulsive force to the brain as either having a non-penetrating brain injury or not, the method comprising analyzing one or more components of a subject's frequency following response (FFR) to an acoustic stimulus comprising a complex sound; and classifying the subject as having a non-penetrating brain injury when a value for at least one component of the brain response is anomalous. The method may further comprise analyzing one or more transient responses to an acoustic stimulus.

Another aspect of the invention encompasses methods for classifying a subject that received a hit to the body that transmitted an impulsive force to the brain as either having a non-penetrating brain injury or not, the method comprising analyzing one or more components of a subject's frequency following response (FFR) to an acoustic stimulus comprising a complex sound; and classifying the subject as having a non-penetrating brain injury when a value for at least one component of the brain response is anomalous, wherein the component(s) are selected from fundamental frequency ($F_0$) and/or harmonics, neural timing of a response peak, response amplitude over a time window that encompasses some or all of a sustained response, and stimulus-response correlation over a time window that encompasses some or all of a sustained response. The method may further comprise analyzing one or more transient responses to an acoustic stimulus.

Another aspect of the invention encompasses methods for classifying a subject that received a hit to the body that transmitted an impulsive force to the brain, the method comprising (a) fitting the subject with electrodes to measure voltage potentials generated from the subject's brain; (b) administering to the subject an acoustic stimulus, wherein the acoustic stimulus is comprised of a complex sound, and the complex sound comprises a consonant, a consonant-to-vowel transition, and optionally a vowel; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous; wherein the component(s) are selected from fundamental frequency ($F_0$), neural timing of a sustained response peak, response amplitude over a time window that comprises some or all of a consonant-vowel transition, and stimulus-response correlation over a time window that encompasses some or all of a consonant-vowel transition.

Another aspect of the invention encompasses method for assessing a change in a non-penetrating brain injury, the method comprises (a) analyzing one or more components of a subject's FFR to an acoustic stimulus comprising a complex sound; (b) re-testing the subject's FFR to the acoustic stimulus at a later time; and determining any differences in the one or more components from step (a). If the absolute value of the difference is greater than would be expected by chance, there is a change in the non-penetrating brain injury.

Another aspect of the invention encompasses methods for assessing a subject's recovery from a non-penetrating brain injury, the method comprising (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) are selected from fundamental frequency ($F_0$) and/or harmonics, neural timing of a response peak, response amplitude over a time window that encompasses some or all of a sustained response, and stimulus-response correlation over a time window that encompasses some or all of a sustained response. If the absolute value of the difference is greater than would be expected by chance, there is a change in the non-penetrating brain injury. The direction of the change indicates improvement or worsening/deterioration.

Another aspect of the invention encompasses method for assessing a subject's recovery from a non-penetrating brain injury, the method comprises two steps. The first step comprises (a) testing the subject's brain response to an acoustic stimulus by: (i) fitting the subject with electrodes to measure voltage potentials generated from the subject's brain; (ii) administering to the subject an acoustic stimulus, wherein the acoustic stimulus is comprised of a complex sound, and the complex sound comprises a consonant, a consonant-to-vowel transition, and optionally a vowel; (iii) recording voltage potentials from the subject's brain for at least the duration of the acoustic stimulus; (iv) analyzing the voltage potentials to determine one or more components of the brain response; and (v) identifying a value for at least one component of the brain response that is anomalous; wherein the component(s) are selected from fundamental frequency ($F_0$), neural timing of a sustained response peak, response amplitude over a time window that comprises some or all of the consonant-vowel transition, and stimulus-response correlation over a time window that encompasses some or all of the consonant-vowel transition. The second step comprises (b) re-testing the subject's brain response to the acoustic stimulus at a later time by repeating steps a(i) to a(iv), and identifying the value for the one or more components that were anomalous in step (a)(v) ("the re-test value"); and (c) calculating the difference between the re-test value and the anomalous value. The subject is determined to be recovering from the non-penetrating brain injury when there is a change in the re-test value that is greater than would be expected by chance, and the direction of the change indicates an improvement in the component of the brain response. The subject is determined to not be recovering from the non-penetrating brain injury when (a) there is not a change in the re-test value that is greater than would be expected by chance, or (b) when there is a change in the re-test value that is greater than would be expected by chance, and the direction of the change indicates a deterioration in the component of the brain response.

Other features and aspects of the invention are described in more detail herein.

DETAILED DESCRIPTION

Applicants have discovered that a traumatic brain injury (e.g., a concussion or non-penetrating brain injury) can be identified in a subject by analyzing one or more components of frequency-following response (FFR) following administration of an acoustic stimulus to the subject. The FFR reflects sustained neural activity over a population of neural elements.

Accordingly, aspects of the present disclosure involve systems and methods for the acute evaluation (e.g., immediately post injury and/or during recovery thereafter) of a non-penetrating brain injury using the FFR response to an acoustic stimulus. Generally speaking, "acute evaluation" refers to a quantification and/or qualification of the time required to evaluate a brain injury as non-penetrating. Thus, in one example, "acute evaluation" may refer to an immediate evaluation of a subject after a brain injury has occurred. In another example, an acute evaluation may involve an evaluation performed up to six (6), twelve (12), twenty-four (24), or forty-eight (48) hours after the brain injury, while an evaluation occurring one hundred sixty eight (168) hours or later after the brain injury would exclude an "acute evaluation" of the brain injury. Thus, the disclosed system analyzes one or more components of the FFR that potentially indicate the presence of a traumatic brain injury in the acute injury stage (e.g., 6-48 hours post injury). Various aspects of the FFR are described in further detail below.

As used herein, the term "non-penetrating brain injury" refers to a type of brain injury caused by an indirect or a direct hit to a subject's body that transmits an impulsive force to the subject's brain. The injury may occur after a single blow or after repeated blows. The indirect or direct hit can be to the head, the neck, or elsewhere on the body. Non-limiting examples of indirect hits to the body that may result in non-penetrating brain injury include whiplash, a blast wave from an explosion, or other acceleration or deceleration forces on the body. Non-limiting examples of direct hits to the body that may result in non-penetrating brain injury include head-to-head contact, head-to-other body part (hand, foot, leg, elbow, shoulder, etc.) contact, head-to-ground contact, head-to-object contact (sports equipment (e.g. ball, puck, stick, sword, surfboard, ski, etc.), moving objects, stationary objects, etc.), etc. Various types of "non-penetrating brain injury" include, but are not limited to, concussions and traumatic brain injury (e.g., mild, moderate, severe, etc.). A subject that has a non-penetrating brain injury may or may not have detectable signs of physical brain injury or symptoms commonly associated therewith. The term "non-penetrating brain injury" excludes penetrating brain injuries. A penetrating brain injury is a head injury in which the dura mater is breached. The term "non-penetrating brain injury" also excludes biological insults to the brain, e.g., protein aggregate diseases (e.g., Alzheimer's disease, Parkinson's disease, Huntington's disease, amyotrophic lateral sclerosis, prion diseases, etc.), demyelinating diseases (e.g., Multiple Sclerosis, Devic's disease, Vitamin B12 deficiency, etc.) bacterial infections, encephalitis, tumors, etc.

A subject of this disclosure may be a human or an animal. Suitable subjects include a human, a livestock animal, a companion animal, a laboratory animal, and a zoological animal. In one embodiment, the subject is human. Also contemplated are subjects that have an increased risk of non-penetrating brain injury, including, but not limited to, human subjects that are, or were, athletes (amateur or professional), soldiers, victims of physical abuse, involved in a motor vehicle collision, or involved in a bicycle or pedestrian accident, as well as subjects that had a previous non-penetrating brain injury. Methods of this disclosure may not be suitable for subjects with deafness or known neurological conditions which may have an impact on FFR (e.g. multiple sclerosis, epilepsy.)

The present disclosure provides methods for identifying non-penetrating brain injury in an asymptomatic or a symptomatic subject, as well as methods for assessing a subject's recovery from a non-penetrating brain injury. Also disclosed herein are processes and systems for automatically generating acoustic stimuli and processing brain response data to identify non-penetrating brain injuries in subjects. Various aspects of this disclosure are described in further detail below.

I. Evoking a Brain Response to a Complex Sound

A brain response to sound is evoked by presenting an acoustic stimulus comprising a complex sound to a subject. The brain's response to the acoustic stimulus can be recorded in a number of different ways. For instance, the brain's response may be measured using electrodes that pick up electrical potentials generated by populations of neurons in the brain. An "acoustic stimulus," as used herein, refers to an input of one or more sounds. A "complex sound" refers to a sound comprised of two or more frequencies. The term "brain response" refers to a recorded measurement of the voltage potentials from a subject's brain evoked by an acoustic stimulus comprising a complex sound. An acoustic stimulus may be presented once or multiple times. Each presentation of the same acoustic stimulus may be referred to as a "trial." In embodiments where an acoustic stimulus is presented multiple times, the temporal interval between the offset of one stimulus to the onset of another can vary such that there is no amount of time between the stimuli or various amounts of time are included. This interval is referred to as the interstimulus interval. A non-limiting example of a range for an interstimulus interval may be zero msec to about 80 msec.

(a) Acoustic Stimulus

An acoustic stimulus may include a complex sound and, optionally, background noise.

i. Complex Sound

A complex sound includes a sound comprised of two or more frequencies. The term "complex sound" includes amplitude, frequency, and/or phase modulated waves. An amplitude modulated wave is when the amplitude of a carrier wave, such as a sine wave, is altered by a modulating wave. For example, a 1000 Hz sine wave carrier could be modulated by a 300 Hz sine wave tone. These waves do not have to be tones. Similarly, a wave can also be modulated in frequency or phase. The term "complex sound" excludes simple sounds known in the art including, but not limited to, clicks and sinusoidal tones that are not modulated. A complex sound may be natural, synthetic, or a hybrid thereof. Minimally, a complex sound used in the methods of this disclosure should elicit a clear and reproducible brain response in healthy subjects. Synthetic or hybrid sounds are preferred because they offer precise control over the various aspects of sound but well-characterized audio files of natural sounds are suitable as well. Non-limiting examples of complex sounds include vocal sounds, environmental sounds, and musical sounds. Vocal sounds include, but are not limited to, a speech syllable, a word, and a non-speech vocal sound (e.g., a cry, a grunt, an animal sound, etc.). Musical sounds include, but are not limited to, a note played by an instrument, a consonant two-note interval played by an instrument, a dissonant two-note interval played by an instrument, and a musical chord. Environmental sounds include, but are not limited to, a rainfall sound, an ocean sound, a car horn, a train whistle, etc.

Complex sounds used in the present disclosure have aspects that maximize transient and sustained brain responses. In one aspect, a complex sound has one or more strong transient features. Transient features are brief and nonsustained, and evoke fast response peaks lasting fractions of a millisecond (i.e., a transient brain response). The relative strength of a transient feature refers to the timing and/or amplitude. The onset of sound and the offset of sound are common transient features of complex sound. The onset of sound is also referred to as "attack," which is the amount of time taken for the amplitude to reach its maximum level. The offset of sound is also referred to as "release," which is the final reduction in amplitude over time. A transient feature may also be an "amplitude burst," which is an abrupt change in the amplitude envelope of a complex sound. For example, a baby's cry can include multiple amplitude-bursts that produce a series of sharp, transient responses.

Among complex speech sounds, obstruent stop consonants (e.g., /d/, /p/, /k/, /t/, /b/, /g/, etc.) have faster and steeper onsets than affricate consonants (e.g., /tʃ/ and /dʒ//, etc.), which have faster and steeper onsets than fricative consonants (e.g., /z/, etc.), which have faster and steeper onsets than sonorant consonants (e.g. nasals, glides, and slides (e.g., /r/, /l/, etc.). Similarly, musical sounds have varying attack properties that depend on the instrument and how the instrument is played. For example, percussive instruments have fast, steep attacks, and bowed string instruments have comparatively smoother attacks; and a plucked string has a shorter rise time than a bowed string.

In another aspect, a complex sound has a fundamental frequency ($F_0$) in the range of about 50 Hz to about 500 Hz. Fundamental frequencies within this range elicit a strong (i.e., sustained), phase-locked brain response to the $F_0$ and its harmonics. Because phase-locking may become weaker with increasing frequency, a $F_0$ range of about 50 Hz to about 400 Hz may be preferred. Alternatively, the $F_0$ may range from about 80 Hz to about 400 Hz, or from about 80 Hz to about 300 Hz. In some embodiments, a complex sound may have an $F_0$ that is stable. In some embodiments, a complex sound may have an $F_0$ that changes over time. In other embodiments, the stimulus may be manipulated to remove the $F_0$ and only contain the harmonic integer frequencies of the $F_0$. In this instance, a listener still perceives a fundamental frequency that is approximated as the common denominator from the harmonics. For example, a harmonic series at 200, 300, 400, and 500 Hz would result in a perceived $F_0$ at 100 Hz, and there would be a brain response at 100 Hz.

In embodiments where the complex sound is a speech sound, voiced portion(s) of the sound provide the sustained features. Many, but not all, consonants sounds are unvoiced, meaning that the vocal cords are not in motion. In most languages, all vowels are voiced, meaning that the vocal cords are in motion. Thus, a "consonant-to-vowel transition" often involves a change, acoustically, from an unvoiced speech segment to a voiced speech segment. Non-limiting examples of a voiced portion of a sound include a consonant-to-vowel transition, a voiced consonant transition, or a steady-state vowel portion. Though non-speech vocal sounds from animals do not include consonants and vowel, they do contain voiced sounds (for those animals with vocal cords) and other sounds filtered by the vocal tract. As such, non-speech vocal sounds contain acoustic features that are substantially similar to a consonant-to-vowel transition in a speech sound.

The duration of a complex sound can vary. The minimum duration is at least one cycle of the complex sound's $F_0$. For example, the duration may be 1, 2, 3, 4, 5, 6, 7, 8, 9, 10 or more cycles of the complex sound's $F_0$. Musical timbre and vowel identity can be accurately determined from one to four cycles of the $F_0$, but pitch identification typically requires about four or more cycles. See, for example, Gray, G. W. (1942), *Speech Monographs*, 9, 75; or Robinson, K, (1995), *Music Perception*, 13, 1-15; or Robinson, K., & Patterson, R. D. (1995), *J Acoust Soc Am*, 98, 1858-1865.

Generally speaking, one factor limiting the duration of an acoustic stimulus is the feasibility of having a subject remain still for a long time. Thus, duration may need to be restricted to present the desired number of acoustic stimuli in a reasonable amount of time. In various embodiments, the duration may be about 10 msec, about 20 msec, about 30 msec, about 40 msec, about 50 msec, about 60 msec, about 70 msec, about 80 msec, about 90 msec, about 100 msec, or more.

When an acoustic stimulus has a complex sound that is a speech syllable, one strategy to limit duration is to use a consonant and a consonant-vowel (CV) transition without a steady-state vowel. See, for example, Russo et al. (2004), *Clin Neurophysiol*, 115, 2021-2030; Johnson, et al. (2007), *J Cogn Neurosci*, 19, 376-385; Johnson, et al. (2008), *J Neurosci*, 28, 4000-4007; Hornickel, et al. (2009), *Audiol Neurootol*, 14, 198-207; Banai, et al. (2009), *Cereb Cortex*, 19, 2699-2707; Dhar, et al. (2009), *Clin Neurophysiol*, 120, 959-966. Because each CV transition has a unique formant transition, the steady state vowel can be removed with little impact on the percept. Within this disclosure, speech syllables with a CV transition are identified by the consonant and the vowel, e.g., /da/, but this nomenclature is understood to include a consonant and a CV transition without a steady-state vowel.

ii. Background Noise

The term "background noise" refers to any sound that occurs at the same time as the sound of interest, e.g., the complex sound intentionally administered to a subject to elicit an auditory response. Non-limiting examples of "background noise" include white noise, pink noise, a murmur of voices, traffic, construction, etc.

iii. Stimulus Creation/Presentation

To elicit a brain response, an acoustic stimulus of the disclosure is created and then presented to a subject. In some embodiments, natural sounds are recorded and then presented, and artificial sounds are synthesized and then presented. Various aspects of presentation including stimulus intensity, monaural and binaural stimulation, left and right ear stimulation, stimulus polarity, stimulation rate, transducers, jitter in the stimulus presentation, and multiple stimulus conditions may be used. See, e.g., U.S. Pat. Nos. 8,014,853; 8,712,514; and 8,825,140, and U.S. 2016/0217267, each of which is hereby incorporated by reference in its entirety.

iv. Example Embodiments

In some embodiments, a complex sound comprises a sound such as an environmental sound, a musical sound, a speech sound, or a non-speech vocal sound. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec. In certain embodiments, the fundamental frequency ranges from about 130 Hz to about 350 Hz and/or the duration may be at least about 20 msec, at least about 30 msec, or at least about 40 msec. In certain embodiments, the fundamental frequency ranges from about 180 Hz to about 400 Hz and/or the duration may be at least about 20 msec, at least about 30 msec, or at least about 40 msec. In certain embodiments, the fundamental frequency ranges from about 230 Hz to about 450 Hz and/or the duration may be at least about 20 msec, at least about 30 msec, or at least about 40 msec. In certain embodiments, the fundamental frequency ranges from about 280 Hz to about 500 Hz and/or the duration may be at least about 20 msec, at least about 30 msec, or at least about 40 msec.

In other embodiments, a complex sound comprises a speech sound or a non-speech vocal sound. In other embodiments, a complex sound includes a speech sound or a non-speech vocal sound. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec. In certain embodiments, the speech sound includes a speech syllable, non-limiting examples of suitable speech syllables are listed in the table below.

| Speech Syllable | Examples | Publications |
|---|---|---|
| Vowels | | |
| Synthetic | /a/, /u/ | Krishnan, 2002 |
| Natural | /ɛ/, /i/, /V/, /a/, /ae/, /ʰ/, /u/ | Greenburg et al. 1980; Dajani et al. 2005, Aiken & Picton 2006, 2008 |
| Consonant-vowel syllables | | |
| Synthetic | /da/ | Cunningham et al. 2001; Plyler & Ananthanarayan 2001; King et al, 2002; Wible et al. 2004, 2005; Russo et al. 2004, 2005; Kraus & Nicol 2005; Johnson et al. 2007, 2008; Banal et al. 2005, 2009; Burne et al. 2009; Chandarasekaran et al. 2009; Parbery-Clark et al. 2009a |
| | /ba/ | Akhoun et al. 2008a, b |
| | ba-da-ga continuum | Plyler & Ananthanarayan 2001; Johnson et al. 2008; Hornickel et al. 2009b |
| Natural | Mandarin pitch contours | |
| | /yl/ | Krishnan et al. 2005; Xu et al. 2006 |
| | /ml/ | Wong et al. 2008; Song et al. 2008 |
| Hybrid | /ya/ with linearly rising and falling pitch contours | Russo et al. 2008 |

In another embodiment, a complex sound has a duration of at least about 10 msec and comprises a first sound that transitions directly to a second sound, wherein the first sound has an attack substantially similar to an obstruent consonant and the second sound has a minimum of two formants held steady for one period of F0, and the F0 ranges from about 50 Hz to about 500 Hz. In some embodiments, the complex sound is a musical sound. In other embodiments, the complex sound is an environmental sound. In other embodiments, the complex sound is a vocal sound.

In another embodiment, a complex sound comprises a speech syllable, the speech syllable comprising a consonant-vowel transition, a diphthong, a triphthong, or a linguistic pitch contour. The complex sound may or may not be a word. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec.

In another embodiment, a complex sound includes a speech syllable, the speech syllable comprising a consonant-vowel transition, a diphthong, or a linguistic pitch contour. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec.

In other embodiments, a complex sound comprises a consonant, a consonant-to-vowel transition, and optionally a vowel. The complex sound may or may not be a word. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec. Non-limiting examples include /da/, /po/, /chu/, /ki/, /yi/, and /mi/, and variations thereof where the consonants and vowels are substituted for other consonants and vowels that produce similar acoustic features.

In other embodiments, a complex sound includes a consonant, a consonant-to-vowel transition, and optionally a vowel. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec. Non-limiting examples include /da/, /po/, /chu/, /ki/, /yi/, and /mi/, and variations thereof where the consonants and vowels are substituted for other consonants and vowels that produce similar acoustic features.

In another embodiment, a complex sound has a duration of at least about 10 msec and comprises a first sound that transitions directly to a second sound, wherein the first sound is an obstruent consonant and the second sound has a minimum of two formants held steady for one period of $F_0$, and the $F_0$ ranges from about 50 Hz to about 500 Hz.

In another embodiment, a complex sound has a duration of at least about 10 msec and includes a first sound that transitions directly to a second sound, wherein the first sound is an obstruent consonant and the second sound has a minimum of two formants held steady for one period of $F_0$, and the $F_0$ ranges from about 50 Hz to about 500 Hz.

In other embodiments, a complex sound comprises a consonant, a consonant-to-vowel transition, and optionally a vowel, wherein the consonant is an obstruent stop consonant and the vowel is a low back vowel. A non-limiting example of this complex sound is /da/. The complex sound may or may not be a word. The complex sound has a fundamental frequency ($F_0$) that ranges from about 50 Hz to about 500 Hz, and duration of at least about 10 msec. In certain embodiments, the $F_0$ ranges from about 80 Hz to about 300

Hz and/or the duration may be at least about 20 msec, at least about 30 msec, or at least about 40 msec.

In other embodiments, a complex sound includes a consonant, a consonant-to-vowel transition, and optionally a vowel, wherein the consonant is an obstruent stop consonant and the vowel is a low back vowel. A non-limiting example of this complex sound is /da/. The complex sound has a fundamental frequency ($F_0$) that ranges from about 50 Hz to about 500 Hz, and duration of at least about 10 msec. In certain embodiments, the $F_0$ ranges from about 80 Hz to about 300 Hz and/or the duration may be at least about 20 msec, at least about 30 msec, or at least about 40 msec.

In other embodiments, a complex sound comprises a speech syllable selected from /da/, /pa/, /ka/, /ta/, /ba/, and /ga/. The complex sound may or may not be a word. The complex sound has a duration of at least about 10 msec. In certain embodiments, the duration may be at least about 20 msec, at least about 30 msec, or at least about 40 msec.

In other embodiments, a complex sound includes a speech syllable selected from /da/, /pa/, /ka/, /ta/, /ba/, and /ga/. The complex sound has a duration of at least about 10 msec. In certain embodiments, the duration may be at least about 20 msec, at least about 30 msec, or at least about 40 msec.

(b) Brain Response

Sound evokes a precise neural response in a subject's brain. In the present disclosure, a brain's response is measured using electrodes that pick up electrical potentials generated by populations of neurons in the brain. The term "brain response" refers to a recorded measurement of the voltage potentials from a subject's brain evoked by an acoustic stimulus comprising a complex sound. Various aspects relating to electrode placement, sampling rate, filtering, signal averaging, and minimizing artifacts can be determined. The table below provides a general recommendation for some of these aspects.

| Parameter | Recommendation | Rationale/Comments |
|---|---|---|
| Electrode placement | Vertical montage (active; Cz; reference; earlobe(s); ground; forehead) | For rostral brain stem recordings; a horizontal montage is used for recording from more peripheral structures |
| Sampling rate | 6000-20000 Hz | Better temporal precision with higher sampling rates |
| Filtering | Low-pass cutoff: 2000-3000 Hz High-pass cutoff: 30-100 Hz | More defined transient peaks Depends on spectral characteristics of stimulus |
| | If possible, collect FFR with open filters (1-3000 Hz) and band-pass filter off-line using digital filters | Digital filters minimize temporal phase shifts |
| Signal averaging | 2 or more subaverages of 2000-3000 sweeps | Determine response replicability Spectral-domain averaging will increase spectral estimates and require fewer sweeps |
| Averaging window | Begin 10-50 msec before stimulus onset | An adequate sample of the baseline is needed to determine whether a particular response peak is above the noise floor |
| | Extend 10-50 msec after stimulus onset | For running window analysis, the pre-stimulus time window should be greater than or equal to the duration of the analysis window Neural activity should return to baseline |
| Simultaneous FFR-cortical response recording | Only if large files can be accommodated and longer sessions are appropriate | |
| Minimizing artifacts | Passive collection protocol Electromagnetic shielded insert ear phones | Minimizes myogenic artifacts Minimize stimulus artifact |
| | Both stimulus polarities | Enables adding of responses to minimize both stimulus artifact and cochlear microphonic |
| | Use electrically shielded test booth | Minimizes electrical artifact |
| | Project movie into test booth Artifact rejection criterion: >20 µv | Exclude trials exceeding typical neural response size; criterion depends on high-pass filter setting |

FFRs, auditory brain stem responses to complex sounds.

Generally speaking, a brain response includes a plurality of positive and negative amplitude deflections, referred to as "response peaks." A brain response is initially recorded as a series of voltages over time (referred to as the time domain response), which can be converted to a series of voltages over frequency (referred to as the frequency, or spectral, domain response). A brain response to complex sound contains multiple, independent, components in both the time domain and the frequency domain. In the context of identifying non-penetrating brain injury, measurements of these components can be meaningful individually or in aggregate.

In the time domain, response peaks are generally classified as either a transient response peak or a sustained response peak. Similarly, regions of the time domain containing transient response peaks or sustained response peaks may be classified as a transient region or a sustained region, respectively. This terminology reflects a brain response to either a transient feature or a sustained feature of a complex sound. The number and morphology of peaks in a brain response varies based on the complex sound used. All sounds generate a response peak corresponding to the onset of the sound (i.e., an onset peak), though there is typically a lag of about 6 to about 10 msec between when a sound begins and the onset peak. In some instances, a brain response to the onset of sound is a biphasic peak (e.g., positive then negative, or negative then positive), rather than a single peak. The positive/negative pair may be referred to as an "onset response." The lag of about 6 to about 10 msec between the onset of sound and an onset peak is referred to as a "neural transmission delay" or a "neural onset delay." An onset peak is a transient response. Additional transient responses may also be present including, but not limited to, a brain response to the onset of an amplitude burst and a brain response to the offset of sound. Complex sounds also generate response peaks that are time-locked to the temporal structure of the eliciting sound. These response peaks are sustained features of a brain response and reflect synchronous, population-wide neural phase locking. Sustained brain responses are often called frequency following responses (FFR). In embodiments where an acoustic stimulus includes an interstimulus interval, the brain response will contain an interstimulus region.

The response peaks for some complex sounds are described below. For example, a 40 msec /da/ syllable produces six stereotyped peaks: peak V, which is a positive amplitude deflection corresponding to the onset of the stimulus and occurring about 6 msec to about 10 msec after stimulus onset; peak A, which is a negative amplitude deflection immediately following peak A; peaks D, E, and F, which are negative amplitude deflections corresponding to the voicing of the speech sound and occurring at about 22 msec, about 32 msec, and about 42 msec respectively; and peak 0, which is a negative amplitude deflection following the offset of the sound, occurring at about 50 msec. A 170 msec /da/ syllable is described in White-Schwoch et al. *Hearing Research* 2015, 325:34-47, and descriptions of /ba/ and /ga/ sounds may be found in Johnson et al. Clinical Neuropsychology 119:2623-2635. The above description is not limiting.

Neural phase-locking is also evident in the frequency domain, where the brain response follows the periodicity of the eliciting sound. As such, the $F_0$ and harmonics (i.e., integer multiples of $F_0$) of the eliciting sound are reflected in the brain response. Typically all harmonics present in an acoustic stimulus, up to the frequency limits that the brain is able to produce, are present in a brain response. Though, generally speaking, phase locking is more robust when there is less spectral flux (i.e., change in harmonics over time). Non-linearities of the auditory system will often result in additional harmonic peaks in the response beyond those present in the stimulus.

When an acoustic stimulus contains a speech sound or a non-speech vocal sound, certain harmonics are of particular importance phonetically. These harmonics are called "formants." Formants are harmonics that are larger in amplitude than surrounding harmonics (both in the eliciting sound and the response). Each speech sound can be uniquely identified by its characteristic formant pattern, with the first two or three formants being sufficient for identifying most speech sounds. For example, the /a/ sound will typically have a local peak at around 700-750 Hz regardless of the pitch ($F_0$) of the utterance. This is the first formant of /a/. The vowel /i/, on the other hand, will have a first formant in the 250-300 Hz range.

In contrast to speech, which is dominated by fast spectrotemporal transitions, music has more prevailing temporal and spectral elements, slower transitions, and finer frequency spacing. In the same way that speech sounds are characterized by unique formant configurations, instruments also have characteristic harmonic structures that impart timbre. Specifically, the timbre of a musical sound is determined by the rise time of the attack, the spectral flux, and the spectral centroid (i.e., the distribution of the harmonics). The clarinet, for example, has a harmonic structure dominated by lower frequency odd harmonics (the even harmonics have been attenuated). The flute, saxophone, trombone, and tuba, which are all characterized by strong odd and even harmonics, can be differentiated by the distribution of the harmonics (e.g., the energy of the tuba is concentrated in the lower harmonics)

Certain aspects of spectral and temporal components of a brain response to complex sound are described below.

i. Brain Response Fundamental Frequency ($F_0$)

One aspect of a brain response to a complex sound is the extent to which the brain response reflects the $F_0$ of the stimulus. As described elsewhere, $F_0$ is a defined parameter based on the acoustics of the eliciting sound. Various aspects of $F_0$ may be analyzed including but not limited to, $F_0$ amplitude, $F_0$ sharpness, $F_0$ phase consistency, or pitch tracking.

To calculate response $F_0$, the time domain response must be converted to a frequency domain response. Suitable methods for achieving this include, but are not limited to, fast Fourier transformation (FFT). FFT may be computed on all or a portion of the time range collected. The time range over which the FFT is calculated may vary provided the range: (1) accounts for a neural transmission delay, which is typically about 6-10 msec or may alternatively be determined by the timing of the first amplitude deflection in the brain response; (2) does not extend beyond the end of the brain response, which is typically about 6-10 msec longer than the length of the stimulus plus onset delay; and (3) includes one cycle of the period of the complex sound's $F_0$. For example, at least a 10 msec time period is used to calculate the FFT for a complex sound with an $F_0$ of 100 Hz (period is the inverse of frequency). The FFT may be generated using any standard windowing approach including, but not limited to, a Hanning window, a Hamming window, a Blackman window, a cosine window, a Nuttall window, a Blackman-Harris window, and a flat-top window. The length of the ramp in computing the FFT can range from 1 msec up to half the length of the time window over which the FFT is calculated. For example, if the FFT is calculated over a 100 msec window, ramp times could include 1 msec, 2 msec, 3 msec, 4 msec, 5 msec, up to 50 msec. The arithmetic mean of the amplitude of the spectrum that corresponds to the $F_0$ of the complex sound may also be calculated.

Alternatively, a response $F_0$ may be determined by autocorrelation. An autocorrelation method is a procedure that time-shifts a waveform (A) with respect to a copy of itself (N) and correlates A to A' at many such time shifts. For example A(1:10) (i.e., points 1 to 10 of waveform A), is correlated to A'(1:10), then A(1:10) is correlated to A'(2:11), then A'(3:12), etc. The reverse shift also is evaluated, such that A(1:10) is correlated with A'(−1:9) and A'(−2:8), etc. Each time shift is considered a "lag," such that A(1:10) vs A'(1:10) has a lag of 0; A(1:10) vs A'(2:11) has a lag of 1, etc. The fundamental frequency of the waveform A will occur at $1/L_{max}$ Hz, where $L_{max}$ is defined as the lag (in sec) at which the maximum correlation is achieved. The definition of $L_{max}$ is further refined to exclude a lag of 0 which is the largest correlation. In practice, if there is a known frequency range of interest, it is possible to restrict the search for the maximum correlation to lags that encompass the range of interest. For example, if a stimulus has a known $F_0$ of 100 Hz, one might wish to restrict the frequency range that is sought in the response to a range of 80 to 120 Hz. In this case, one would only look for the maximal correlation in a lag range of 1/80 sec to 1/120 sec (8.33 msec to 12.5 msec). If a peak occurs at a lag of 9.7 msec, one would conclude that the response had an $F_0$ of about 103 Hz. Determining $F_0$ by autocorrelation method is particularly useful when the $F_0$ of the acoustic stimulus or brain response is not known a priori, when the $F_0$ of the acoustic stimulus is known but one desires to determine at what frequency the response occurred, when an acoustic stimulus is missing a fundamental type (e.g. the common denominator of the harmonics and perceived $F_0$, known as "base frequency"), or when a stimulus with a known $F_0$ produces a response peak at a slightly different frequency.

Information known about the stimulus $F_0$ may also be used to choose a suitable frequency window for evaluating one or more aspects of $F_0$.

Different frequency regions of the spectrum will be analyzed based on the eliciting sound. In embodiments where the $F_0$ of the complex sound is static, the region may range from one-half the frequency of the eliciting sound $F_0$ (minimum of the region) to twice the frequency of the eliciting sound $F_0$ (maximum of the region). For example, for a complex sound with a 100 Hz $F_0$. the region of interest may be 50-200 Hz. Alternatively, a frequency window as small as 1 Hz may be selected. In embodiments where $F_0$ of the complex sound varied, the parameters for selecting the $F_0$ analyses of the brain response may be determined by the arithmetic mean $F_0$ of the stimulus or the upper and lower bounds. For example, if the complex sound $F_0$ changed from 100-150 Hz the lower bound frequency region of interest could extend as low as 50 Hz and the upper bound as high as 300 Hz.

One aspect of a response $F_0$ is the amplitude. Amplitude may be calculated over a frequency region that is about 1 Hz, or the frequency region may be a range greater than 1 Hz. Methods for calculating response $F_0$ ranges that are greater than one are described above. A suitable method for quantifying $F_0$ amplitude includes, but is not limited to, the arithmetic mean amplitude over a region, the amplitude at a single frequency point, the total amplitude over a region of interest (summed, integer, root-mean-squared amplitude), and the signal-to-noise ratio of the $F_0$ (i.e., amplitude of $F_0$ vs. amplitude of a neighboring frequency or amplitude of interstimulus region: for example, if $F_0$ is 100 Hz, then a signal-to-noise-ratio may be $\text{Amplitude}_{100\ Hz}/\text{Amplitude}_{90\ Hz}$ or $\text{Amplitude}_{100\ Hz}/\text{Amplitude}_{interstimulus}$). A comparison of the response $F_0$ amplitude to the eliciting sound $F_0$ amplitude (calculated in the same manner) can then be made.

Another aspect of $F_0$ is phase consistency. Phase consistency is a measure of timing variability of individual frequencies in a response. Phase consistency may also be referred to as phase locking or phase-locking factor. Phase consistency may be calculated over a frequency region that is about 1 Hz, or the frequency region may be range greater than 1 Hz. Methods for calculating $F_0$ ranges that are greater than one are described above for both complex sounds with a static $F_0$ and complex sounds where $F_0$ varied.

To calculate phase consistency, a spectrum is calculated over a discrete time period of the response using a fast Fourier transform, as described above. This results in a complex vector that contains a length, indicating the encoding strength of each frequency, and a phase, which contains information about the timing of the response to that frequency. To examine the timing variability of the response, each vector is transformed into a unit vector by dividing the complex FFT by the modulus of the complex FFT. This transformation sets the length component of the vector to one, discarding the information about encoding strength but maintaining the phase information. The resultant phase unit vector is generated for each response trial and then averaged across trials so that the length of the resulting vector provides a measure of the inter-trial phase consistency. It is acceptable to not use every trial. For example, artifact rejecting, or using other criteria, can result in phase consistency being calculated on a subset of the sweeps. Alternatively, or in addition, some number of trials may be averaged prior to calculating phase consistency (e.g., averaging together every 10 trials), and/or the trials may be first filtered (provided the filters do not exclude the frequency bands of interest). Suitable filters and bandwidths are discussed in section (v). Phase consistency can also be calculated using a bootstrapping method, in which a subset of the trials are selected at random, phase consistency is calculated across that subset of trials, those trials are replaced, and the process is repeated for a given number of times.

Instead of or in addition to determining the phase of the signal at a given time-frequency point, as described above, this approach could be used to extract the frequency of a signal at said point or points. Also, in addition to looking at phase consistency over a single time period in the response, a sliding window analysis can be used to calculate phase consistency over small, overlapping time periods of the response (e.g., a 40 msec window with a 39 msec overlap would result in phase consistency being calculated from 0-40 msec, 1-41 msec, 2-42 msec, etc.).

Other signal processing approaches to determine the instantaneous phase of the signal at specific frequencies include, but are not limited to, wavelets. Wavelets are convolved with the brain response signal to provide amplitude and phase information for each time-frequency point(s), and then procedures follow as above. These could include Morlet wavelets, Mexican hat wavelets, Meyer wavelets, and more.

Another aspect of a response $F_0$ is the "$F_0$ frequency error," which refers to the difference in frequency (Hz) between the $F_0$ of the complex sound and the maximum spectral peak in the region of interest in the response. For example, if the largest peak of the response from 75-175 Hz was at 125 Hz, and the stimulus $F_0$ was 100 Hz, then the "$F_0$ frequency error" would be +25 Hz.

Another aspect of a response $F_0$ is $F_0$ sharpness. $F_0$ sharpness may also be referred to as $F_0$ bandwidth. To determine $F_0$ sharpness, the $F_0$ peak in the brain response spectrum is identified as detailed above. The width of the corresponding peak is then selected determining the difference between the surrounding ends of that peak a pre-specified amplitude below that peak, such as 3 dB below the peak, 10 dB below the peak, or the entire length below the peak. The frequency difference between these two boundaries are determined and the ratio between the frequency difference and the pre-specified amplitude is determined, called the Q. For example, the Q of a peak at 100 Hz, with a bandwidth 10 Hz measured 3 dB down from the peak amplitude, would be 10 (100/10). Bandwidth may be determined for peaks other than $F_0$, as well.

Another aspect of a response $F_0$ is "pitch tracking," which refers to the extent to which a brain response tracks an $F_0$ that changes over time (e.g. a complex sound may have a linear increase in $F_0$ from 100 to 150 Hz over the duration of the sound). The idea is that at any given point in the stimulus, the $F_0$ is at a given instantaneous frequency. As an example, perhaps at time 20 msec the instantaneous frequency is 100 Hz; at 70 msec it is 125 Hz; and at 120 msec, it is at 150 Hz. To determine these instantaneous frequencies (either in the stimulus or the response), an autocorrelation approach would be applied to small, overlapping segments of the waveform. For example, to determine the instantaneous frequency at 20 msec, one might extract a segment of the waveform from 0 to 40 msec and apply the autocorrelation technique described above. The resultant derived $F_0$ ($1/L_{max}$) would be assigned to time 20 msec. Then, one would repeat with a segment of the waveform from 1 to 41 msec. The resultant derived $F_0$ ($1/L_{max}$) would be assigned to time 21 msec, etc. In this way, a pitch tracking analysis can be achieved, utilizing the "frequency error" method described above. The difference in frequency (Hz) between the $F_0$ of the stimulus and $F_0$ of the response could be computed for each time point, and the absolute values of the resulting frequency errors could be summed to compute an overall frequency error score, where 0 indicates perfect pitch tracking and larger numbers indicate poorer pitch tracking. While the present disclosure discusses the use of autocorrelation to identify or otherwise obtain instantaneous frequencies, it is contemplated that other algorithms may be used, such as the Hilbert Transform algorithm, the Empirical Mode Decomposition algorithm, the Hilbert-Huang Transform algorithm, among others.

ii. Harmonics

Another aspect of a brain response to a complex sound is the extent to which a brain response reflects the harmonics of the stimulus. Various aspects may be analyzed including, but not limited to, harmonic amplitude, phase consistency, spectral flux, and spectral centroid.

Suitable methods for analyzing various aspects of the response harmonics include those described for $F_0$, changing parameters as needed to reflect the frequency range of the harmonics. For example, when determining phase consistency of the harmonics, frequency information outside of the $F_0$ is analyzed. This region may be as small as 1 Hz, or it may encompass a range of harmonics. Amplitudes at individual harmonics may also be averaged together. In another example, when creating an average of the response in embodiments where the acoustic stimulus was presented to a subject in multiple polarities (e.g., condensation and rarefaction) then, the responses to one of the polarities can be inverted before averaging (i.e., "subtracted") in order to enhance the response to the harmonics. Alternatively, or in addition, harmonic amplitude may be referenced to the amplitude of a non-stimulus-evoked portion of the response. An example of a non-stimulus-evoked portion of the response would be the interstimulus period, in other words the response to the silence between successive stimulus presentations. This interstimulus-period response would be considered background activity of the brain, and so computing the ratio, for example, $RMS_{harmonic}/RMS_{interstimulus}$ would be considered a signal to noise ratio (SNR).

iii. Neural Timing

Another aspect of a brain response to a complex sound is the speed or timing of one or more response peaks of the brain response. The identity and number of response peaks analyzed can vary depending on the acoustic stimulus. For example, while all complex sounds elicit an onset peak, not all features are shared by every complex sound.

In some embodiments, one or more transient feature is analyzed. In other embodiments, one or more sustained feature is evaluated. In other embodiments, one or more transient feature and/or one or more sustained feature is evaluated. In each of the above embodiments, as few as one response peak may be analyzed or more than one response peak may be analyzed. When analyzing more than one response peak, the response peaks may or may not be clustered in the same time region.

As a non-limiting example, if the complex sound was /ada/, a subset of peaks in the response time region corresponding to just the /d/ may be analyzed (accounting for the neural onset delay). Alternatively, or in addition, the onset peak could be analyzed and/or the consonant-to-vowel transition (or just a portion thereof) could be analyzed. As another example, when a complex sound has a longer duration and encompasses multiple, discrete features (e.g., complex speech sounds comprising multiple phonemes or syllables or a complex sound that is musical melody or comprised of several musical notes), it might be logical, in these cases, to perform an analysis over discrete acoustic/phonetic portions of the complex sound and response.

Aspects of methods for identifying response peaks are described below.

In one approach, the locations of the stereotyped peaks in a brain response may be determined by the individual who collected the data. The method typically involves the use of two or more subaverages generated by a computer to identify where the peaks in a subject's brain response reliably occur. The peaks are then marked on the final averaged waveform. Alternatively, a normative database may be used in addition to or instead of subaverages. For example, a table listing expected peaks and typical latency ranges for each peak could be consulted. In additional examples, a "norm" response that is the average of all of the individuals in a normative database could be used, or a subject's previous response that already has marked peaks could be used. In yet another example, an algorithm may be used to identify local minima and maxima within a predetermined window. For example, a computer could detect the timing of the largest amplitude point within a pre-specified window (e.g., about 6 to 10 msec for an onset peak). A computer program could use other signal processing approaches to identify these peaks, such as a principal components analysis to identify a peak-to-trough complex in the response. Using the /da/ syllable for illustration, a computer program could identify V and A based on their shape and statistical modeling of the response vs. a norm. Alternatively still, a hybrid method of the above approaches may be used. For example, an algorithm may initially identify peaks and an individual adjusts them, or vice-versa.

An alternative approach to determine neural timing may use a stimulus-response cross-correlation approach, for example as described below. Instead of a correlation value, the timing shift that achieves the maximum correlation is used to quantify neural timing ($L_{max}$=neural timing).

A third approach to determine neural timing may involve calculating the phase delay. also known as the group delay of the response. The group delay calculates the timing of constituent sinusoids in a complex signal, and so provides a frequency-specific measure of timing. It is the rate of change of transmission phase angles of the frequencies in the signal. It is calculated as the negative first derivative of the phase response of a signal:

$$\tau_g(w) = -\frac{d\phi(w)}{dw}$$

where $\tau_g(w)$ group delay, $\phi$ is the phase difference between the signal and response, and w is the frequency. This can be computed across all frequencies ($\tau_g(w)$)) or for individual frequencies in the response ($\tau_g(\phi)$). These frequency ranges of interest may be determined based on the criteria discussed under $F_0$ or harmonics.

iv. Response Amplitude

Another aspect of a brain response to a complex sound is the amplitude of one or more response peaks of the brain response. This aspect is conceptually similar to $F_0$ amplitude, however, $F_0$ is a frequency domain measurement and response peaks are time domain measurements. In some embodiments, one or more transient feature is analyzed. In other embodiments one or more sustained feature is analyzed. In other embodiments one or more transient feature and/or one or more sustained feature is analyzed. In each of the above embodiments, as few as one response peak may be analyzed or more than one response peak may be analyzed. When analyzing more than one response peak, the response peaks may or may not be clustered in the same time region.

As a non-limiting example, if the complex sound was /ada/, a subset of peaks in the response time region corresponding to just the /d/ may be analyzed (accounting for the neural onset delay). Alternatively, or in addition, the onset peak may be analyzed and/or the consonant-to-vowel transition (or just a portion thereof) may be analyzed. As another example, when a complex sound has a longer duration and encompasses multiple, discrete features (e.g., complex speech sounds comprising multiple phonemes or syllables or a complex sound that is musical melody or comprised of several musical notes), it might be logical, in these cases, to perform an analysis over discrete acoustic/phonetic portions of the complex sound and response.

Methods for identifying response peaks, and regions of peaks, are discussed above. Computational methods suitable for determining a response amplitude for an individual peak or a region comprising multiple peaks include, but are not limited to, arithmetic mean amplitude over a region, the root-mean-squared [RMS] amplitude of the peak or region, mean amplitude of the points, max point minus min point (i.e., peak-to-peak maximum), sum of the points in the rectified waveform, amplitude at a single frequency point, the total amplitude over a region of interest (summed, integer, root-mean-squared amplitude), etc.

In certain embodiments, the amplitude of a response peak may be referenced to the amplitude of a non-stimulus-evoked portion of the response. An example of a non-stimulus-evoked portion of the response may be the interstimulus period, in other words the response to the silence between successive stimulus presentations. This interstimulus-period response would be considered background activity of the brain, and so computing the ratio $RMS_{response}/RMS_{interstimulus}$ would be considered a signal to noise ratio (SNR). If desired, an SNR may be expressed in decibels (dB) by taking the 10-base log of the RMS amplitude ratio and multiplying by 20.

In other embodiments, the amplitude of a response peak may be referenced to the amplitude of a non-stimulus-evoked portion of the response. An example of a non-stimulus-evoked portion of the response would be the interstimulus period, in other words the response to the silence between successive stimulus presentations. This interstimulus-period response would be considered background activity of the brain, and so computing the ratio response/interstimulus would be considered a signal to noise ratio (SNR).

A comparison of a response peak amplitude to the eliciting sound peak amplitude (calculated in the same manner) can then be made.

v. Stimulus-Response Correlation

Another aspect of a brain response to a complex sound is the extent to which the response resembles the evoking sound. Stimulus-response correlations may be performed in the time domain or the frequency domain.

To determine stimulus-response correlation in the time, an acoustic stimulus may be filtered across a bandwidth to match the response and each subject's response may be cross-correlated to the filtered stimulus. Other suitable methods may also be used.

The type of filter may vary (e.g., Butterworth, Chebyshev, elliptic, Kaiser, etc.), as may the order (e.g., first-order, second-order, etc.) which is also known as the number of poles. The higher the order, the less energy is present outside the specified filter bandwidth.

The bandwidth across which the filter is applied may vary. Generally speaking, an acoustic stimulus will have higher frequency content than a frequency following response (FFR) from the brain. Therefore, low-pass filtering of the acoustic stimulus will result in a stimulus waveform that correlates better with the FFR. To select the low-pass filter cutoff, one approach is to match the bandwidth to that of the FFR recording's bandwidth. A second approach is to choose a low-pass filter that approaches the actual frequency content of the FFR. This approach might result in a low-pass filter of about 1000 Hz because typically an envelope-dominated FFR will have little energy above 1000 Hz. Likewise, the choice of high-pass filter may be matched to the FFR recording or may some other value that approximates the lowest frequency present in the FFR collection.

The time window selected for performing the cross-correlation may vary. In one approach, when the complex sound is a speech sound, a selected time window may correspond roughly to the fully-voiced portion of the stimulus. For example, the time window described in the examples for the /d/ stimulus omits the unvoiced consonant release and the transient FFR component corresponding to the onset of voicing. Other time windows, encompassing a voiced (i.e. periodic) response waveform might also be selected. For example, longer speech stimuli may encompass multiple phonemes or syllables. It might be logical, in these cases, to perform this analysis over discrete acoustic/phonetic portions of the stimulus and response—e.g., just the voiced portion of a consonant transition, or, just a steady-state vowel portion. Similar concepts apply to other complex sounds.

The cross-correlation function is a standard procedure that time-shifts one waveform (A) with respect to another (B) and correlates A to B at many such time shifts. For example, A(1:10) (i.e., points 1 to 10 of waveform A) is correlated to B(1:10), then A(1:10) is correlated to B(2:11), then 13 (3:12), etc. The reverse shift also is evaluated, such that A(1:10) is correlated with B(−1:9) and B(−2:8) etc. Each time shift is considered a "lag," such that A(1:10) vs B(1:10) has a lag of 0. A(1:10) vs B(2:11) has a lag of 1, etc. Pearson product-moment correlation, point-biserial, or Spearman techniques may be used to create a correlation score. For example, the Pearson product-moment correlation produces an "r" score. This results in a value scaled from −1 to +1, with +1 meaning perfect correlation, −1 meaning perfect anti-correlation (i.e., identical, but fully out-of-phase), and 0 meaning complete lack of correlation. A type of correlation that produces values outside the −1 to +1 range might also be used.

In performing the cross-correlation, the time-shift (lag) which produces the maximum Pearson's r value (or value produced by another method) is sought. However, there are logical constraints to the lag. For example, it is illogical that the brain response would occur before the stimulus. Therefore, negative lag values are not considered. Likewise, it takes about 6-10 msec for the auditory pathway to respond to a sound and to propagate the signal to the recording electrodes. Therefore, a lag smaller than about 6 msec would be illogical because it is simply not biologically possible. Also, it typically does not take longer than about 10-12 msec for a signal to arise. So, an "appropriate lag" is typically a range of about 6 to about 15 msec, or about 6 to about 12 msec. A slightly different lag would also be acceptable.

When performing parametric statistical analysis on Pearson's correlation data, a Fisher-transformed z score may be calculated. While not strictly necessary, statistical conclusions drawn from non-transformed data may be suspect. This is a mathematical, natural-log-based, transformation that normalizes the r distribution so that all delta-r values, along the −1 to +1 range are equivalently constant. That is, the variance of untransformed r-values that are toward the ends of the range (near −1 or near +1) is much smaller than the variance of r-values at the middle of the range (near 0).

All descriptions and alternatives described above involve time-domain comparisons between an acoustic stimulus and its evoked response. Correlations could also be performed between frequency-domain waveforms of the stimulus and response. The major difference, aside from the frequency-domain conversion itself, is that the allowance for the lag would have to be made in the time domain prior to frequency-domain conversion and a straight (i.e., lag=0) correlation would be performed. For example, regarding a frequency-domain correlation of neural activity to the 20 to 80 msec portion of a particular stimulus, if a typical response, due neural propagation time, arises 8 msec after the stimulus, one may perform a frequency-domain conversion of the 20-80 msec segment of the stimulus and of the 28-88 msec segment of the response. Then, once in the frequency domain, a straight correlation (lag=0) may be performed.

vi. Response Consistency

Another aspect of a brain response to a complex sound is the extent to which every presentation of the same acoustic stimulus (each a "trial") results in the same brain response. This may also be referred to as the stability of response. Response-consistency calculations may be performed in the time domain or the frequency domain. In addition, response-consistency calculations may be performed on an added waveform (e.g., opposing-polarity stimulus presentations are added) or a subtracted waveform (e.g., opposing-polarity stimulus presentations results subtracted/the responses to one of the polarities can be inverted).

In one approach, approximately half of the trials are randomly selected and averaged, and the remaining trials are averaged. The two sub-averaged waveforms are then correlated over a time window to determine their similarity. The time window can vary, as described above for stimulus-response correlation. Suitable methods for calculating a correlation score include, but are not limited, to Pearson product-moment correlation, point-biserial, or Spearman techniques; correlation data may be Fisher-transformed to a z score before averaging. These steps may then be repeated a number of different times, each repetition with a different random samplings of trials, and the correlation values from each repetition may be averaged (arithmetic mean) to generate a final measure of inter-trial response consistency. The number of repetitions can vary, but should be selected to provide confidence that the final mean correlation value is a good representation of the underlying data. Another approach is not to maintain individual trials, but rather collect two discrete subaverages.

vii. Difference Measures

A "difference measure" refers to a means of quantifying a change in a measure. For example, a difference measure may provide a means of quantifying a change in a response component in the same subject after time has passed, or after injury or intervention has taken place. A difference measure also refers to a means to quantify a difference in the same response component(s) to two (or more) different stimuli in the same subject. Additionally or alternatively, a difference measure may be applied to two measures within a single response. For example, the timing difference between peaks V and A, the phase-locking ratio between the $F_0$ and one or more harmonics, the amplitude ratio between multiple harmonics, the RMS amplitude difference between added- and subtracted-polarity responses, etc.

Difference measures may be expressed as a percent change (e.g., increase or decrease), as absolute terms (e.g., delay in msec; decrease in magnitude in $\mu V$, increase in frequency error in Hz, decrease in response consistency in r, etc.), or as a dB difference.

In embodiments where an acoustic stimulus comprises background noise, a difference measure may be a change in a response component in the presence of background noise as compared to the absence of background noise. For example, background noise is known to diminish response amplitudes, so one may wish to determine the percent reduction of $F_0$ amplitude when background noise is added to the acoustic stimulus. Any of the above listed measurements can be evaluated.

Non-limiting examples of other contexts in which two or more responses could be compared include: changes in one or more frequencies in the sound (a /d/ with a high pitch vs a /d/ with a low pitch); different speech sounds (a /d/ compared to a /b/); sounds of varying amplitude modulation index, also known as modulation depth (the extent to which, in a complex signal, the ratio of the excursions of the modulated signal to the unmodulated signal, resulting in the degree of local amplitude envelope variation between two consecutive peaks in the signal); musical sounds of different pitch or timbre; etc.

II. Methods (a) Identifying Non-Penetrating Brain Injury and/or Classifying a Subject The present disclosure provides methods for the acute assessment and evaluation of non-penetrating brain injury in a subject, as well as methods for classifying a subject that received a hit to the body that transmitted an impulsive force to the brain as either having a non-penetrating brain injury or not.

In one aspect, a method comprises analyzing one or more components of the subject's brain response to an acoustic stimulus comprising a complex sound; and identifying the subject as having a non-penetrating brain injury when a value for at least one component of the brain response is anomalous, wherein the component(s) is selected from fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In some embodiments, a complex sound comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises analyzing one or more components of the subjects brain response to an acoustic stimulus comprising a complex sound; and identifying the subject as having a non-penetrating brain injury when a value for at least one component of the brain response is anomalous, wherein the component(s) is selected from fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In another aspect, a method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous, wherein the component(s) is selected from fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous, wherein the component(s) is selected from fundamental frequency ($F_0$) and/or harmonics, neural timing of a sustained response peak, response amplitude over some or all of a consonant-vowel transition, and stimulus-response correlation over a time window that encompasses a sustained response. In some embodiments, the method further comprises analyzing one or more transient responses to an acoustic stimulus. The complex sound may be selected from those described above in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, a vowel-to-consonant transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In another aspect, a method comprises analyzing one or more components of the subject's brain response to an acoustic stimulus comprising a complex sound; and classifying the subject as having a non-penetrating brain injury when a value for at least one component of the brain response is anomalous, wherein the component(s) is selected from fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In some embodiments, a complex sound comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises analyzing one or more components of the subject's brain response to an acoustic stimulus comprising a complex sound; and classifying the subject as having a non-penetrating brain injury when a value for at least one component of the brain response is anomalous, wherein the component(s) is selected from fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In another aspect, a method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous, wherein the component(s) is selected from fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous, wherein the component(s) is selected from fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound may be selected from those described above in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In each of the above aspects, the subject may be symptomatic or asymptomatic. Evaluation of the subject following a suspected or known non-penetrating brain injury may occur at any time. In some embodiments evaluation occurs within 1 week of the injury. In other embodiments, evaluation occurs within 48 hours of the suspected injury. In other embodiments, evaluation occurs within 24 hours of the suspected injury. In other embodiments, evaluation occurs within 12 hours of the suspected injury. In other embodiments, evaluation occurs within 6 hours of the suspected injury. In other embodiments, evaluation occurs within 3 hours of the suspected injury. In other embodiments, evaluation occurs within 1 hour of the suspected injury.

As used herein, the term "anomalous value" refers to a deviation from the value for a control group or a normative value or a deviation from a previously established value for the subject (i.e., a "baseline value"), wherein the deviation exceeds the difference expected by chance. When an anomalous value is a deviation from a value for a control group, the members of the control group may have never been diagnosed with a non-penetrating brain injury. Alternatively, the members of the control group may be a group of subjects that have never been diagnosed with a concussion. In another example, the control group may be a demographic subsample based on relevant information about the subject including, but not limited to, the subject's age and/or life experiences (e.g., number of years playing a contact sport, number of years in the military, number of years in a combat/war zone, number of car accidents, number of concussions, etc.). When an anomalous value is a deviation from a previously established value for the subject (i.e., a "baseline value"), the value may have been established before a subject was diagnosed with a non-penetrating brain injury including, but not limited to, a concussion or traumatic brain injury (TBI). Alternatively, a baseline value may have been established at a significant point in time—e.g., the start of a sports season, the start of a game or a competition, enlistment into the military, deployment to a combat/war zone, the start of employment, etc. A baseline value may also be the first available measurement for a subject. When an anomalous value is a deviation from a value a normative value, the normative value may be obtained from published sources.

An example of a suitable method for determining whether a deviation exceeds the difference expected by chance includes an analysis of statistical deviation e based on probability distributions based on raw values or normalized values (e.g., z-scores, etc.), wherein one-half standard deviation or more (e.g. 1, 2, 3, 4, 5, or more) indicates a deviation that exceeds the difference expected by chance. Alternatively, a score or value may be converted to percentiles based on established value (e.g., an entire population's performance or based on a demographic subsample), wherein performance at or below the $50^{th}$ percentile, the $45^{th}$ percentile, the $40^{th}$ percentile, the $35^{th}$ percentile, the $35^{th}$ percentile, the $30^{th}$ percentile, the $25^{th}$ percentile, the $20^{th}$ percentile, the $19^{th}$ percentile, the $10^{th}$ percentile, or the $5^{th}$ percentile indicates a deviation that exceeds the difference expected by chance. In another example, a deviation that exceeds the difference expected by chance may be a difference determined by the minimum detectable change (MDC). The MDC refers to a statistic reflecting the smallest amount of deviation in a patient's score that ensures the change is not the result of measurement error, defined as $1.96 \times$ the standard error of the mean on the test$\times \sqrt{2}$. In another example, a deviation that exceeds the difference expected by chance may be determined by confidence intervals—a range of values in which there is a specified probability that the value of a measure lies within said range in a healthy population. For example, if a healthy population has a 90% confidence interval of 100-120, then in 90% of hypothetical cases, one would predict performance in the population to fall within 100-120, so a score outside the confidence interval would be unlikely and anomalous. Common confidence interval ranges include 90%, 95%, and 99%. In another example, a deviation that exceeds the difference expected by chance may be determined by a statistical test to determine if a score falls outside of the range of expected based on frequentist probability theory, such as a student's t-test, an analysis of variance, a regression, a Mann-Whitney U test, a chi-square test, etc. In another example, a deviation that exceeds the difference expected by chance may be determined by a statistical test to determine if a score falls outside of the range of expected values based on Bayesian statistical theory. In another example, a deviation that exceeds the difference expected by chance may be a score that exceeds a threshold determined by research. This may be a categorical threshold (such as a body temperature over 100° qualifies as a fever) or it may be a threshold from a statistical algorithm that balances the probability of receiving true positive and true negative results. In embodiments where the deviation is a value that exceeds a threshold from a statistical algorithm, the threshold typically produces at least an 80% sensitivity (true positive rate) and an 80% specificity (true negative rate), and has a strong predictive utility (e.g. as indicated by a Receiver Operating Characteristic (ROC)$\geq 0.80$, preferably, 0.85, more preferably $\geq 0.90$; other types of predictive values include PPV, NPV, etc.). In another example, when the anomalous value refers to a deviation from a previously established value for the subject, a deviation that exceeds the difference expected by chance may be a difference in score that exceeds the threshold expected based on the test-retest performance in a healthy population. For example, if tests in a healthy population showed that an $F_0$ amplitude is expected to vary by 3 µV between tests, then a difference of about 4 µV between tests in a patient would be considered anomalous.

As used herein, "a value for at least one component of the brain response" includes one, two, three, four, five or more values for one or more components independently selected from the recited groups, wherein at least one component is an aspect of the FFR. Components that are an aspect of the FFR include fundamental frequency ($F_0$), harmonics, neural timing of a sustained response peak, response amplitude over a time window that encompasses some or all of a sustained response, and stimulus-response correlation a time window that encompasses some or all of a sustained response. As stated above, the method may further comprise analyzing one or more transient responses. In some embodiments, a transient response may be the timing or amplitude of an onset peak or onset response. In embodiments where the complex sound comprises one or more amplitude bursts, a suitable transient response may be the timing or amplitude of a transient response to the onset of one or more of the amplitude bursts.

As used herein, "a value for at least one component of the brain response" also includes embodiments where brain response values are combined together using a statistical model to produce a new measurement and the new measurement is anomalous, as described above. A statistical model may have one or multiple steps. In embodiments where a statistical model has one step, two or more values are used in the single step. In embodiments where a statistical model has two or more steps, each step may include a single value or combine one or more values. For example, a first step may control for demographic factors that could have an effect on the FFR independent of brain injury. Non-limiting examples of values that may be included in the first step include age, gender, pre-existing medical conditions, background noise in the FFR (e.g., amplitude of non-stimulus related neural activity, such as in the inter-stimulus region, etc.), timing of the onset peak (e.g. wave V in response to a click), etc. One or more additional steps may then incorporate one or more values for a component that is an aspect of the FFR (e.g., two, three, four, five or more values for one or more components independently selected from the recited groups). Again, value(s) for one or more transient responses may be included with the FFR values. Suitable models should have a NPV and a PPV greater than about 80%, preferably greater than about 85%, more preferably greater than about 90%; and/or an ROC curve with an AUC value greater than about 0.80, preferably greater than about 0.85, more preferably greater than about 0.90.

In an embodiment, at least one anomalous value comprises $F_0$ and stimulus-response correlation over a time window that encompasses some or all of a sustained response. In another embodiment, at least one anomalous value comprises $F_0$ and amplitude of the onset response. In another embodiment, at least one anomalous value comprises stimulus-response correlation over a time window that encompasses some or all of a sustained response and amplitude of the onset response.

In embodiments where a value of fundamental frequency ($F_0$) is anomalous, the anomalous value may be $F_0$ amplitude, $F_0$ phase consistency, $F_0$ sharpness, $F_0$ frequency error, pitch tracking, or any combination thereof. Methods for determining these values are described above in Section I(b)(i).

In embodiments where a value for neural timing of a response peak is anomalous, one, two, three, or more response peaks may have anomalous values. In certain embodiments, a value for neural timing of at least one sustained response peak is anomalous. As a non-limiting example, if the complex sound comprises /da/, the timing of peak A, peak D, or peak E may be anomalous, as well as any combination thereof. Methods for determining neural timing of a sustained response peak(s) are described above in Section I(b)(iii).

In embodiments where response amplitude over some or all of the FFR is anomalous, the time window over which the response amplitude is calculated may be a portion of the FFR or the entire FFR. In some embodiments, the time window over which response amplitude is calculated includes at least one formant, preferably at least two formants (or equivalent of a formant for non-speech sounds). As a non-limiting example, when a complex sound comprises a consonant-to-vowel transition and response amplitude over the consonant-to-vowel transition is anomalous, the time range over which the response amplitude is calculated may optionally include unvoiced consonant release and/or the transient FFR component corresponding to the onset of voicing. When a complex sounds comprises more than one consonant-to-vowel transition, the response amplitude over the consonant-to-vowel transition may or may not be anomalous at each transition. Methods for determining the response amplitude over a FFR region are described above in Section I(b)(iv).

In embodiments where a stimulus-response correlation value over a time window that encompasses some or all of a sustained response is anomalous, the anomalous value may be a time-domain measurement, a frequency-domain measurement, or both. In preferred embodiments, the frequency domain window would include one or more formants, and in one specific example, at least two formants (or equivalent of a formant for non-speech sounds). As a non-limiting example, when the complex sound is a speech sound, the time window may comprise a portion, or all, of a voiced response, including but not limited to a consonant-to-vowel transition, a voiced portion of a consonant transition, or a steady-state vowel portion. Methods for determining stimulus-response correlation values are described above in Section I(b)(v).

(b) Determining a Change in a Non-Penetrating Brain Injury

The present disclosure also provides methods for determining a change in non-penetrating brain injury. These methods may be used to assess a subject's recovery from a non-penetrating brain injury to determine if the brain injury is worsening, improving, or has stayed the same. Subjects recovering from non-penetrating brain injury may or may not receive a therapeutic intervention. Non-limiting examples of types of therapeutic interventions include pharmaceutical, psychological (e.g. memory tests or brain "exercises"), auditory, and behavioral. For example, a subject recovering from non-penetrating brain injury may have been advised to rest and/or refrain from activities that may further worsen the non-penetrating brain injury. Alternatively, a subject recovering from non-penetrating brain injury may be involved in a treatment program with the goal of speeding recovery or recovering aspects of brain function that would not have returned but for the treatment. A determination that the non-penetrating brain injury is worsening or has stayed the same may result in the start of a therapeutic intervention, a change in the type of therapeutic intervention, and/or or a modification of an existing therapeutic intervention; and/or advisement that the subject should refrain from activities that may further worsen the non-penetrating brain injury. A determination that the non-penetrating brain injury has improved or has stayed the same may result in the maintenance, change and/or discontinuation a therapeutic intervention, and/or may result in the subject being cleared to resume all activities.

In one aspect, a method comprises (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) is selected from fundamental frequency ($F_0$) and/or harmonics, neural timing of a response peak, response amplitude over a time window that encompasses some or all of a sustained response, and stimulus-response correlation over a time window that encompasses some or all of a sustained response. If the absolute value of the difference is greater than would be expected by chance, there is a change in the non-penetrating brain injury. In some embodiments, a complex sound comprises a speech sound or a non-speech vocal sound. In some embodiments, a complex sound comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) is selected from fundamental frequency ($F_0$), neural timing of a sustained response peak, response amplitude over a time window that encompasses some or all of a consonant-to-vowel transition, and stimulus-response correlation over a time window that encompasses some or all of a sustained response. If the absolute value of the difference is greater than would be expected by chance, there is a change in the non-penetrating brain injury. In some embodiments, a component is an aspect of the FFR. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In another aspect, a method comprises two steps. The first step, i.e., step (a), tests a subject's brain response to an acoustic stimulus by: (1) fitting the subject with electrodes to measure voltage potentials generated from the subject's brain; (2) administering to the subject an acoustic stimulus, wherein the acoustic stimulus comprises a complex sound; (3) recording voltage potentials from the subject's brain for at least the duration of the acoustic stimulus; and (4) analyzing the voltage potentials to determine one or more components of the brain response; wherein the component(s) is selected from fundamental frequency ($F_0$), neural timing of a response peak, response amplitude over a time window that encompasses some or all of a sustained response, and stimulus-response correlation over a time window that encompasses some or all of a sustained response. The second step, i.e., step (b), re-tests a subject's brain response to the same acoustic stimulus by repeating steps (a)(1)-(4) and determining any differences in the one or more components from step (a). If the absolute value of the difference is greater than would be expected by chance, there is a change in the non-penetrating brain injury. The complex sound may be selected from those described above in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are further detailed above in Section I(a)(iii).

In another aspect, a method comprises two steps. The first step, i.e., step (a), tests a subject's brain response to an acoustic stimulus by: (1) fitting the subject with electrodes to measure voltage potentials generated from the subject's brain; (2) administering to the subject an acoustic stimulus, wherein the acoustic stimulus comprises a complex sound; (3) recording voltage potentials from the subject's brain for at least the duration of the acoustic stimulus; and (4) analyzing the voltage potentials to determine one or more components of the brain response; wherein the component(s) is selected from fundamental frequency ($F_0$) and/or harmonics, neural timing of a sustained response peak, response amplitude over a time window that encompasses some or all of a consonant-to-vowel transition, and stimulus-response correlation over a time window that encompasses some or all of a sustained response. The second step, i.e., step (b), re-tests a subject's brain response to the same acoustic stimulus by repeating steps (a)(1)-(4) and determining any differences in the one or more components from step (a). If the absolute value of the difference is greater than would be expected by chance, there is a change in the non-penetrating brain injury. The complex sound may be selected from those described above in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from /da/, /pa/, /ka/, /ta/, /ba/, and /ga/. Methods for recording a brain response to an acoustic stimulus are further detailed above in Section I(a)(iii).

In each of the above aspects, the subject may be symptomatic or asymptomatic. For example, a subject may be asymptomatic at testing and re-testing. Alternatively, a subject may be symptomatic at testing and asymptomatic at re-testing. In another example, a subject may be symptomatic at testing and at re-testing, but one or more symptom may have improved when re-testing occurs. In another example, a subject may be asymptomatic at testing and symptomatic at re-testing.

In each of the above aspects, the subject may be identified as having a non-penetrating brain injury in step (a) when a value for at least one component of the brain response is anomalous. In step (b), differences may be calculated only for those anomalous values, or may be calculated for all previously evaluated components. In the latter, components that did not change may be used as a control. Anomalous values and response components are described above in Section II(a).

As used herein, "determining any differences in the one or more components" refers to calculating a difference measure. The direction of the change in the difference measure, i.e., positive or negative, indicates whether the change is an indication of improvement or deterioration in the non-penetrating brain injury. For example, an increase greater than would be expected by chance in response $F_0$ amplitude, $F_0$ phase consistency, $F_0$ sharpness, pitch tracking, response amplitude over the consonant-to-vowel transition, or stimulus-response correlation value indicates improvement, whereas a decrease greater than would be expected by chance in response $F_0$ frequency error or neural timing indicates improvement.

As used herein, "a value for at least one component of the brain response" includes one, two, three, four, five or more values for one or more components independently selected from the recited groups, wherein at least one component includes an aspect of the FFR. "A value for at least one component of the brain response" also includes embodiments where brain response values are combined together using a statistical model to produce a new measurement.

III. Systems

Figure 7:
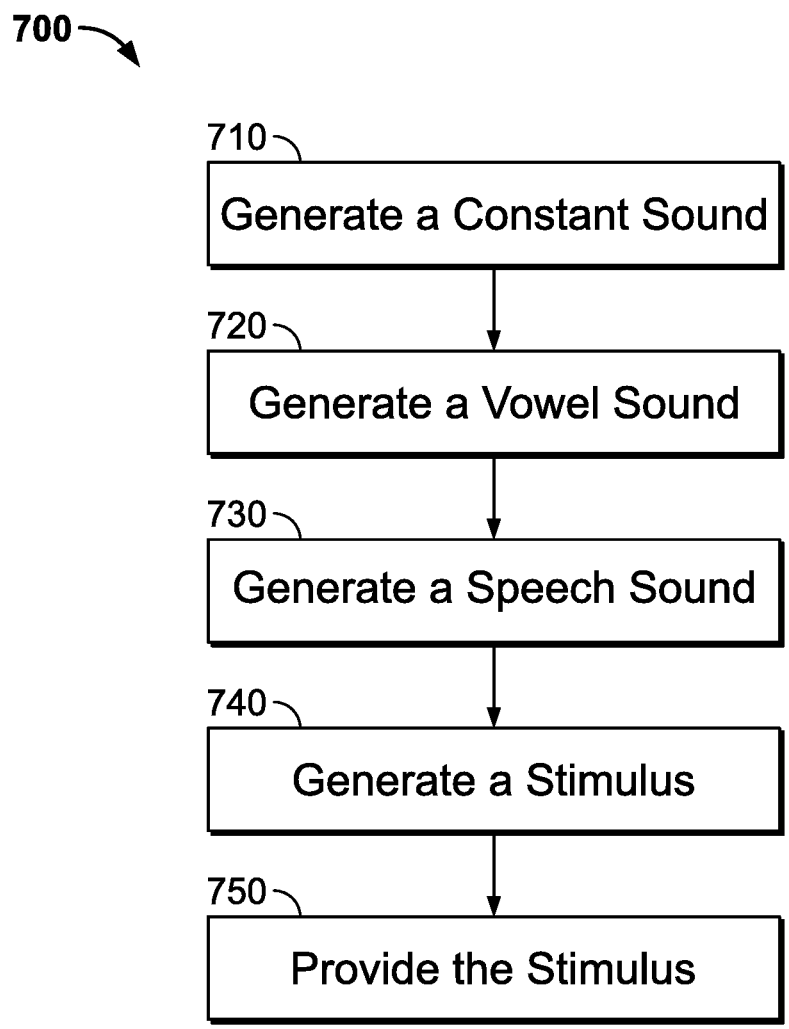
FIG. 7 illustrates an example process 700 for generating stimuli and processing brain response data to identify or otherwise determine non-penetrating brain injuries.
Figure 8:
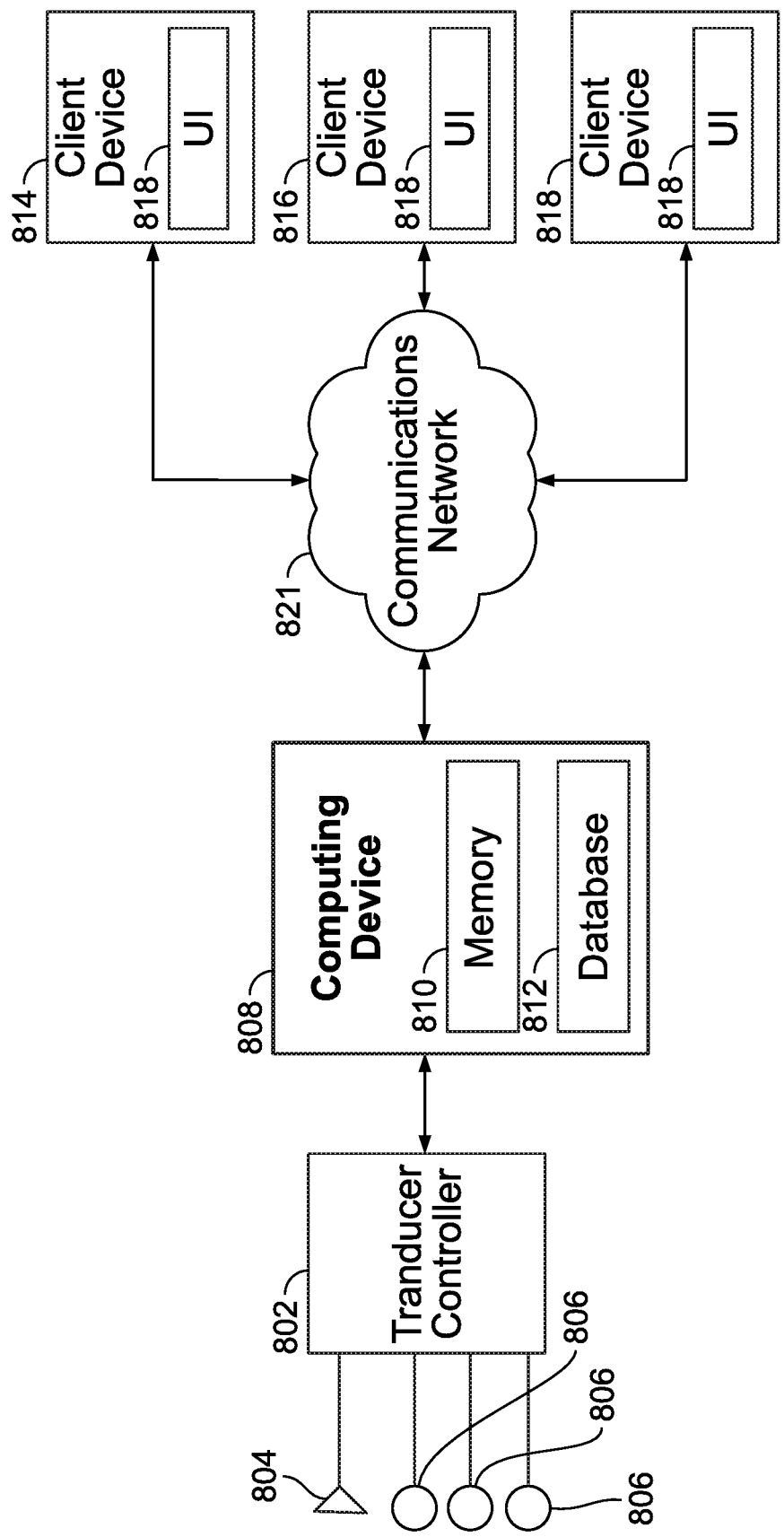
FIG. 8 illustrates an example of a computing environment and/or computing system 700 that automatically transmits acoustic stimuli, receives and processes brain response data, and automatically generates indications of non-penetrating brain injuries based on the brain response data.
Figure 9:
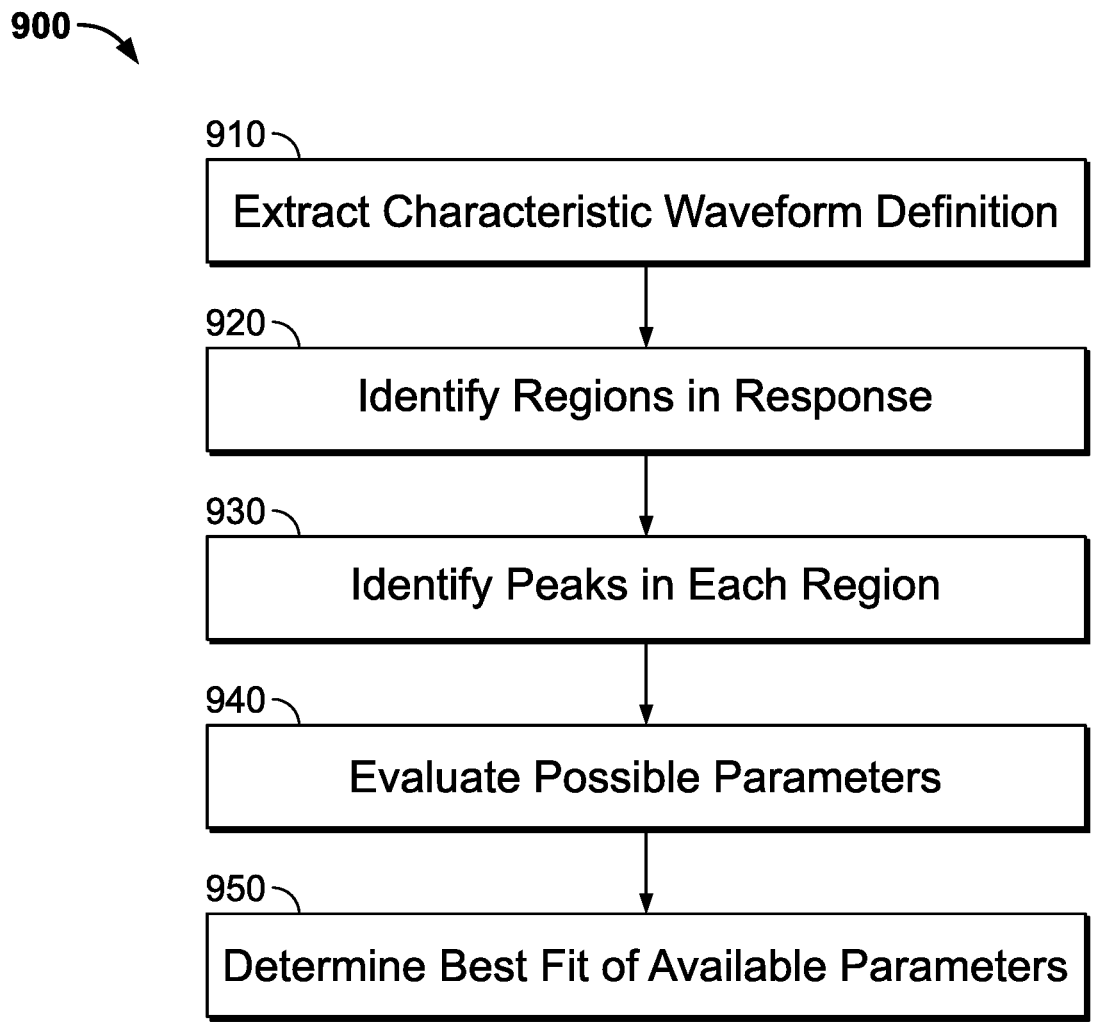
FIG. 9 illustrates an example process 900 for generating stimuli and processing brain stem response data to identify or otherwise determine non-penetrating brain injuries.

An illustrative process and system for automatically generating acoustic stimuli and processing brain response data to identify non-penetrating brain injuries in subjects is depicted in FIGS. 7-9. In particular, FIGS. 7 and 9 illustrate example processes 700 and 900 for generating stimuli and processing brain stem response data to identify or otherwise determine non-penetrating brain injuries. FIG. 8 illustrates a computing environment and/or computing system 700 that automatically transmits acoustic stimuli, receives and processes brain response data, and automatically generates indications of non-penetrating brain injuries based on the brain response data. More specifically, FIG. 8 illustrates a computing environment and/or computing system 700 including a server computing device 708 operating in conjunction with various other hardware and/or software components that may be used to perform or otherwise execute the process 700 and process 900.

Referring initially to FIG. 8, the computing environment 800 includes a transducer controller 802 functionally coupled to an acoustic transducer 804 and one or more electrodes 806. More specifically, the transducer controller 802 represents a computing and/or processing device that delivers a stimulus to the acoustic transducer 804. Additionally, the transducer controller 802 may receive and process brainwave signal information from the one or more electrodes 806. The transducer controller 802 may be any suitable stimulus delivery and data acquisition system, including PC-based stimulus delivery and data acquisition systems such as those available from Bio-logic Systems Corporation or Compumedics. The acoustic transducer 804 may be an insert earphone such as the ER-3 insert earphone available from Etymotic Research, Elk Grove, Ill. The one or more electrodes 806 may be Ag—Ag Cl scalp electrodes, which may be positioned on the test subject from Gz (active) to ipsilateral earlobe (reference) with forehead ground.

The transducer controller 802 may be functionally connected to a computing device 808 including a memory 810 within which instructions are retained directing the operation of the computing device 808 for carrying out the herein described methods and processes (e.g., process 700 of FIG. 7 and process 900 of FIG. 9). More specifically, the computing device 808 automatically generates a test stimulus signal, communicates the test stimulus signal to the transducer controller 802 for generation of an acoustic stimulus that is presented or otherwise provided to the test subject via the acoustic transducer 804. The computing device 808 may obtain brain response data via the electrodes 806 and the transducer controller 802, The brain response data may be stored within the memory 810 and/or stored or otherwise maintained in a database 812.

The computing device 808 may transmit the brain response data to one or more client devices 814-820. The or more client devices 814-820 functionally communicate with the computing device 808 through a communications network 821, which may be the Internet, an intranet, and Ethernet network, a wireline network, a wireless network, and/or another communication network. The one or more client devices 814-820 may be a personal computer, work station, mobile device, mobile phone, tablet device, processor, and/or other processing device capable of implementing and/or executing processes, software, applications, etc., that includes network-enabled devices and/or software, such as user-interface 818 for communication over the communications network 112 (e.g., browsing the internet), Additionally, the one or more client device(s) 814-820 may include one or more processors that process software or other machine-readable instructions and may include a memory to store the software or other machine-readable instructions and data.

The database 812 may include one or more data structures used to stored data for analysis of the acquired brain response data. For example, the database 812 may contain one or more data structures containing normative response data to which the acquired brain response data may be compared to provide comparison data. The database 812 may further contain criteria data for evaluating the comparison data for determining the existence of a non-penetrating brain injury.

Figure 11:
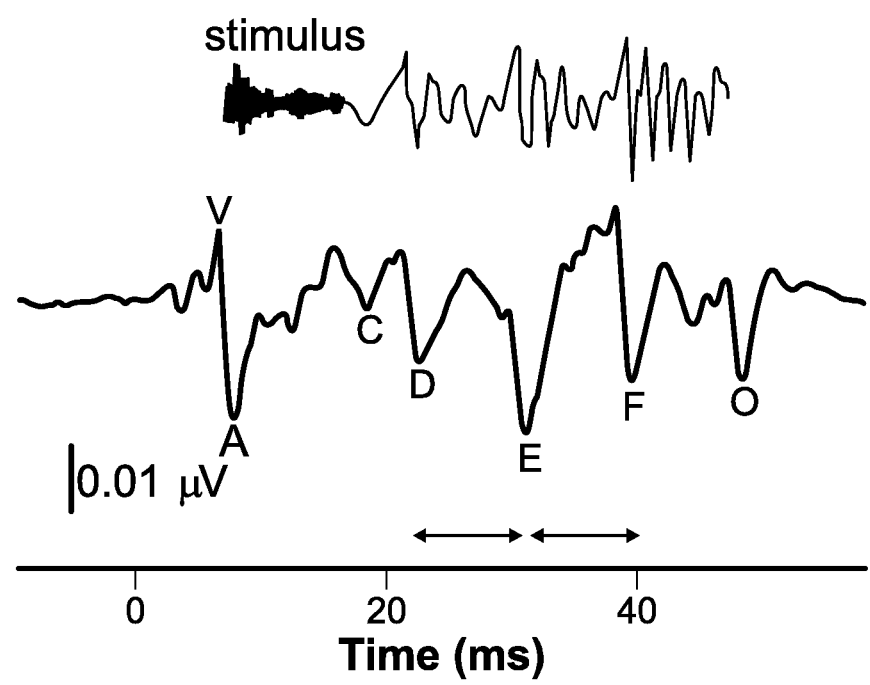
FIG. 11 is a time-domain representation of an acoustic stimulus consisting of a 40 msec /da/ syllable (top) and a brain's response to the stimulus (bottom). The brain response to /da/ includes both transient and sustained response features. The /da/ syllable evokes seven characteristic response peaks that are termed V, A, C, D, E, F, and O. As can be seen in this figure, these peaks relate to major acoustic landmarks in the stimulus. Peaks in the recorded brain response occur 7 to 8 msec after the corresponding stimulus landmark, which is consistent with the neural transmission delay. In this figure, the stimulus waveform is shifted in time to account for this transmission delay and to maximize the visual coherence between the two signals. The V-A complex in the brain response to /da/ is often referred to as the onset response. This sharp onset response arises from the broadband stop burst associated with /d/. Along with V and A, C and O are considered transient responses because they correspond to transient stimulus features, the beginning and end of voicing, respectively. In this figure, the region bounded by D and F forms the frequency following response. Peaks D, E, and F and the small voltage fluctuations between them correspond to sustained stimulus features, namely the fundamental frequency ($F_0$) and its harmonics within the consonant-vowel formant transition. The D-E and E-F interpeak intervals (8 to 9 msec duration, arrows) occur at the period of the $F_0$ of the stimulus, which ramps from 103 to 125 Hz. A systematic approach for identifying these peaks has been established and normative data for 3- to 4-yr olds, 5- to 12-yr olds, and young adults has been published. See, for example, Johnson, et al. (2008), *Clin Neurophysiol*, 119, 2623-2635; or Dhar, S., Abel, R., Hornickel, J., et al. (2009), *Clin Neurophysiol*, 120, 959-966; or Skoe et al. (2014), *Cerebral Cortex*, 25, 1415-1426. Here, the stimulus plot is scaled to match the size of the response. Hence, the microvolt bar refers only to the response.

Referring now to FIG. 7, as stated above, FIG. 7 illustrates a process 700 for generating and applying a stimulus to a subject. The stimulus sound can include any of a variety of real and/or synthetic sounds including a frequency sweep over time against a background (e.g., a sound including one or more transitions based on rapid changes in frequency over a period of time, a sound including a formant transition built with complementary background noise, etc.). One example of a stimulus, illustrated in the example method of FIG. 11, is a consonant-vowel combination against background noise.

At block 710, a consonant sound of a first duration is generated. For example, a /d/, /g/, /c/, etc., is selected as the consonant sound to form part of the audio stimulus to elicit a response from the subject.

At block 720, a vowel sound of a second duration is generated. In certain examples, the second duration is longer than the first duration. That is, the vowel sound is played longer in the stimulus than the consonant sound. For example, an /a/, /i/, /o/, /u/, etc., is selected as the vowel sound to accompany the /d/, /g/, /c/, etc., selected as the consonant sound to form part of the audio stimulus to elicit a response from the subject.

At block 730, a speech sound is generated by combining the consonant sound followed by the vowel sound. For example, the consonant sound and vowel sound are combined by placing the vowel sound after the consonant sound to form the speech sound to be provided in the stimulus. In other examples, the consonant sound follows the vowel sound to form the speech sound.

At block 740, the stimulus is generated by mixing a background noise with the speech sound to generate the stimulus. For example, the background noise includes a plurality of voices talking at the same time and/or approximately the same time to create a human background noise over which the stimulus can be played. In certain examples, the background noise is of a third duration which is longer than the second duration (and, therefore, also longer than the first duration).

At block 750, the stimulus is provided for output with respect to the subject. For example, the stimulus can be output as a six-formant stop consonant constructed in a synthesizer, such as a Klatt-based synthesizer at 20 kHz, etc. In certain examples, following an initial stop burst, a consonant transition (e.g., 50 ms from /d/ to /a/, etc.) during which lower formants (e.g., the lower three formants) shift in frequency (e.g., F1 400-720 Hz, F2 1700-1 240 Hz, F3 2580-2500 Hz, etc.). In these examples, the lower three formants are steady for the subsequent vowel (e.g., 120 ms at /a/), and the fundamental frequency and upper three formants are steady through the stimulus (e.g., F0 100 Hz, F4 3300 Hz, F5 3750 Hz, F7 4900 Hz, etc.). The stimulus is presented against a noise or "babble" track (e.g., six voices speaking semantically anomalous English sentences at a +10 SNR, etc.). In certain examples, the babble track loops continuously since there is no phase synchrony between the onsets of the speech sound and the noise. In certain examples, the stimulus formed from the speech sound and noise is mixed into a single channel that is presented to a single ear of the subject (e.g., the right ear of the subject at 80 dB of sound pressure level (SPL) in alternating polarities through electromagnetically-shielded insert earphones, etc.). In certain examples, stimulus presentation can be controlled with a defined interstimulus interval (e.g., 61 ms, 81 ms, etc.) in a plurality of sweeps (e.g., 4200 sweeps, 6300 sweeps, etc.). While the process 700 described above describes a specific a complex sound that contains a consonant to vowel transition, it is contemplated that other complex sounds may be used, such as the complex sounds described above in Section I(a)(i) and Section I(a)(iv).

Referring now to FIG. 9, a process 900 for analyzing a response to a stimulus from one or more subjects is provided. At block 910, a characteristic waveform definition is extracted from the received response. For example, a time-locked average of one or more subject responses (e.g., inter-response and intra-response averaging) is computed to amplify common features and reduce noise to increase signal-to-noise ratio (SNR) of the characteristic waveform.

At block 920, the characteristic waveform of the response is processed to identify distinct regions within the response. For example, a consonant-vowel complex sound includes three regions: a) a consonant sound region, b) a transition region between the consonant and the vowel, and c) a vowel sound region. These regions may be the same length and/or may be of varying lengths with respect to each other. For example, the vowel sound region may be of longer duration than the consonant sound region, and the transition region may be shorter than the consonant sound region.

The vowel region may be readily identified by analyzing an end of the response to identify a series of evenly spaced peaks that are the brain's response to the fundamental frequency of the vowel sound. Using peak finding techniques such as a windowed, filtered, maxima and/or minima, etc., peaks can be identified and compared for consistency of temporal spacing. Additionally, this technique can be informed by a-priori knowledge about the fundamental frequency of a sound so that an expected spacing between the peaks is known. The vowel region is then defined as the temporal region between the first occurring peak in this train of peaks and the end of the response.

The consonant region (e.g., a region of the first onset peak for the stimulus) can be identified using similar peak finding techniques as those used to find the vowel region. The consonant region is defined as a region between the first large peak, known as the onset peak, in the characteristic waveform, and the next peak that exceeds the onset peak's amplitude. The location of both peaks can be further informed by a-priori knowledge of the stimulus timing and experiential knowledge of a brain's latency in response to onset of sound stimuli.

Once the consonant and vowel regions have been defined, the transition region is defined as the response in temporal period between the end of the consonant region and the beginning of the vowel region. Peaks within this region can also be identified using the same windowed peak-picking algorithm used in identifying peaks in the other two regions.

At block 930, one or more peaks are identified within the determined regions of the response. For example, peaks can be identified within a vowel response region. Using information about the temporal location of peaks within the vowel region from the characteristic response as a template, peak searching can be seeded within the same region on individual responses to the same stimulus. By allowing the peak search to shift slightly within a range relative to the expected location, individual differences in temporal latency from the characteristic response can be captured and used for subsequent analysis. Similarly, individual differences in peak location with the transition region may be captured and used for subsequent analysis.

At block 940, parameters are evaluated based on the regions and determined peak information. For example, by analyzing the response to identify various aspects of the response (e.g., regions of the response, peaks within each region, etc.), parameters (e.g., FFR parameters) can be evaluated to build a model for determination of the behavioral outcome of interest. In certain examples, parameters can be added and/or removed and tested with respect to the developing model. If the parameter improves the model fit, the parameter can be associated with the model. If, however, the parameter worsens or otherwise fails to improve the model fit, the parameter is not associated with the model.

In certain examples, one or more databases and/or other data stores include data and results from testing of different FFR parameters on different demographics. Databases and/or data stores can also include industry-standard behavioral test results obtained from subjects of various ages for comparison in building and evaluating a model.

At block 950, a best fit of available parameters is determined for a desired behavioral outcome model. For example, in determining a best fit, there are many processes by which a combination of independent variables (or features) can be derived so that combination best predicts a set of dependent variables (outcome measures) across a population of individuals. One such method is regression (e.g., general linear models such as hierarchical regression, logistic regression, ordinary least squares regression, etc.) but other methods include neural networks, latent variable modeling, support vector machines, genetic expression programming, etc. A combination of those independent variables that best predicts the values of the outcome measures can be considered a predictive model of those outcome measures (also referred to as behavioral outcomes) for a population (e.g., for individuals in that population), given a population that is appropriately-large for the chosen statistical approach. In certain examples, combinations of independent variables can be linear combinations and/or non-linear combinations. Additionally, as discussed above, some variables may provide no substantive contribution to the model and may be discarded to simplify the model's complexity. One process, known as LASSO (Least Absolute Shrinkage and Selection Operator) analysis, is a regression analysis method that performs variable selection and regularization to generate a desired model at varying degrees of complexity (e.g., with more/less independent variables contributing). Resulting selected parameters can be calculated and used to generate the desired behavioral outcome model, for example. While the process 900 described above describes a specific a complex sound that contains a consonant to vowel transition, it is contemplated that other complex sounds may be used, such as the complex sounds described above in Section I(a)(i) and Section I(a)(iv).

Figure 10:
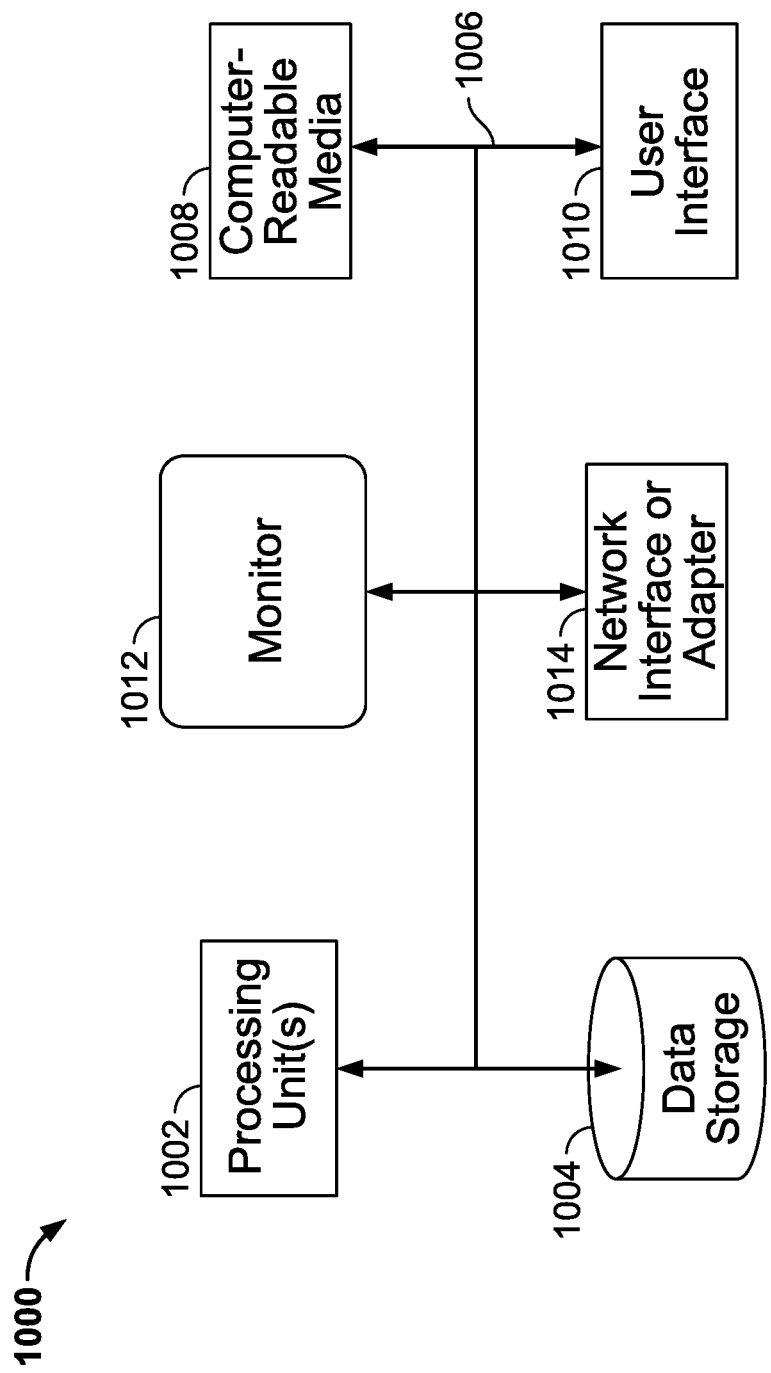
FIG. 10 illustrates an example of a suitable computing and networking environment 900 that may be used to implement various aspects of the present disclosure described in FIGS. 7 and 8 (e.g. the computing device 802 and corresponding components).

FIG. 10 illustrates an example of a suitable computing and networking environment 900 that may be used to implement various aspects of the present disclosure described in FIGS. 7 and 8 (e.g. the computing device 802 and corresponding components). As illustrated, the computing and networking environment 1000 includes a general purpose computing device 1000, although it is contemplated that the networking environment 1000 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 1000 may include various hardware components, such as a processing unit 1002, a data storage 1004 (e.g., a system memory), and a system bus 1006 that couples various system components of the computer 1000 to the processing unit 1002. The system bus 1006 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 1000 may further include a variety of computer-readable media 1008 that includes removable/non-removable media and volatile/nonvolatile media, but excludes transitory propagated signals. Computer-readable media 1008 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 1000. Communication media includes computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 1004 includes computer storage media in the form of volatile/nonvolatile memory such as read only memory (ROM) and random access memory (RAM). A basic input/output system (BIOS), containing the basic routines that help to transfer information between elements within the computer 1000 (e.g., during start-up) is typically stored in ROM. RAM typically contains data and/or program modules that are immediately accessible to and/or presently being operated on by processing unit 1002. For example, in one embodiment, data storage 1004 holds an operating system, application programs, and other program modules and program data.

Data storage 1004 may also include other removable/non-removable, volatile/nonvolatile computer storage media. For example, data storage 1004 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 10, provide storage of computer-readable instructions, data structures, program modules and other data for the computer 1000.

A user may enter commands and information through a user interface 1010 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 1002 through a user interface 1010 that is coupled to the system bus 1006, but may be connected by other interface and bus structures, such as a parallel port, game port or a universal serial bus (USB). A monitor 1012 or other type of display device is also connected to the system bus 1006 via an interface, such as a video interface. The monitor 1012 may also be integrated with a touch-screen panel or the like.

The computer 1000 may operate in a networked or cloud-computing environment using logical connections of a network interface or adapter 1014 to one or more remote devices, such as a remote computer. The remote computer may be a personal computer, a server, a router, a network PC, a peer device or other common network node, and typically includes many or all of the elements described above relative to the computer 1000. The logical connections depicted in FIG. 10 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 1000 may be connected to a public and/or private network through the network interface or adapter 1014. In such embodiments, a modem or other means for establishing communications over the network is connected to the system bus 1006 via the network interface or adapter 1014 or other appropriate mechanism. A wireless networking component including an interface and antenna may be coupled through a suitable device such as an access point or peer computer to a network. In a networked environment, program modules depicted relative to the computer 1000, or portions thereof, may be stored in the remote memory storage device.

EXAMPLES

The following examples are included to demonstrate various embodiments of the present disclosure. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Introduction to Examples

Although public awareness of sports-related concussion is on the rise, with more athletes being flagged for assessment following an impact, it remains a tricky injury to assess, diagnose and manage (Lovell, Collins & Bradley, 2004; McCrory et al., 2017; Owens, 2017). Compounding the trickiness is that the ultimate goal of evaluating and treating an athlete for a concussion is to deem him or her ready to resume the activity that led to the injury. Sports-related concussion, a mild traumatic brain injury (TBI) induced by an external mechanical force, is difficult to diagnose is because it affects function but not macro-structure. Thus, the effects of a sports-related concussion are invisible using conventional imaging methods (Shenton et al., 2012). In addition to being an injury of dysfunction rather than destruction, symptoms of a sports-related concussion are not specific to this injury but overlap with other disorders. A multimodal approach is required for concussion assessment, diagnosis, and management (McCrory et al., 2017). This multimodal approach combines tests of cognitive function, sensorimotor abilities including oculomotor, vestibular, and coordination, and behavioral reports of somatic symptoms such as headache, dizziness, or nausea (McCrory et al., 2017).

Some concussed individuals experience noticeable auditory complaints post-concussion, including ringing in the ears, an inability to ignore distracting sounds, and difficulty understanding speech in a noisy environment, such as a restaurant or cafeteria (Kraus et al., 2017; Kraus et al., 2016b; Musiek, Baran & Shinn, 2004; Turgeon, Champoux, Lepore, Leclerc & Ellemberg, 2011; Vander Werff & Rieger, 2017). The layout of the auditory system may make it susceptible to injury. The auditory system is uniquely complex, having more relays connecting the sensory organ to the brain than other sensory systems (Malmierca, 2015). Axons bi-directionally link each of the relays, traversing between the ear, brainstem, midbrain, and cortex (Malmierca, 2015; Malmierca & Ryugo, 2011). The precise signaling occurring along these multiple pathways requires a balance of neural inhibition and excitation choreographed across neural synapses (Wehr & Zador, 2003). In general, a neuron's axon is highly susceptible to damage from a mechanical force and is thought to be a chief site of impairment in traumatic brain injuries (Baugh et al., 2012; Giza & Hovda, 2014; Hay, Johnson, Smith & Stewart, 2016). Shearing or stretching of axons as a consequence of a mechanical force can initiate a dysfunctional metabolic cascade (Giza & Hovda, 2014), or potentially death of the injured axon (Baugh et al., 2012; Hay et al., 2016). The susceptibility of axons to mechanical force together with the complex interconnectivity of the auditory system, makes the auditory system a likely site of dysfunction following a head impact. Specifically, sports-related concussion may impact how the brain processes sound.

Humans with moderate to severe TBI (Ganes & Lundar, 1988; Kane et al., 1996; Liesienè, Kèvalas, Ulozienè & Gradauskienè, 2008; Munjal, Panda & Pathak, 2010) and animal models with mild to moderate TBI show delayed or reduced responses to simple sounds such as a click or tone (Amanipour, Cresoe, Borlongan, Frisina & Walton, 2016; Williamson, 2014). Additionally, the frequency-following response (FFR), which measures responses originating predominately in the auditory midbrain (Chandrasekaran & Kraus, 2010) and objectively assesses processing of complex sounds, such as speech or music (Kraus & White-Schwoch, 2015; Skoe & Kraus, 2010), has identified sound processing deficits in milder cases of TBI (Kraus et al., 2016a). Specifically, the FFR shows delayed and reduced processing of speech sounds weeks after a sports-related concussion in adolescents with post-concussion syndrome (Kraus et al., 2016b) and months to years after recovering from a sports-related concussion in collegiate student-athletes (Kraus et al., 2017). In adolescents with post-concussion syndrome, the effects observed include a reduction in encoding of the fundamental frequency, timing delays of peaks that correspond to the periodicity of the fundamental frequency, and reduced stimulus-to-response correlation and response magnitude (Kraus et al., 2016b), which both depend on the strength of encoding of the fundamental frequency (Skoe & Kraus, 2010). The legacy of concussion in the recovered collegiate student-athletes was specific to a reduction in fundamental-frequency encoding (Kraus et al., 2017). While these studies point to longer-term effects of sports-related concussion on sound processing, it is not known whether sound processing impairments are seen in the acute stage of concussion injury (i.e., 24-48 hours post-injury) or how this impairment manifests. FFR may provide a valuable adjunct in the clinical assessment of concussion. The FFR offers several advantages over current measures: it is highly reliable across test sessions—there are no practice effects, it is objective, meaning the patient does not need to respond in any way during the test, but may instead sleep or watch a movie, and the identical test can be used across ages and languages.

The long-term effects of concussion on speech processing reflect declines in processing the periodicity of lower-frequency, pitch-based cues (i.e., $F_0$). These pitch cues are important for identifying a speaker (e.g., knowing who is talking) and locking-on to that speaker's voice in difficult or noisy listening conditions (Carlyon, 2004). However, pitch is not the only important speech feature that the brain needs to process. Speech also contains higher-frequency components that comprise formants, which determine the phonetic identity of the speech sounds (Fairbanks & Grubb, 1961; Fitch, 2000). For example, higher-frequency information distinguishes a 'b' from a 'd'. Timing cues also convey important information about the phonetic identity of a sound (Fitch, 2000), for instance onset timing distinguishes a 't' from a 'd'.

Long-term deficits are specific to periodicity encoding. One hypothesis is that periodicity encoding is selectively affected by a sports-related concussion, manifesting in pitch-specific deficits, including declines in the fundamental frequency encoding, delays in the peaks that track the periodicity of the fundamental, reduced stimulus-to-response correspondence, and smaller response amplitude. This may be called the periodicity hypothesis. The alternate hypothesis, which may be the pervasive hypothesis, is that the acute impairments affect multiple aspects of auditory processing. That is, processing of both pitch and phonetic cues is disrupted acutely by a concussion but processing of phonetic cues (onset timing, high-frequency encoding) recovers more quickly than processing of periodic ones. As a first step in arbitrating between these two hypotheses, FFRs on collegiate football players were collected prior to the start of the football season to provide a baseline measure of auditory processing, and tested any concussed athletes again at 24-48 hours post-injury to identify acute changes in speech processing. If the periodicity hypothesis is correct, then only periodicity-based impairments should be observed during the acute concussion phase. If the pervasive hypothesis is correct, then both periodic and non-periodic deficits should be seen and these deficits should extend to both simple and complex sounds.

Based on the results of this study, pervasive effects were evident 24-48 hours post-concussion. These effects included delayed auditory brainstem response to a click (click-ABR) and FFR peaks, smaller amplitude FFRs, and poorer spectral encoding of the F0 and F1.

Example 1: Click-ABR Latency

Figure 1B:
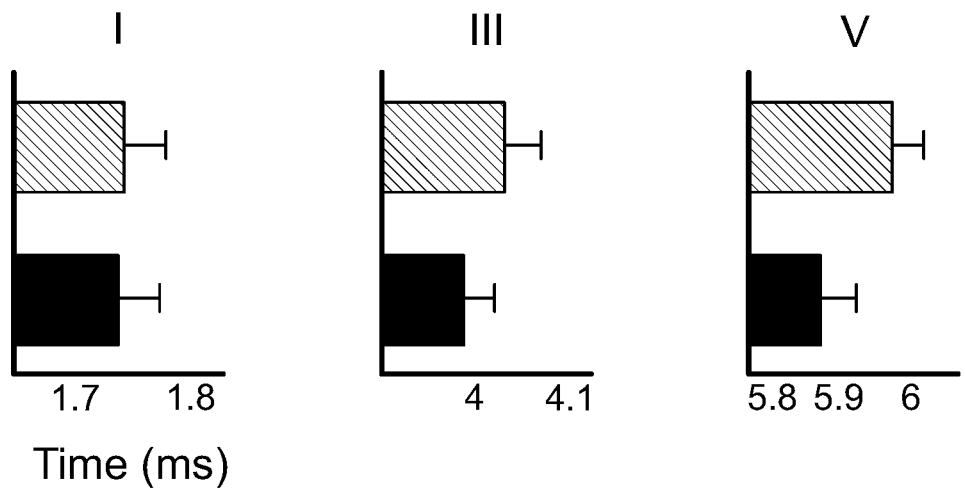
Figure 1C:
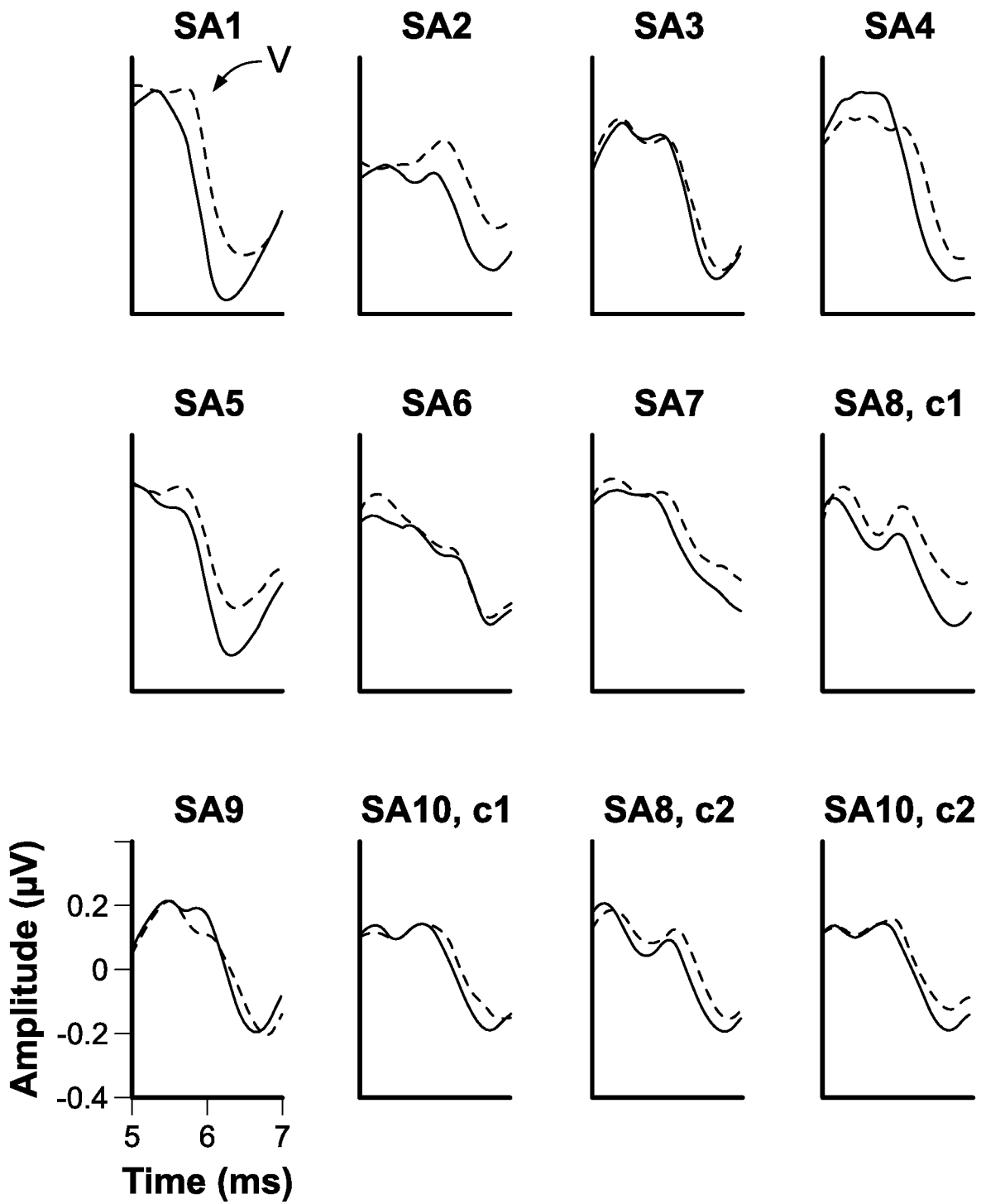

Peak I latency did not change following a concussion (t11=−0.804, p=0.438), suggesting the first synapse of the auditory nerve is intact, and that the peripheral hearing organ is healthy. Only 4 acute cases had a later peak I and this change was quite small. The average preseason to postconcussion latency shift was 0.007 ms later. However, latency delays were evident and reliable for peaks III (t11=−2.825, p=0.017) and V (t11=−4.32, p=0.001). Peak III was delayed in 10 of the 12 cases and the average latency shift was 0.045 ms. Peak V was delayed in 11 of the 12 cases and was delayed on average by 0.109 ms (FIGS. 1A-C).

Example 2: FFR Latency

In response to the speech syllable 'd', only the onset peaks, V (t11=−2.614, p=0.024) and A (t11=−3.642, p=0.004), were significantly delayed following a concussion. Peak V was delayed on average by 0.11 ms and A was delayed by 0.18 ms on average. Ten of the 12 acute cases showed a delay at peak V and 9 cases were delayed at peak A. Although peak E also showed a later latency post-concussion, with an average delay of 0.236 ms, (t11=−1.529, p=0.155), this effect was not significant; however, 9 of the 12 cases were delayed.

Figure 2A:
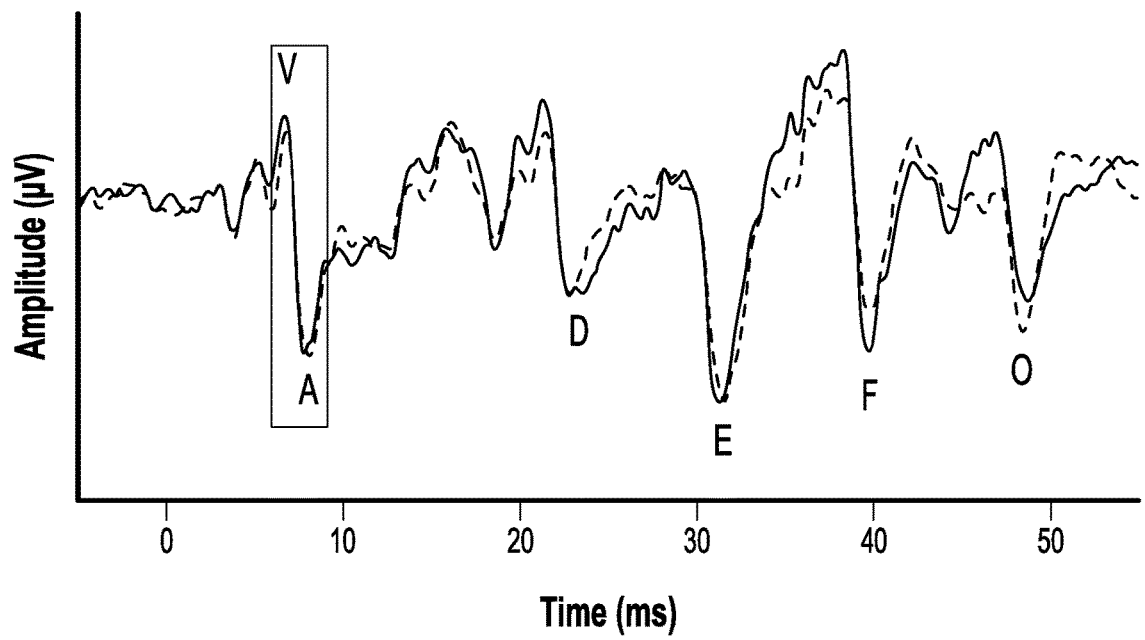
FIG. 2A-C illustrate that FFR latency is affected by concussion.
Figure 2B:
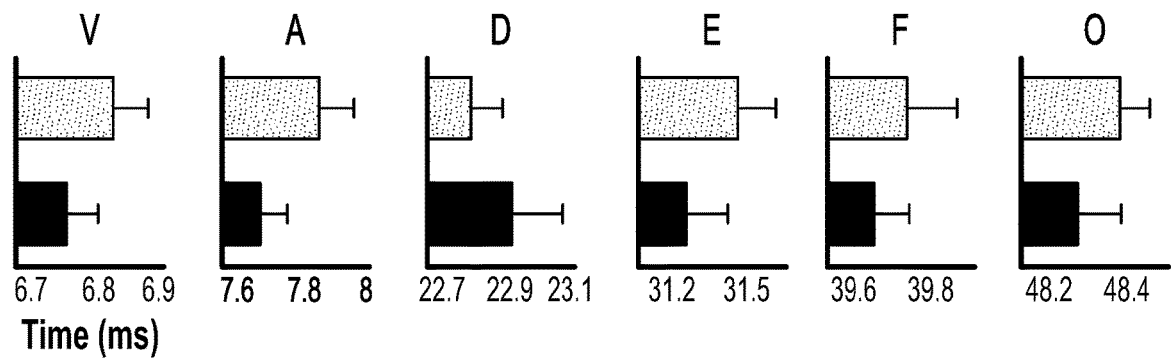
Figure 2C:
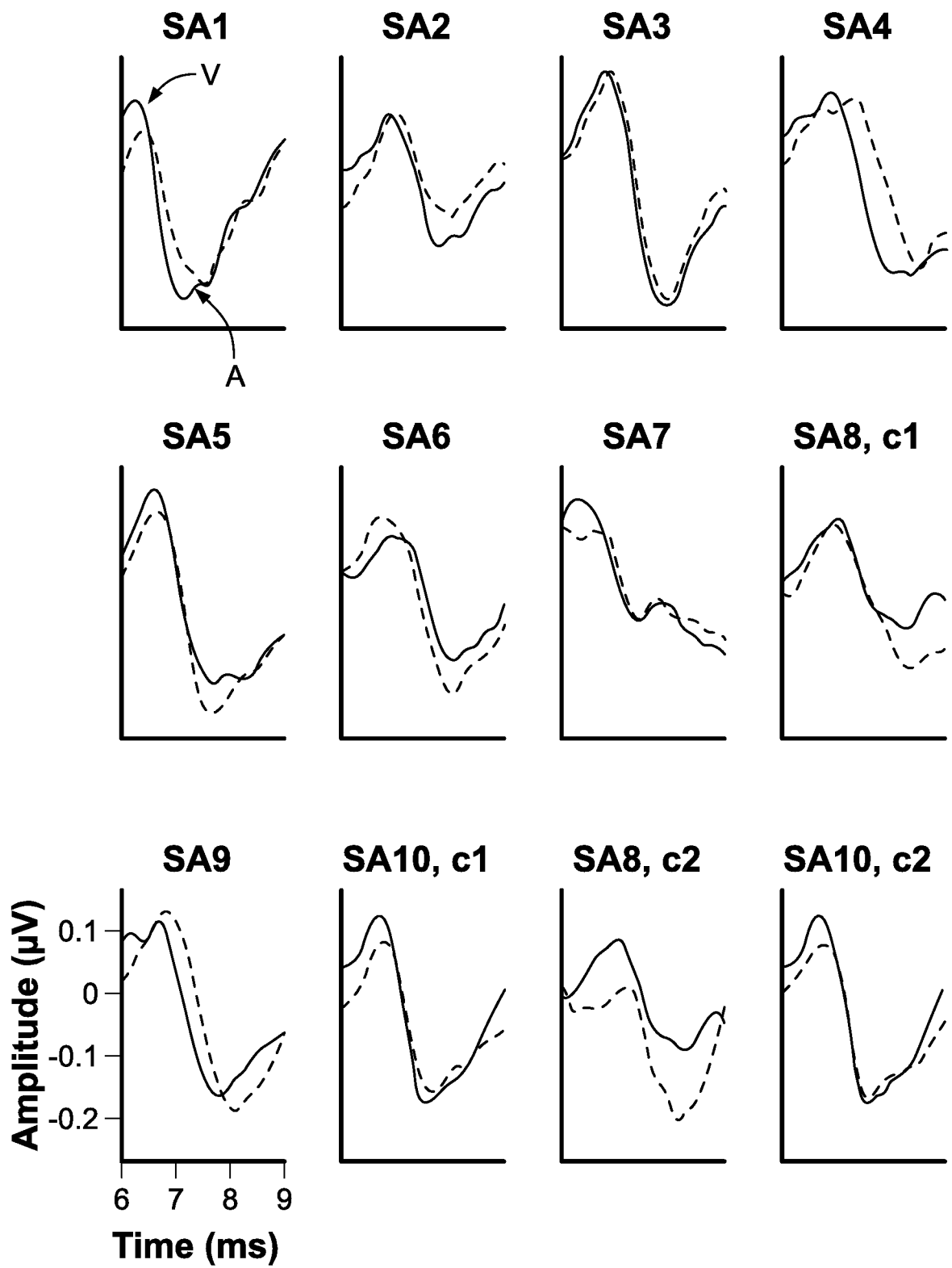
Figure 3A:
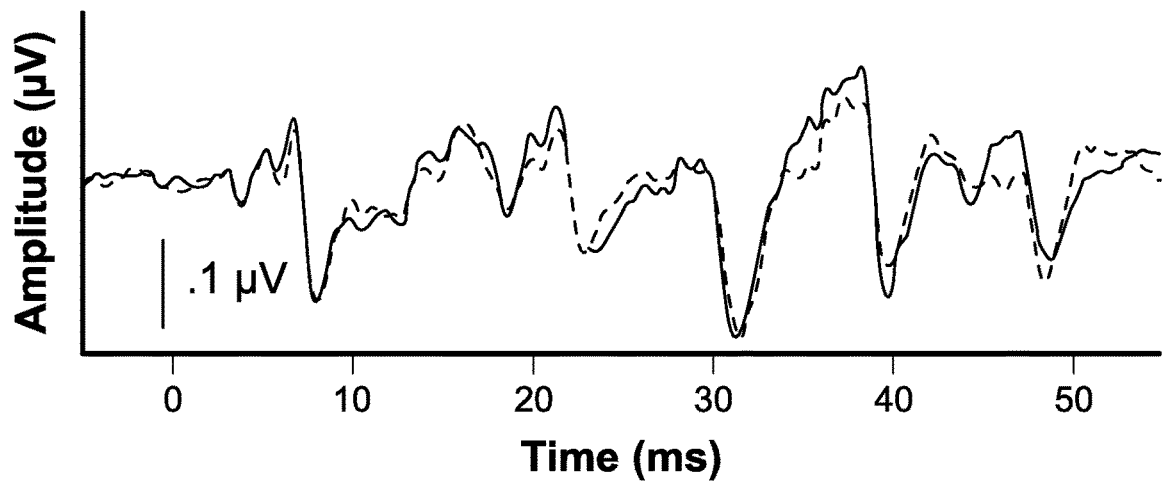
FIG. 3A-F illustrate that FFR magnitude is affected by concussion.
Figure 3B:
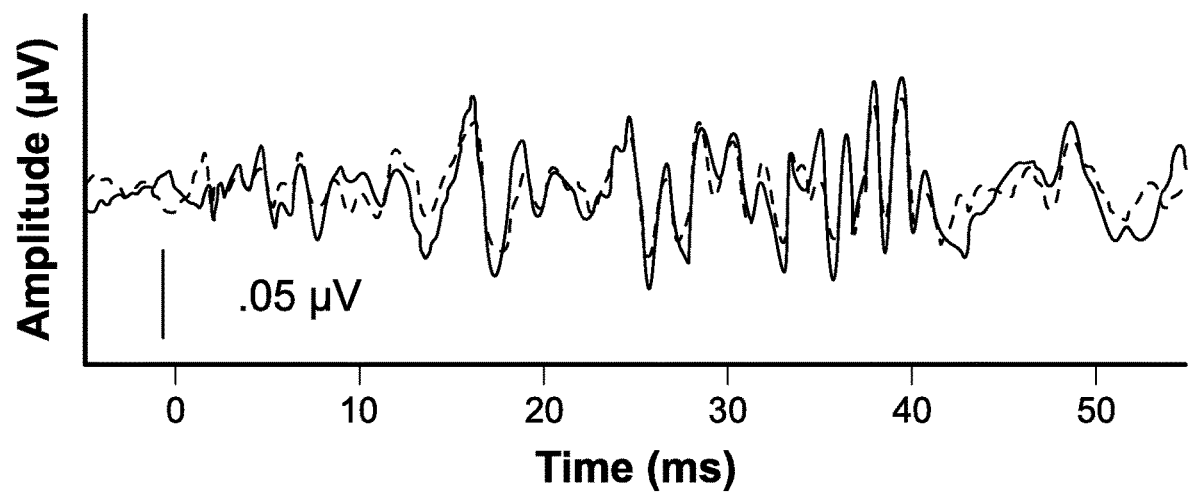
Figure 3C:
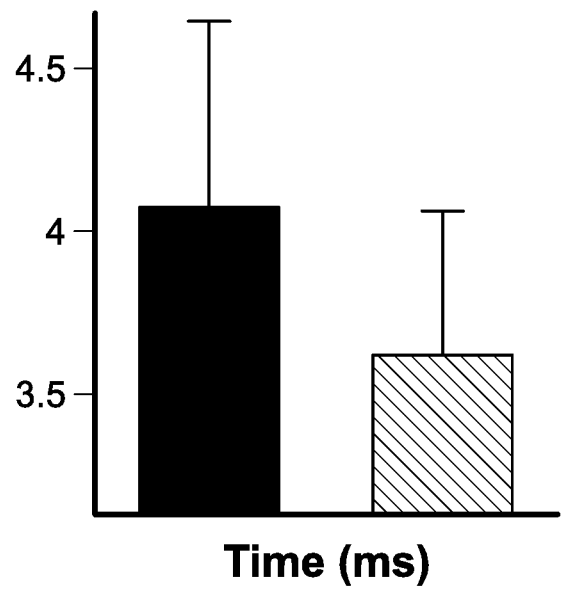
Figure 3E:
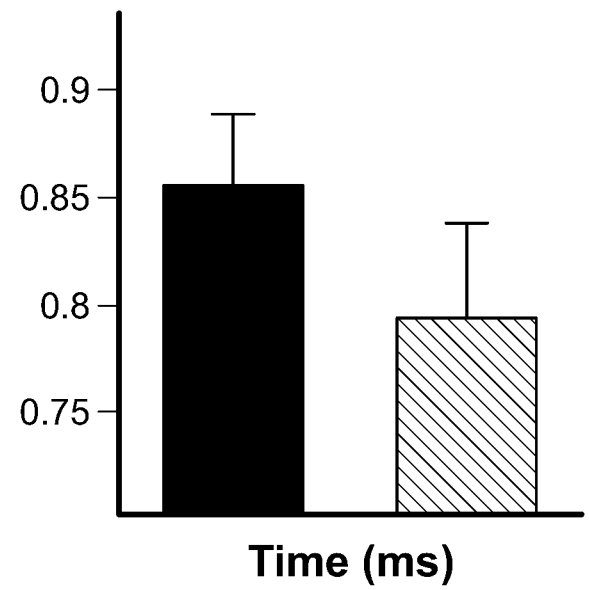
Figure 3D:
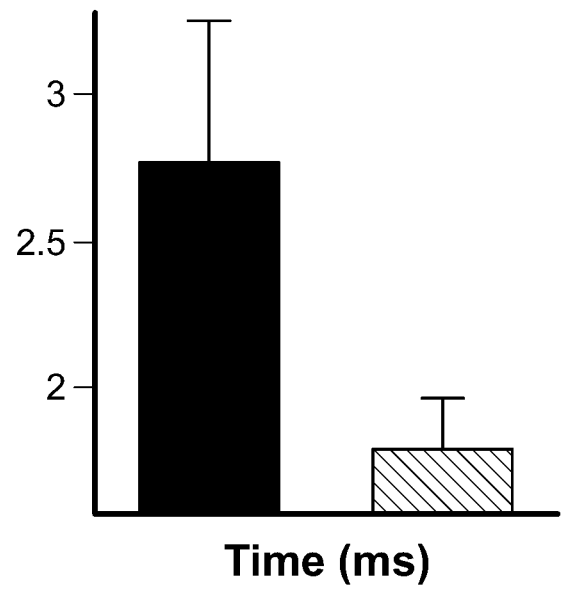
Figure 3F:
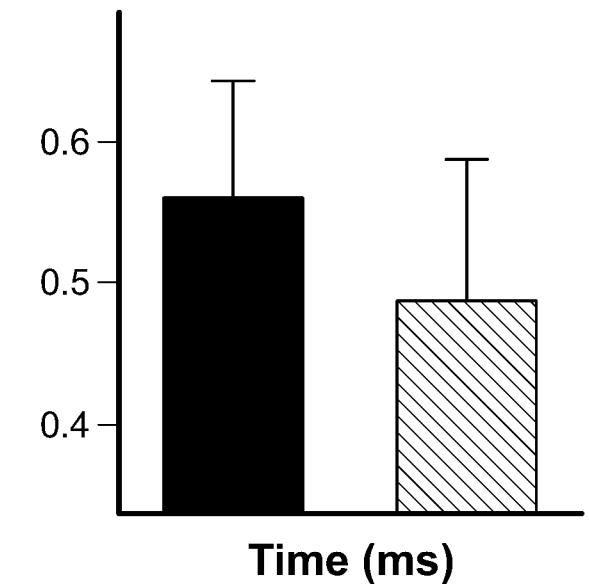
Figure 4A:
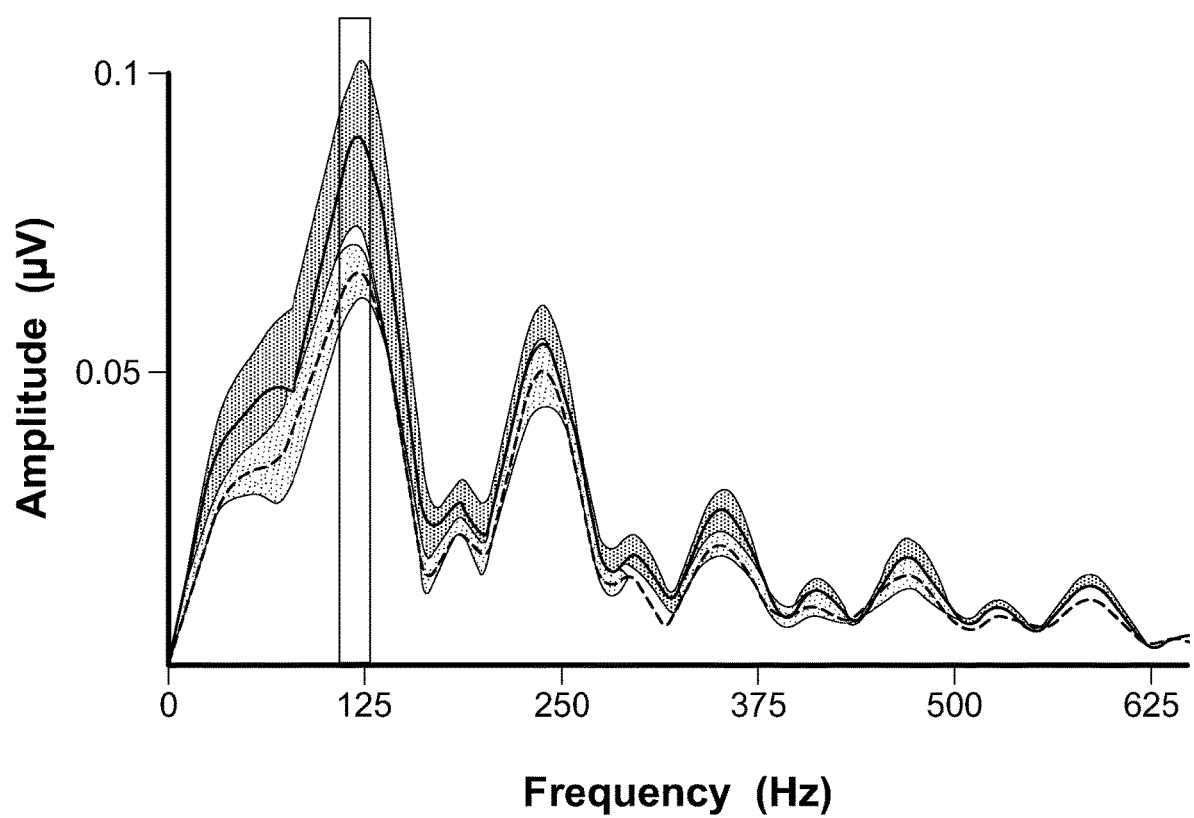
FIG. 4A-C illustrate that FFR F0 is affected by concussion.
Figure 4B:
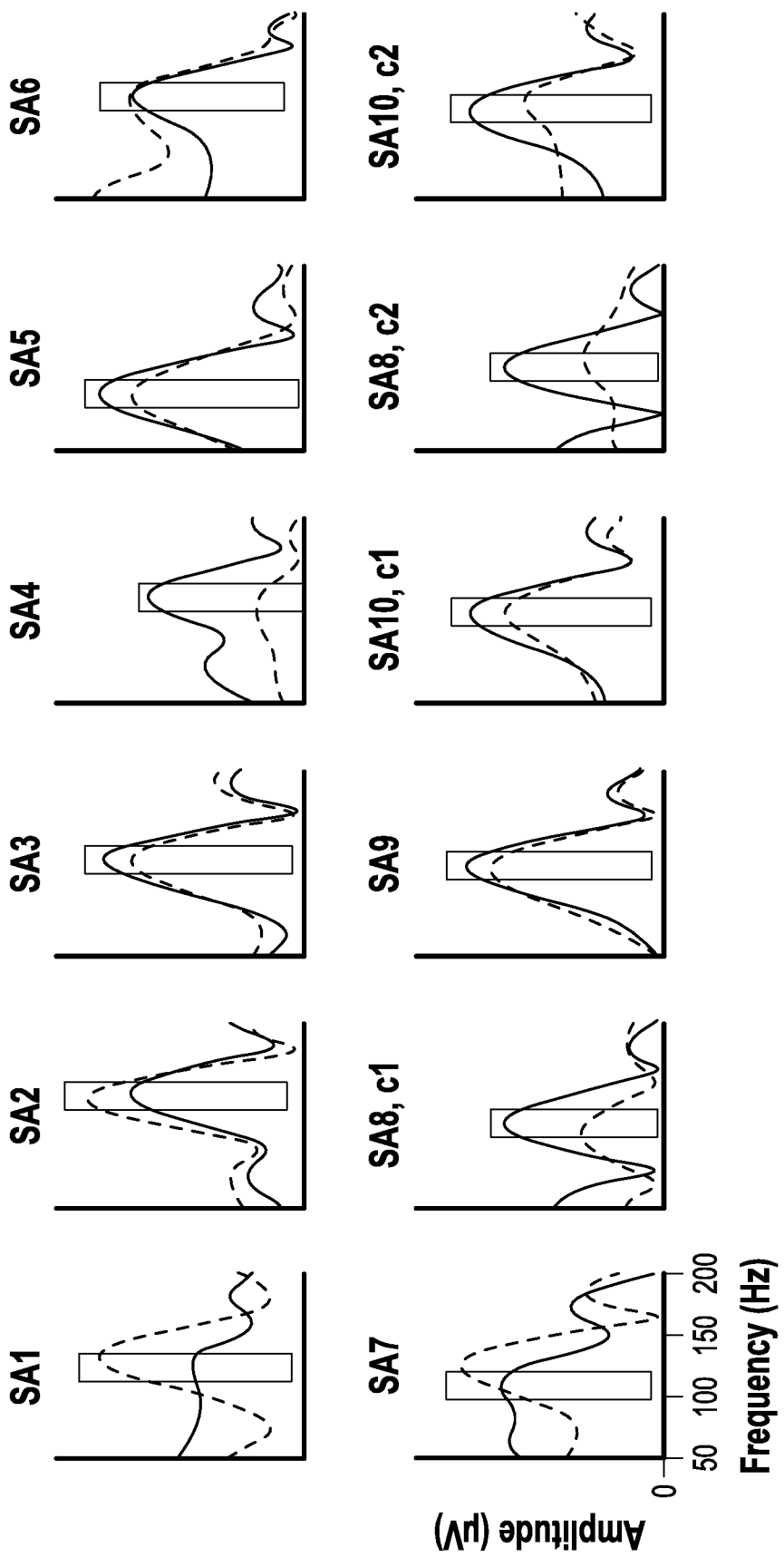
Figure 4C:
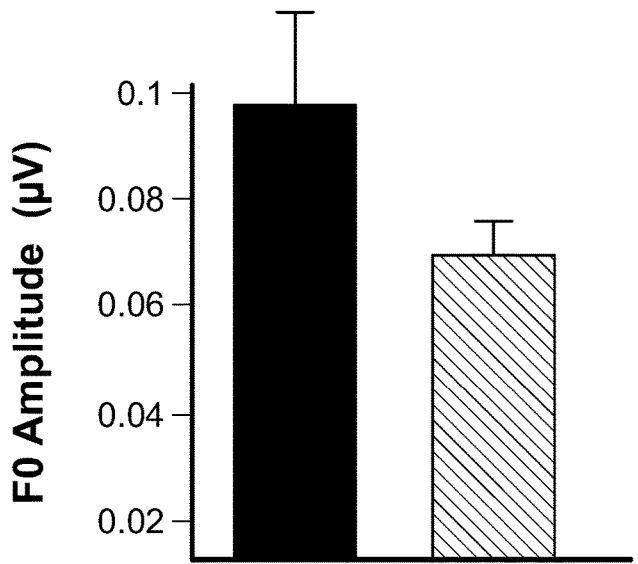

The remaining peaks did not show consistent delays across student-athletes: D (t11=1.225, p=0.246) was only delayed in 5 of the 12 cases and on average, the latency shifted earlier by 0.14 ms post-concussion; F (t11–0.663, p=0.521) was delayed in 6 cases with an average latency delay of 0.09 ms; and, O (t10=−1.701, p=0.12) was delayed in 8 cases with an average delay of 0.124 ms (FIGS. 2A-C).

Example 3: FFR Response Magnitude and Consistency

The signal-to-noise ratio of the fundamental frequency (F0)-maximized response did not show a significant decline in magnitude post-concussion (t11=1.044, p=0.319), although 7 of the 12 cases had a decline in pitch response magnitude and across the group, the average change in magnitude was a decline of 0.458. There was, however, a trending effect for the pitch response to be less consistent post-concussion (t11=1.926, p=0.08). Consistency of the response to the pitch declined on average by 0.06 and a decline in consistency was observed in 7 of the 12 acute concussion cases (FIGS. 3A-D).

The signal-to-noise ratio of the F1-maximized response was smaller immediately after a concussion (t11=2.389, p=0.034), declining, on average, 0.984. Eight of the 12 cases had a reduction in the magnitude of this response. Although 8 of 12 cases showed a decline in the across-trial consistency of their response to F1, this effect was not significant (t11=1.432, p=0.18). The average change in F1 consistency was a decline of 0.0714 (FIGS. 3A-D).

Example 4: FFR Pitch Encoding

There was a trending decline in the encoding of the F0 (t11=1.8, p=0.098), with 8 of the 12 cases showing a reduction in F0 (FIGS. 4A-D). The average change of F0 encoding was a decline of 0.03 µV post-concussion.

Example 5: FFR Phonetic Encoding

Figure 5A:
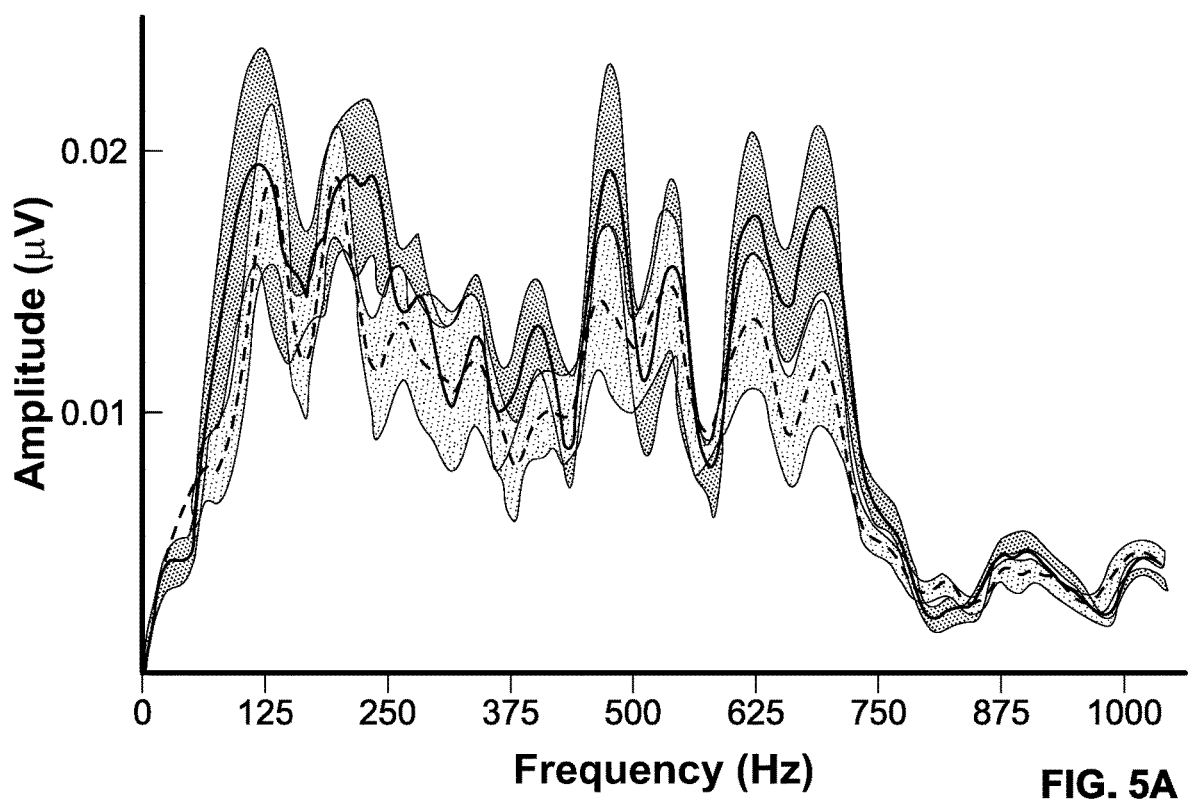
FIG. 5A-C illustrate that FFR F1 is affected by concussion.
Figure 5B:
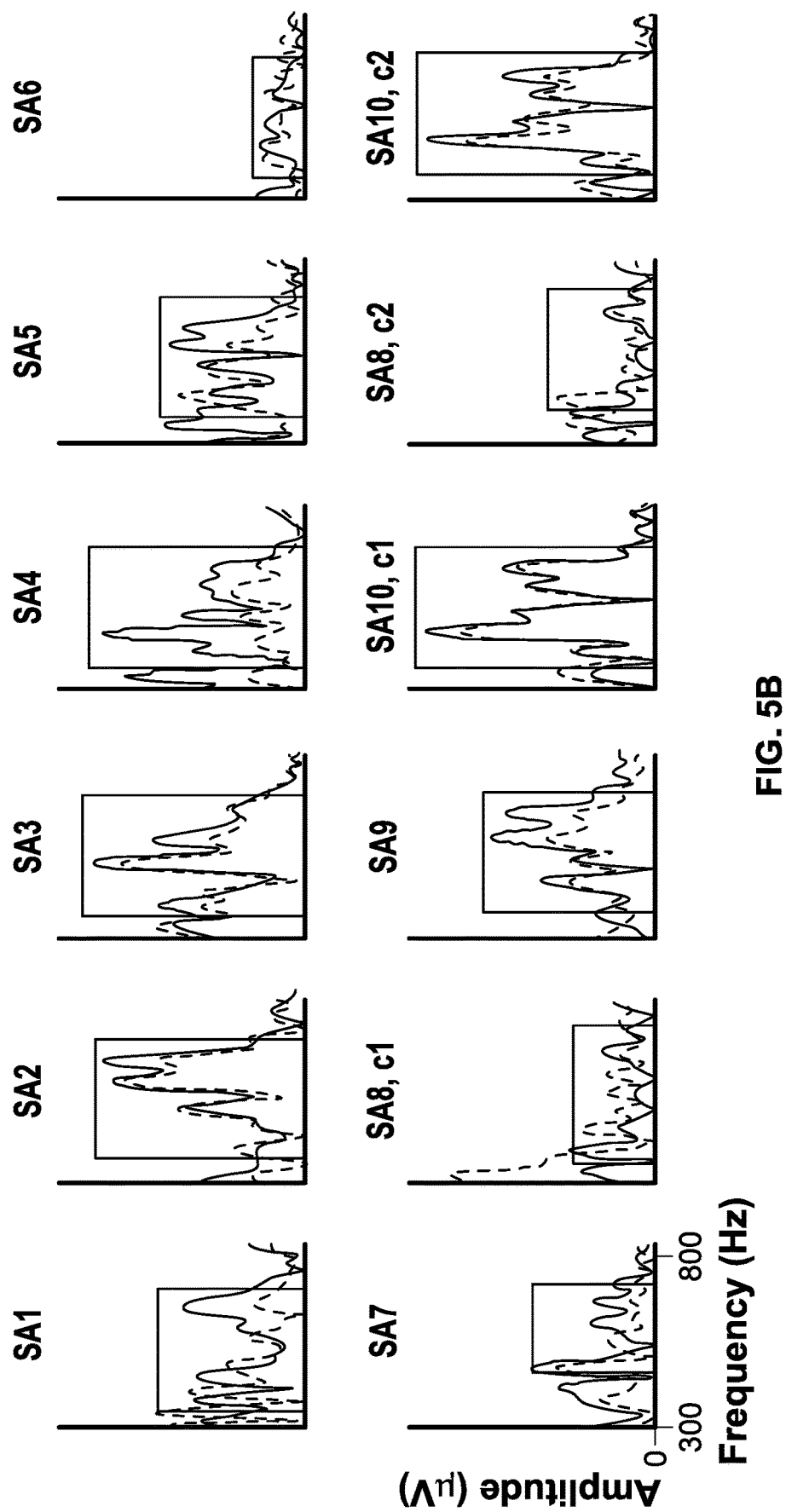
Figure 5C:
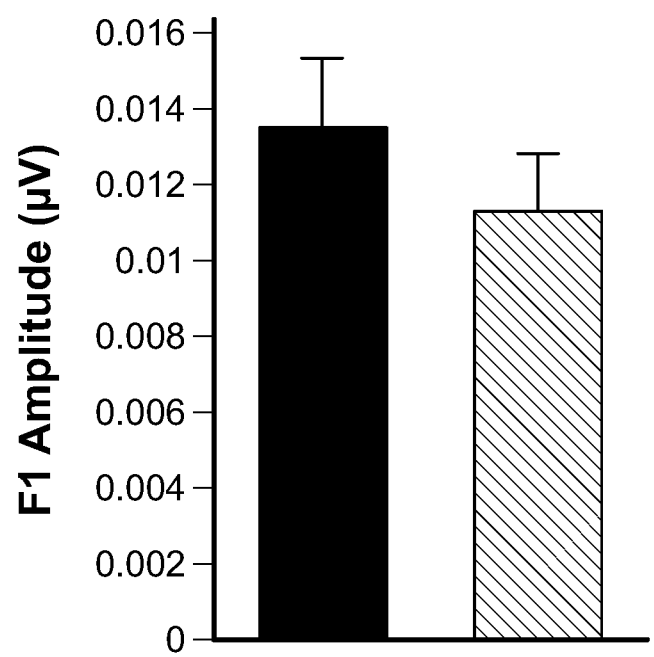

F1 encoding was poorer post-injury (t11=2.538, p=0.028); 9 of the 12 cases showed a decline in F1 encoding post-concussion (FIGS. 5A-C). The average change in F1 encoding following a concussion was a decline of 0.0022 µV.

Discussion for Examples 1 to 5

Figure 6A:
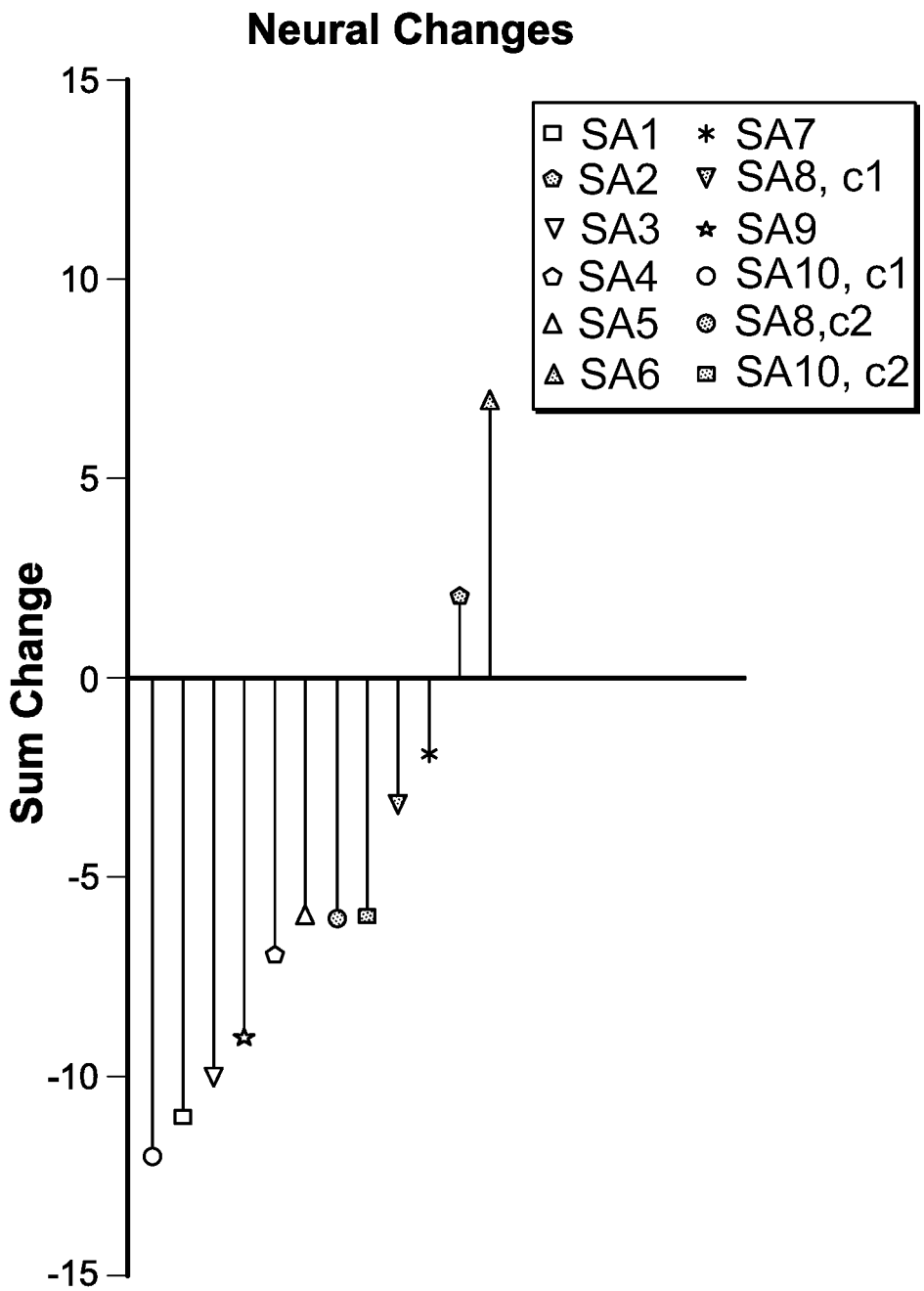
FIG. 6A-C illustrate that pervasive auditory pathophysiology is evident 24-48 hours post-concussion.
Figure 6B:
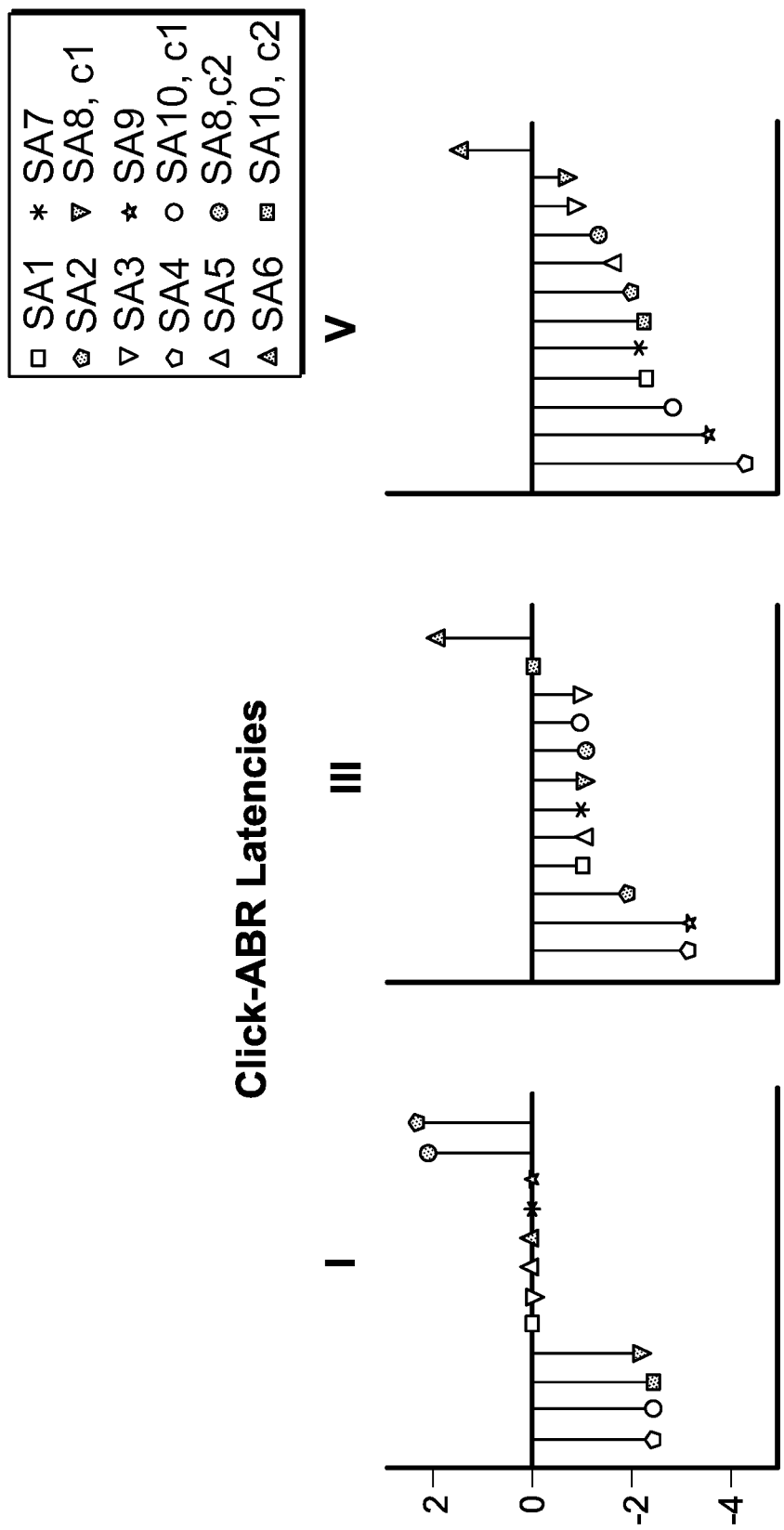
Figure 6C:
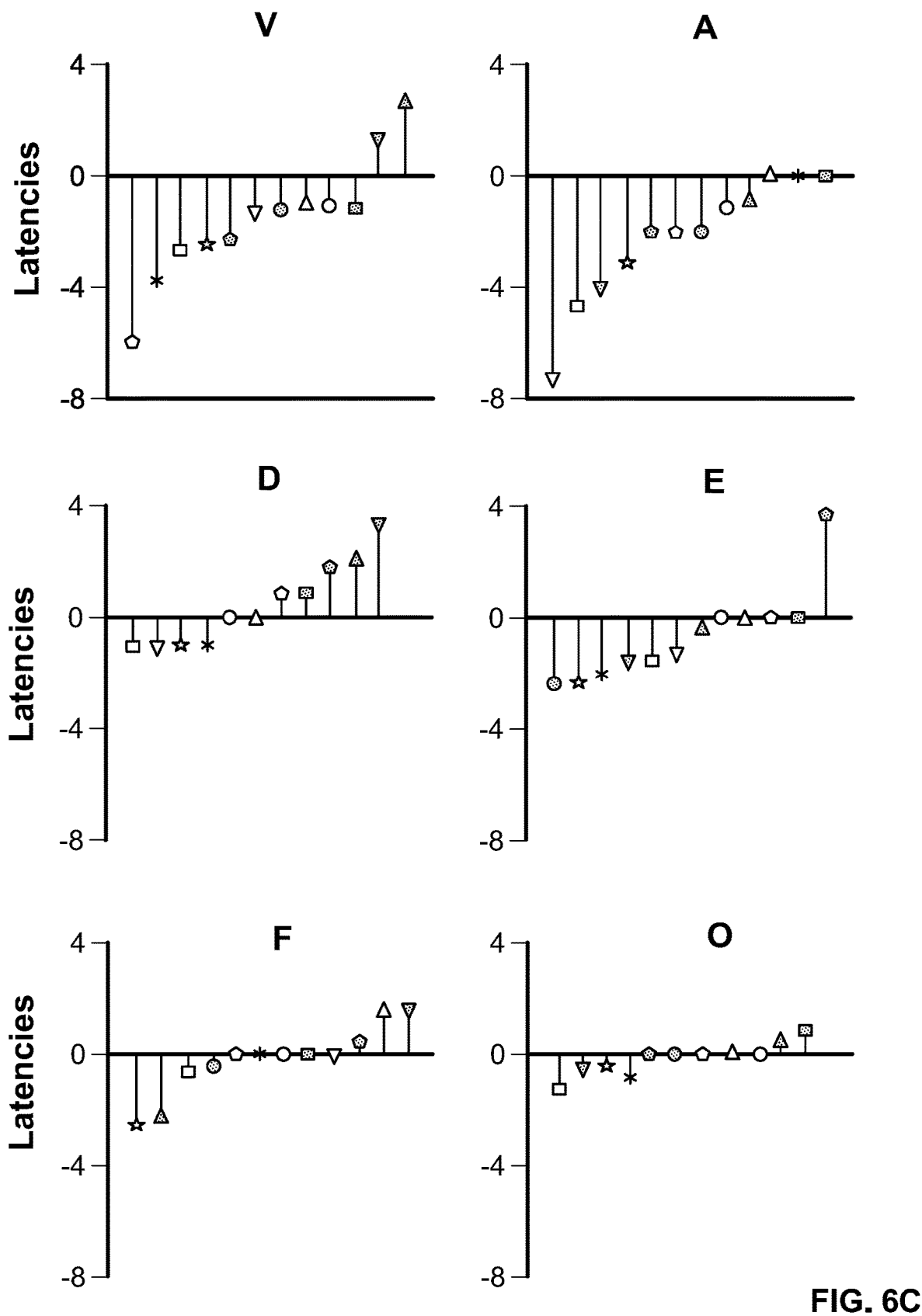
Figure 6C:
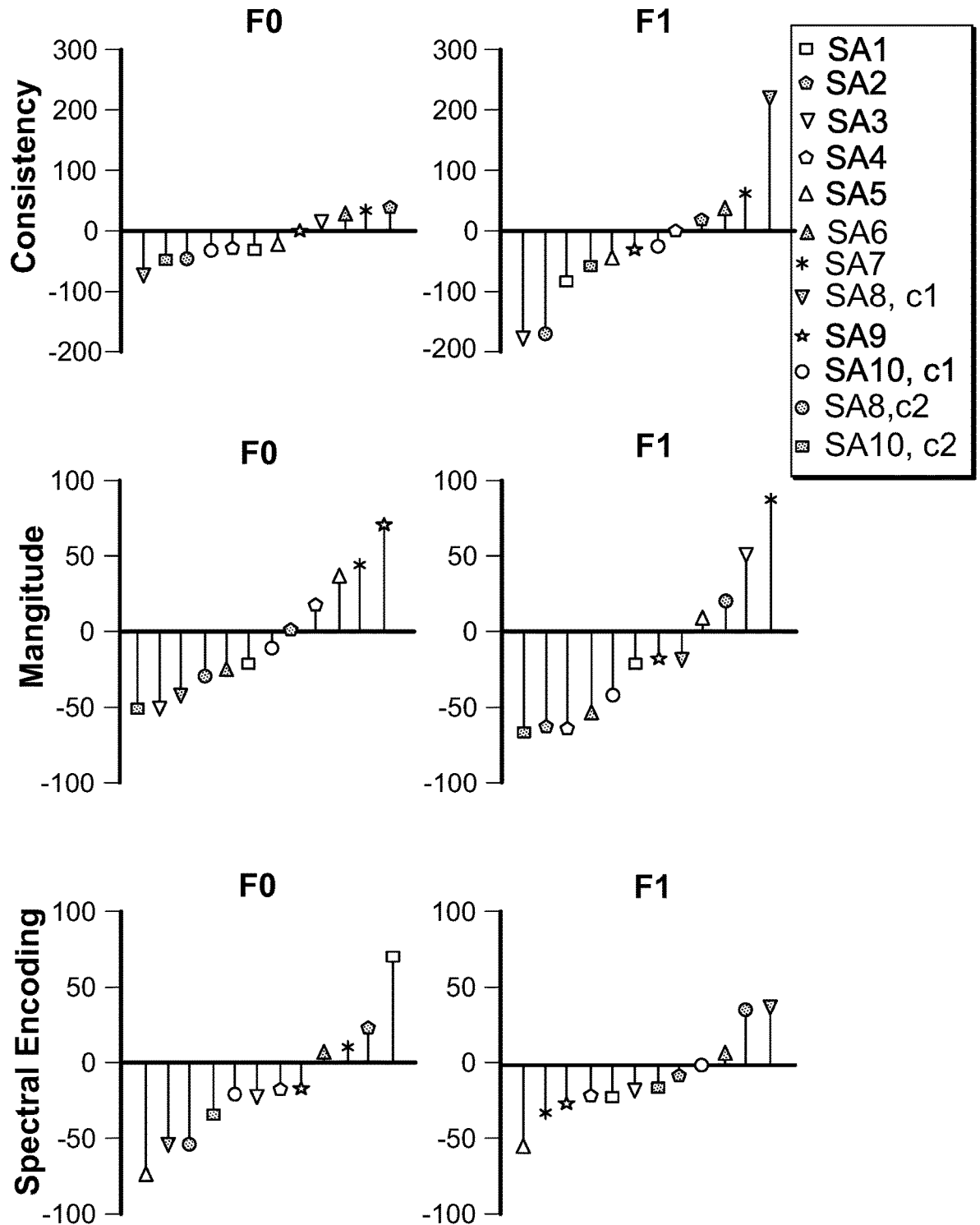

Central auditory system shows pervasive pathophysiology post-concussion: During the acute phase of concussion, the central auditory system shows extensive pathophysiology. That is, there are functional changes in central auditory processing following a sports-related concussion. Specifically, after a concussion, click-ABR and FFR peaks are delayed, pitch responses are less consistent, response magnitude is reduced, and encoding of the F0 and F1 of the speech sound is poorer (summarized in FIGS. 6A-C). Across the 12 cases, the most consistent effects were delayed III and V peaks of the click-evoked response, delays in the onset response to 'd' and declines in F0 and F1 spectral encoding. Importantly, click I latency was unaffected by concussion, indicating that the auditory nerve and periphery are unaffected. Thus, the deficits observed are unlikely to be the result of changes in hearing ability in the ear, but are the consequence of functional changes in central auditory processing. It may be suggested that the auditory system demonstrates pervasive pathophysiology acutely following a sports-related concussion.

This auditory pathophysiology is objectively measurable using a non-invasive, simple test of auditory processing, namely the FFR. Given that the auditory system is susceptible to a concussion and that the FFR can provide an objective measure of concussion, consideration of adding the FFR to the multimodal assessment of sports-related concussion is warranted. Additionally, a sports-related concussion can occur through a number of means, and individuals are affected differently by similar hits (McCrory et al., 2017). Adding a measure of auditory processing to the assessment may flag injuries that previously went unnoticed. By providing an objective window into auditory processing that has, to date, been overlooked, inclusion of the FFR provides a more comprehensive snapshot of neural function in an athlete suspected of sustaining a sports-related concussion. The FFR helps the clinician in weighing the subjective assessments reported by the patient together with the sensorimotor assessments that have become part of the standard protocol.

Understanding acute and long-term effects of concussion on auditory processing: These results support a distinction between acute and long-term effects of sports-related concussion on auditory processing. These findings support a model where long-term effects are specific to pitch encoding, while, in the acute injury stage, auditory processing is pervasively affected, with both pitch and phonetic processing demonstrating pathophysiology. Given the differences observed at these two time points, it is suggested that processing of pitch and phonetic information are both affected by a concussion but they recover along two different trajectories. The separate time courses of recovery for pitch and phonetic encoding could result from three possible mechanisms.

First, the observed differences in short- and long-term pathophysiology may be due to injury severity, whereby pitch encoding is only impaired in more severe injuries while phonetic encoding is always affected acutely following concussion. Encoding of phonetic information requires greater neural precision than pitch encoding because phonetic information is carried in higher frequencies. This precision greatly depends on the balance of excitatory and inhibitory neurotransmitters released at synapses and integrated with neurons (Gittelman, Wang, Colburn & Pollak, 2015; Stange-Marten et at, 2017; Wehr & Zador, 2003). Because a metabolic cascade of dysfunction upsets this communication between neurons (Giza & Hovda, 2014), it can presumably upset the precise neural timing required to process high-frequency, phonetic information. On the other hand, signals that encode pitch can be summed over a much broader temporal window (Oline, Ashida & Burger, 2016; Poeppel, 2003). A more deleterious injury that results in the death of axons through axonal shearing or a large number of neurons being rendered incapable of regulating cell signaling may be necessary for disruptions in pitch processing to be observed, Measuring FFRs in individuals across a range of TBIs can test this hypothesis.

A second possibility is that the protracted pitch recovery is the result of auditory-system plasticity. Specifically, following a concussion, intact neurons change what parts of the signal they encode to account for the signaling lost as a result of the injury. Pitch information is redundant in a speech signal, and is thus encoded in multiple ways within the auditory system (Krishnan & Gandour, 2009; Shamma & Klein, 2000; Winkler, Tervaniemi & Näätänen, 1997; Xu & Pfingst, 2008). Given the higher proportion of auditory pathways devoted to pitch relative to phonetic encoding, it is likely that more pitch-encoding pathways would remain following a concussion. Thus, some of these pitch pathways may shift to phonetic encoding, to salvage encoding of the higher-frequency cues (Asokan, Williamson, Hancock & Polley, 2017). To test this hypothesis, stimuli with pitches that are higher or lower in frequency to the current one could be used to determine if the same pitch and phonetic encoding changes are evident across frequencies.

The higher-frequency components of the FFR represent signaling localized to subcortical circuits (i.e., the inferior colliculus) but the lower-frequency pitch used in the current study may reflect pitch encoding across multiple cortical and subcortical auditory processing centers (Coffey, Herholz, Chepesiuk, Baillet & Zatorre, 2016), Thus, it is possible that acutely following the head injury there is neuroinflammation and axonal shearing that upsets the precise signaling between neighboring neurons required for high-frequency encoding but that recovery from these localized injuries occurs with time. In contrast, the response recorded to the pitch of the stimulus may show lasting impairments because it is a reflection of across-brain health. That is, the long-term effects of concussion on pitch processing may reflect permanent, minor damage to axons at multiple centers along the auditory pathway, which sums in the scalp-recorded FFR into an observable deficit. This would suggest that pitch processing, as measured by the FFR may be a highly-sensitive method of detecting subtle processing declines. Using a speech sound with a higher-frequency pitch to record FFRs in concussed student-athletes could test this hypothesis.

Auditory processing as an index of long-term pathophysiology: There is a real need to understand the link between repeat traumatic head injuries (rTBIs) and chronic traumatic encephalopathy (CTE), Given that the auditory system shows acute impairments that recover, but perhaps do not recover fully following a concussion, long-term auditory pathophysiology, as measured by the FFR, may be a herald of subsequent CTE. A longitudinal study that continues to track collision athletes beyond retirement is necessary to show that the FFR can provide an in-vivo index of CTE.

TABLE 1

Comparison of expected effects for each hypothesis.

| | Periodicity Hypothesis | Pervasive Hypothesis |
|---|---|---|
| Click | | |
| Latencies | | x |
| FFR | | |
| Onset Latencies | | x |
| Periodicity Latencies | x | x |
| F0 Magnitude | x | x |
| F1 Magnitude | | x |
| F0 Consistency | x | x |
| F1 Consistency | | x |
| F0 Spectral Encoding | x | x |
| F1 Spectral Encoding | | x |

Table 1 shows the comparison of expected effects for each hypothesis. If the periodicity hypothesis is true, then only F0-based measures should be impacted immediately post-concussion. If, however, the pervasive hypothesis is true, then all aspects of auditory processing are susceptible to concussion and could thus demonstrate acute pathophysiology.

Methods for Examples

Participants: Division I collegiate-football student-athletes (n=10, 10 males) participated in this study. Student-athletes were tested in the week prior to their first contact practice, providing a baseline response to which responses collected 24-48 hours after concussion were compared. All concussions were football-related injuries and two student-athletes sustained two concussions over the course of the season. Concussion diagnoses were made and recovery was managed by the team's medical staff following the current NCAA concussion protocol (NCAA, 2017). All participants consented to participate and study procedures were approved by the university's Institutional Review Board in accordance with the Declaration of Helsinki.

Stimuli and Recording Parameters: Responses were elicited to a click (a 100 μs broadband sound, presented in rarefacting polarity at a rate of 31.25 Hz) and a speech sound, 'd' (a 40 ms presented in alternating polarity at a rate of 10.9 Hz). The 'd' is a five-formant synthesized speech sound (Klatt, 1980) that includes an initial noise burst and a formant transition between the consonant and vowel. The fundamental frequency (F0) and the first three formants (F1, F2, F3) change linearly (F0: 103-125, F1: 220-720, F2: 1700-1240, F3: 2580-2500 Hz) while F4 (3600 Hz) and F5 (4500 Hz) remain constant. The click and 'd' were presented through an insert earphone to the right ear at 80 dB SPL. During data collection, the student-athlete sat in a comfortable chair and was instructed to rest or watch a captioned movie of his choice.

An auditory brainstem response to the click (click-ABR) and a frequency-following response to the 'd' (FFR) were collected using Ag/AgCl electrodes, with Cz referenced to the right ear lobe and forehead as ground. Stimuli were delivered and responses were collected with the Bio-logic Navigator Pro System (Natus Medical Incorporated, San Carlos, California). The click-ABR was sampled at 24.015 kHz and the FFR was sampled at 12 kHz. These responses were processed online, which included filtering from 70-2000 Hz for the click-ABR and 100-2000 Hz for the FFR. An artifact rejection criterion of ±23 µV was applied to both the click-ABR and FFR. Click averaging was performed over a 17.8 ms epoch, beginning at 8 ms prior to stimulus onset, and 'd' was averaged with a 75 ms recording epoch, beginning 15.8 ms prior to stimulus presentation. Three blocks of 2000 artifact-free trials were collected in response to the click and two blocks of 3000 artifact-free trials were averaged in response to 'd'. The click-ABR responses were averaged to create a 6000-sweep response. The FFR responses were averaged in two ways to generate two 6000-sweep averaged responses: one that maximized the response to the fundamental frequency (F0), which reflects pitch encoding, and one that maximized the response to the higher frequencies comprising the first formant (F1), which reflects phonetic encoding. To maximize the F0 response, the response to each polarity was averaged together while the F1 response was maximized by inverting one of the polarities prior to averaging (Aiken & Picton, 2008). Thus, pitch-based analyses of magnitude, consistency, and spectral encoding were performed on the F0-maximized response and phonetic-based analyses of magnitude, consistency, and spectral encoding were performed on the F1-maximized response.

Data Analysis: Multiple measures were derived from the ABR and FFR to test our hypotheses. These measures, and the predictions for each hypothesis, are summarized in Table 1.

Peak Latencies: Neural response timing was quantified by identifying stereotyped peaks in the ABR and FFR. Peak picking was performed using criteria consistent with those reported previously (Krizman, Skoe & Kraus, 2012). Briefly, for each student-athlete, latencies of peaks I, III, and V of the click-ABR and peaks V, A, D, E, F, and O of the FFR were visually identified (see FIGS. 1A-C and FIGS. 2A-C). Click peaks correspond to progressively more central structures of the auditory system (Hall, 2006; Hood, 1998). The FFR peaks correspond to the stimulus onset (V and A), offset (O) and periodicity corresponding to the F0 over the formant transition (D, E, and F). If the periodicity hypothesis is true, then the acute effects should be specific to the timing of peaks D, E, and F. If the pervasive hypothesis is true, then acute timing delays should be observable at all FFR peaks, as well as the peaks of the click-ABR (Table 1).

Response Magnitude: Signal-to-noise ratio provides a measure of the size of the evoked response relative to the non-stimulus noise levels, To calculate this relative response magnitude, the average root-mean-square magnitude of the response from 19.5 to 44.2 ms was divided by the average root-mean-square magnitude of the response during the 15 ms prestimulus interval. Response magnitude was calculated on both the F0-maximized and F1-maximized responses. If the periodicity hypothesis is true, then response magnitude deficits would be specific to the F0-maximized response as the F0 is the largest component of that response. If the pervasive hypothesis is true, then the effects should also appear in the F1-maximized response (Table 1).

Response Consistency: To measure the stability of the brain response across trials, the averaged response to the first 3000 trials of 'd' was correlated with the averaged response to the last 3000 trials of 'd'. The resultant r-value, which could range from 0 (no consistency) to 1 (perfect consistency), was used for plotting the data and was fisher z-transformed for statistical analyses. Response consistency was calculated on both the F0-maximized and F1-maximized responses. If the periodicity hypothesis is true, then response consistency deficits would be specific to the F0-maximized response as the F0 is the largest component of that response. If the pervasive hypothesis is true, then the effects could also appear in the F1-maximized response (Table 1).

Spectral Encoding: Spectral encoding was analyzed using a fast Fourier analysis of the formant transition of 'd' (19.5-44.2 ms), a region of the response that includes peaks D, E, and F. Over this region, the F0 increases linearly from 109.7 Hz to 125 Hz. To determine F0 encoding for each individual, the maximum peak nearest the mean F0 of 117 Hz in the baseline preseason response was chosen as their F0. A 20 Hz bin, centered at the F0 was averaged to determine the mean F0 amplitude for each participant. This same bin was used to measure F0 amplitude post-concussion. Similarly, the F1 increases from 374 Hz to 720 Hz during the formant transition and so the maximum peak nearest the mean F1 frequency (547 Hz) in the baseline preseason response was determined to be the center frequency of the student-athlete's F1 response and a bin of 547 Hz was averaged to determine F1 encoding for that individual. The same bin was applied to measure F1 encoding in the post-concussion response. If the periodicity hypothesis is true, then the acute effects should be specific to the F0; if, however, the pervasive hypothesis is true, then both the F0 and F1 should show acute processing declines (Table 1).

Statistical Analyses: Paired, two-tail t-tests comparing preseason to post-concussion responses were used to determine significant differences in the click-ABR and FFR following concussion. Data processing was performed using custom routines coded in Matlab 2010b (The MathWorks, Inc., Natick, MA) and statistical analyses were performed in SPSS (SPSS Inc., Chicago, IL).

REFERENCES FOR EXAMPLES

Amanipour, R., Cresoe, S., Borlongan, C., Frisina, R., & Walton, J. (2016). Effects of Mild Traumatic Brain Injury on Auditory Function in a Mouse Model. Paper presented at the Biomedical Engineering Conference (SBEC), 2016 32nd Southern.

Asokan, M., Williamson, R. S., Hancock, K. E., & Polley, D. B. (2017). Homeostatic normalization of sensory gain in auditory corticofugal feedback neurons. bioRxiv, 162909.

Baugh, C. M., Stamm, J. M., Riley, D. O., Gavett, B. E., Shenton, M. E., Lin, A., Nowinski, C. J., Cantu, R. C., McKee, A. C., & Stern, R. A. (2012). Chronic traumatic encephalopathy: neurodegeneration following repetitive concussive and subconcussive brain trauma. Brain imaging and behavior, 6(2), 244-254.

Carlyon, R. P. (2004). How the brain separates sounds. Trends in cognitive sciences, 8(10), 465-471.

Chandrasekaran, B., & Kraus, N. (2010). The scalp-recorded brainstem response to speech: Neural origins and plasticity. Psychophysiology, 47, 236-246.

Coffey, E. B., Herholz, S. C., Chepesiuk, A. M., Baillet, S., & Zatorre, R. J. (2016). Cortical contributions to the auditory frequency-following response revealed by MEG. Nature Communications, 7.

Fairbanks, G., & Grubb, P. (1961). A psychophysical investigation of vowel formants. Journal of Speech & Hearing Research.

Fitch, W. T. (2000). The evolution of speech: a comparative review. Trends in cognitive sciences, 4(7), 258-267.

Ganes, T., & Lundar, T. (1988). EEG and evoked potentials in comatose patients with severe brain damage. Electroencephalography and Clinical Neurophysiology, 69(1), 6-13.

Gittelman, J. X., Wang, L., Colburn, H., & Pollak, G. D. (2015). Inhibition shapes response selectivity in the inferior colliculus by gain modulation. Inferior Colliculus Microcircuits, 394.

Giza, C. C., & Hovda, D. A. (2014). The new neurometabolic cascade of concussion. Neurosurgery, 75(suppl_4), S24-S33.

Hall, J. W. (2006). New handbook of auditory evoked responses. Boston Mass: Pearson.

Hay, J., Johnson, V. E., Smith, D. H., & Stewart, W. (2016). Chronic traumatic encephalopathy: the neuropathological legacy of traumatic brain injury. Annual Review of Pathology: Mechanisms of Disease, 11, 21-45.

Hood, L. J. (1998). Clinical applications of the auditory brainstem response. San Diego: Singular Pub. Group.

Kane, N., Curry, S., Rowlands, C., Manara, A., Lewis, T., Moss, T., Cummins, B., & Butler, S. (1996). Event-related potentials—neurophysiological tools for predicting emergence and early outcome from traumatic coma. Intensive Care Medicine, 22(1), 39-46.

Klatt, D. (1980). Software for cascade/parallel formant synthesizer. Journal of the Acoustical Society of America, 67, 971-975.

Kraus, N., Lindley, T., Colegrove, D., Krizman, J., Otto-Meyer, S., Thompson, E. C., & White-Schwoch, T. (2017). The neural legacy of a single concussion. Neuroscience Letters.

Kraus, N., Lindley, T., Thompson, E. C., Krizman, J., Cook, K., White-Schwoch, T., Colegrove, D., & LaBella, C. (2016a). Making sense of sound: A biological marker for concussion. American Congress of Rehabilitation Medicine Annual Conference, Chicago, IL.

Kraus, N., Thompson, E. C., Krizman, J., Cook, K., White-Schwoch, T., & LaBella, C. (2016b). Auditory biological marker of concussion in children. Scientific Reports, 97(12), e11.

Kraus, N., & White-Schwoch, T. (2015). Unraveling the Biology of Auditory Learning: A Cognitive—Sensorimotor—Reward Framework. Trends in cognitive sciences, 19(11), 642-654.

Krishnan, A., & Gandour, J. T. (2009). The role of the auditory brainstem in processing linguistically-relevant pitch patterns. Brain and Language, 110(3), 135-148.

Krizman, J., Skoe, E., & Kraus, N. (2012). Sex differences in auditory subcortical function. Clinical Neurophysiology, 123(3), 590-597.

Liesienè, R., Kévalas, R., Uloziené, I., & Gradauskiene, E. (2008). Search for clinical and neurophysiological prognostic patterns of brain coma outcomes in children. Medicina, 44(4), 273-279.

Lovell, M., Collins, M., & Bradley, J. (2004). Return to play following sports-related concussion. Clinics in Sports Medicine, 23(3), 421-441.

Malmierca, M. S. (2015). Anatomy and physiology of the mammalian auditory system Encyclopedia of Computational Neuroscience (pp. 155-186): Springer.

Malmierca, M. S., & Ryugo, D. K. (2011). Descending connections of auditory cortex to the midbrain and brain stem The auditory cortex (pp. 189-208): Springer.

McCrory, P., Meeuwisse, W., Dvorak, J., Aubry, M., Bailes, J., Broglio, S., Cantu, R. C., Cassidy, D., Echemendia, R. J., & Castellani, R. J. (2017). Consensus statement on concussion in sport—the 5th international conference on concussion in sport held in Berlin, October 2016. British Journal of Sports Medicine, bjsports-2017-097699.

Mez, J., Solomon, T. M., Daneshvar, D. H., Stein, T. D., & McKee, A. C. (2016). Pathologically confirmed chronic traumatic encephalopathy in a 25-year-old former college football player. JAMA neurology, 73(3), 353-355.

Montenigro, P. H., Alosco, M. L., Martin, B. M., Daneshvar, D. H., Mez, J., Chaisson, C. E., Nowinski, C. J., Au, R., McKee, A. C., & Cantu, R. C. (2017). Cumulative head impact exposure predicts later-life depression, apathy, executive dysfunction, and cognitive impairment in former high school and college football players. Journal of Neurotrauma, 34(2), 328-340.

Munjal, S. K., Panda, N, K., & Pathak, A. (2010). Relationship between severity of traumatic brain injury (TBI) and extent of auditory dysfunction. Brain Injury, 24(3), 525-532.

Musiek, F. E., Baran, J. A., & Shinn, J. (2004). Assessment and remediation of an auditory processing disorder associated with head trauma. Journal of the American Academy of Audiology, 15(2), 117-132.

NCAA. (2017). Concussion Diagnosis and Management Best Practices, from http://www.ncaa.org/sport-science-institute/concussion-diagnosis-and-management-best-practices Oline, S. N., Ashida, G., & Burger, R. M. (2016). Tonotopic optimization for temporal processing in the cochlear nucleus. Journal of Neuroscience, 36(32), 8500-8515.

Owens, S. (2017). Hearing Test May Detect Concussion in Kids. Neurology Now.

Poeppel, D. (2003). The analysis of speech in different temporal integration windows: cerebral lateralization as 'asymmetric sampling in time'. Speech Communication, 41(1), 245-255.

Shamma, S., & Klein, D. (2000). The case of the missing pitch templates: How harmonic templates emerge in the early auditory system. The Journal of the Acoustical Society of America, 107(5), 2631-2644.

Shenton, M. E., Hamoda, H., Schneiderman, J., Bouix, S., Pasternak, O., Rathi, Y., Vu, M.-A., Purohit, M. P., Helmer, K., & Koerte, I. (2012). A review of magnetic resonance imaging and diffusion tensor imaging findings in mild traumatic brain injury. Brain imaging and behavior, 6(2), 137-192, Skoe, E., & Kraus, N. (2010). Auditory brain stem response to complex sounds: A tutorial. Ear and Hearing, 31(3), 302-324.

Stange-Marten, A., Nebel, A. L., Sinclair, J, L., Fischl, M., Alexandrova, O., Wohlfrom, H., Kopp-Scheinpflug, C., Pecka, M., & Grothe, B. (2017). Input timing for spatial processing is precisely tuned via constant synaptic delays and myelination patterns in the auditory brainstem. Proceedings of the National Academy of Sciences, 114(24), E4851-E4858.

Turgeon, C., Champoux, F., Lepore, F., Leclerc, S., & Ellemberg, D. (2011). Auditory processing after sport-related concussions. Ear and Hearing, 32(5), 667-670.

Vander Werff, K. R., & Rieger, B. (2017). Brainstem evoked potential indices of subcortical auditory processing after mild traumatic brain injury. Ear and Hearing, 38(4), e200-e214.

Wehr, M., & Zador, A. M. (2003). Balanced inhibition underlies tuning and sharpens spike timing in auditory cortex. Nature, 426(6965), 442.

Williamson, T. L. (2014). Brainstem Auditory Evoked Potentials and Network Dysfunction In Mild Traumatic Brain Injury.

Winkler, I., Tervaniemi, M., & Näätänen, R. (1997). Two separate codes for missing-fundamental pitch in the human auditory cortex. The Journal of the Acoustical Society of America, 102(2), 1072-1082.

Xu, L., & Pfingst, B. E. (2008). Spectral and temporal cues for speech recognition: Implications for auditory prostheses. Hearing Research, 242(1), 132-140.

What is claimed is:

1. A method of identifying a non-penetrating brain injury in a subject that has experienced a brain injury, the method comprising:
   (a) fitting the subject with electrodes to measure voltage potentials generated from the subject's brain;
   (b) administering to the subject an acoustic stimulus comprising a complex sound;
   (c) recording voltage potentials from the subject's brain for at least the duration of the acoustic stimulus;
   (d) analyzing the voltage potentials to determine at least one component of the brain response to the acoustic stimulus; and
   (e) identifying the subject as having a non-penetrating brain injury if a value for at least one component of the brain response is anomalous;
   wherein the at least one component of the brain response is fundamental frequency ($F_0$), neural timing of a sustained response peak, response amplitude over a time window that comprises some or all of the complex sound, or stimulus-response correlation over a time window that encompasses some or all of the complex sound.

2. The method of claim 1, wherein the complex sound comprises a consonant and a consonant-to-vowel transition.

3. The method of claim 2, wherein the consonant is an obstruent stop consonant.

4. The method of claim 2, wherein the consonant-to-vowel transition comprises a low, back vowel.

5. The method of claim 1, wherein the complex sound comprises a speech sound or a non-speech vocal sound.

6. The method of claim 5, wherein the time window comprises at least one formant.

7. The method of claim 6, wherein the time window comprises at least two formants.

8. The method of claim 5, wherein the time window comprises an unvoiced consonant release and/or a transient component corresponding to onset of voicing.

9. The method of claim 5, wherein the speech sound comprises at least one syllable selected from /da/, /pa/, /ka/, /ta/, /ba/, and /ga/.

10. The method of claim 1, wherein the at least one component of the brain response comprises neural timing of a sustained response peak.

11. The method of claim 1, wherein the at least one component of the brain response comprises response amplitude over a time window that comprises some or all of the complex sound.

12. The method of claim 1, wherein the at least one component of the brain response comprises stimulus-response correlation over a time window that comprises some or all of the complex sound, and the stimulus-response correlation is calculated in the time domain.

13. The method of claim 1, wherein the at least one component of the brain response comprises stimulus-response correlation over a time window that comprises some or all of the complex sound, and the stimulus-response correlation is calculated in the frequency domain.

14. The method of claim 1, wherein the at least one component of the brain response comprises $F_0$ amplitude, $F_0$ phase consistency, $F_0$ sharpness, $F_0$ frequency error, pitch tracking, or a combination thereof.

15. The method of claim 14, wherein the at least one component of the brain response comprises $F_0$ amplitude.

16. The method of claim 1, wherein step (e) comprises identifying the subject as having a non-penetrating brain injury if values for at least two components of the brain response are anomalous.

17. The method of claim 16, wherein the at least two components of the brain response are $F_0$ and stimulus-response correlation over a time window that encompasses the complex sound.

18. The method of claim 1, wherein the subject also shows an anomalous Auditory Brainstem Response (ABR).

19. The method of claim 1, wherein step (e) is performed within at least one of 12, 24, or 48 hours after the subject experienced the brain injury.

20. The method of claim 1, further comprising:
   administering to the subject a second acoustic stimulus comprising a click; and
   analyzing the subject's click-ABR.

21. A method for assessing a subject's recovery from a non-penetrating brain injury, the method comprising:
   (a) in response to a brain injury of the subject, performing an acute evaluation of the subject's brain response to an acoustic stimulus by:
      (i) fitting the subject with electrodes to measure voltage potentials generated from the subject's brain;
      (ii) administering to the subject an acoustic stimulus comprising a complex sound;
      (iii) recording voltage potentials from the subject's brain for at least the duration of the acoustic stimulus;
      (iv) analyzing the voltage potentials to determine at least one component of the brain response to the acoustic stimulus; and
      (v) identifying a value for at least one component of the brain response that is anomalous;
      wherein the at least one component of the brain response is fundamental frequency ($F_0$), neural timing of a sustained response peak, response amplitude over a time window that comprises some or all of the complex sound, and stimulus-response correlation over a time window that encompasses some or all of the complex sound;
   (b) re-testing the subject's brain response to the acoustic stimulus at a later time by repeating steps a(i) to a(iv), and then identifying a value for the at least one component of the brain response that was anomalous in step (a)(v) ("the re-test value"); and
   (c) calculating the difference between the anomalous value and the re-test value;
   wherein the subject is determined to be recovering from the non-penetrating brain injury if there is a change in the re-test value that is greater than would be expected by chance, and the direction of the change indicates an improvement in the component of the brain response; and
   wherein the subject is determined to not be recovering from the non-penetrating brain injury if (a) there is not a change in the re-test value that is greater than would be expected by chance, and the direction of the change indicates an improvement in the component of the brain response, or (b) when there is a change in the re-test value that is greater than would be expected by chance, and the direction of the change indicates a deterioration in the component of the brain response.

22. A system for identifying a brain injury, the system comprising a computing device comprising at least one processor configured to:

receive an indication of a brain injury of a subject;
in response to the indication, immediately perform an evaluation of the subject's brain response to an acoustic stimulus by:
generating an acoustic stimulus comprising a complex sound;
obtaining voltage potential data from a brain response corresponding to an auditory pathway of a subject, wherein the voltage potential data is obtained during presentation of the acoustic stimulus to the subject;
analyzing the voltage potential data to determine at least one component of the brain response; and
generating and storing, in a memory in operable communication with the at least one processor, an indication of a non-penetrating brain injury when a first value for at least one component of the brain response is anomalous;
wherein the at least one component of the brain response is fundamental frequency ($F_0$), neural timing of a sustained response peak, response amplitude over a time window that comprises some or all of the complex sound, or stimulus-response correlation over a time window that encompasses some or all of the complex sound.

23. The system of claim 22, wherein the at least one processor is further configured to generate and store, in the memory, an indication of no non-penetrating brain injury when a second value for at least one other component of the brain response is not anomalous.

24. The system of claim 22, wherein the at least one component of the brain response comprises $F_0$ amplitude, $F_0$ phase consistency, $F_0$ sharpness, $F_0$ frequency error, pitch tracking, or a combination thereof.

25. The system of claim 22, wherein the complex sound comprises a speech sound or a non-speech vocal sound.

26. The system of claim 25, wherein the speech sound comprises at least one syllable selected from /da/, /pa/, /ka/, /ta/, /ba/, and /ga/.

27. The system of claim 22, wherein the voltage potential data is obtained from at least one electrode fit to the subject, the at least one electrode in operable communication with the computing device.

* * * * *